United States Patent
Bernick et al.

(10) Patent No.: US 10,206,932 B2
(45) Date of Patent: *Feb. 19, 2019

(54) NATURAL COMBINATION HORMONE REPLACEMENT FORMULATIONS AND THERAPIES

(71) Applicant: TherapeuticsMD, Inc., Boca Raton, FL (US)

(72) Inventors: Brian A. Bernick, Boca Raton, FL (US); Peter H. R. Persicaner, Boca Raton, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 78 days.

This patent is subject to a terminal disclaimer.

(21) Appl. No.: 14/719,933

(22) Filed: May 22, 2015

(65) Prior Publication Data

US 2015/0342963 A1 Dec. 3, 2015

Related U.S. Application Data

(60) Provisional application No. 62/002,090, filed on May 22, 2014.

(51) Int. Cl.
*A01N 45/00* (2006.01)
*A61K 31/56* (2006.01)
*A61K 31/565* (2006.01)
*A61K 9/10* (2006.01)
*A61K 31/57* (2006.01)
*A61K 9/48* (2006.01)

(52) U.S. Cl.
CPC ............. *A61K 31/565* (2013.01); *A61K 9/10* (2013.01); *A61K 9/4858* (2013.01); *A61K 31/57* (2013.01)

(58) Field of Classification Search
None
See application file for complete search history.

(56) References Cited

U.S. PATENT DOCUMENTS

| | | |
|---|---|---|
| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 6/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 8/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |

(Continued)

FOREIGN PATENT DOCUMENTS

BR PI1001367-9 A2 7/2012
CA 2612380 12/2006

(Continued)

OTHER PUBLICATIONS

US 6,214,374, 04/2001, Schmirler et al. (withdrawn)
Pachman et al., "Management of menopause-associated vasomotor symptoms: Current treatment options, challenges and future directions," International Journal of Women's Health, May 7, 2010.*
U.S. Appl. No. 13/684,002, filed Nov. 21, 2012, U.S. Pat. No. 8,633,178, Jan. 21, 2014.
U.S. Appl. No. 13/843,362, filed Mar. 15, 2013.
U.S. Appl. No. 13/843,428, filed Mar. 15, 2013, U.S. Pat. No. 9,301,920, Apr. 5, 2016.

(Continued)

*Primary Examiner* — Jared Barsky
(74) *Attorney, Agent, or Firm* — Kilpatrick Townsend & Stockton LLP

(57) ABSTRACT

Pharmaceutical compositions for co-administering estradiol and progesterone to a human subject in need thereof are provided. In some embodiments, the pharmaceutical composition comprises solubilized estradiol, suspended progesterone, and a solubilizing agent comprising a medium chain (C6-C12) oil.

20 Claims, 4 Drawing Sheets

(56) References Cited

U.S. PATENT DOCUMENTS

| | | |
|---|---|---|
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,164,416 A | 11/1992 | Nagai et al. |
| 5,211,952 A | 5/1993 | Spicer |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 8/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth |
| 5,543,150 A | 8/1996 | Bologna et al. |
| 5,547,948 A | 8/1996 | Barcomb |
| 5,556,635 A | 9/1996 | Grognet |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Liorzou |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Math |
| 5,607,691 A | 3/1997 | Solas |
| 5,607,693 A | 3/1997 | Bonte |
| 5,609,617 A | 3/1997 | Cady |
| 5,620,705 A | 4/1997 | Dong et al. |
| 5,626,866 A | 5/1997 | Heiber |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,653,983 A | 8/1997 | Bonte |
| 5,656,286 A | 8/1997 | Miranda et al. |
| 5,660,839 A | 8/1997 | Allec |
| 5,662,927 A | 9/1997 | Ehrlich |
| 5,663,160 A | 9/1997 | Dumas |
| 5,676,968 A | 10/1997 | Lipp et al. |
| 5,677,292 A | 10/1997 | Li et al. |
| 5,686,097 A | 11/1997 | Crisologo |
| 5,693,335 A | 12/1997 | Xia |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Mantelle |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi |
| 5,770,227 A | 6/1998 | Dong |
| 5,776,495 A | 7/1998 | Duclos et al. |
| 5,780,044 A | 7/1998 | Tipton |
| 5,780,050 A | 7/1998 | Jain |
| 5,788,980 A | 8/1998 | Nabahi |
| 5,788,984 A | 8/1998 | Schmidt |
| 5,789,442 A | 8/1998 | Garfield et al. |
| 5,811,416 A | 9/1998 | Chwalisz et al. |
| 5,811,547 A | 9/1998 | Nalcamichi et al. |
| 5,814,329 A | 9/1998 | Shah |
| 5,820,878 A | 10/1998 | Shinmura |
| 5,827,200 A | 10/1998 | Caillouette |
| 5,840,327 A | 11/1998 | Gale |
| 5,843,468 A | 12/1998 | Yum |
| 5,843,979 A | 12/1998 | Wille |
| 5,858,394 A | 1/1999 | Lipp |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Yum |
| 5,885,612 A | 3/1999 | Meconi |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen |
| 5,904,931 A | 5/1999 | Gunther |
| 5,906,830 A | 5/1999 | Farinas |
| 5,912,010 A | 6/1999 | Wille |
| 5,916,176 A | 6/1999 | Caillouette |
| RE36,247 E | 7/1999 | Plunkett et al. |
| 5,919,477 A | 7/1999 | Bevan |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Fikstad |
| 5,958,446 A | 9/1999 | Miranda et al. |
| 5,962,445 A | 10/1999 | Stewart |
| 5,968,919 A | 10/1999 | Gyurik |
| 5,972,372 A | 10/1999 | Saleh et al. |
| 5,985,311 A | 11/1999 | Cordes |
| 5,985,850 A | 11/1999 | Falk |
| 5,985,861 A | 11/1999 | Levine et al. |
| 5,993,856 A | 11/1999 | Ragavan et al. |
| 5,989,568 A | 12/1999 | De Lacharriere |
| 6,001,846 A | 12/1999 | Edwards et al. |
| 6,007,835 A | 12/1999 | Bon Lapillonne et al. |
| 6,010,715 A | 1/2000 | Pollock |
| 6,013,276 A | 1/2000 | Teillaud |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Garfield |
| 6,056,972 A | 5/2000 | Hermsmeyer |
| 6,060,077 A | 5/2000 | Meignant |
| 6,068,853 A | 5/2000 | Berner |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 7/2000 | Lacy et al. |
| 6,106,848 A | 8/2000 | Willcox |
| 6,117,446 A | 9/2000 | Place |
| 6,117,450 A | 9/2000 | Dittgen et al. |
| 6,124,362 A | 9/2000 | Bradbury |
| 6,133,251 A | 10/2000 | Dittgen et al. |
| 6,133,320 A | 10/2000 | Yallampalli et al. |
| 6,139,868 A | 10/2000 | Hoffmann |

(56) References Cited

U.S. PATENT DOCUMENTS

| | | |
|---|---|---|
| 6,139,873 A | 10/2000 | Hughes, Jr. et al. |
| 6,149,935 A | 11/2000 | Tenzel |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Rubinstein |
| 6,225,297 B1 | 5/2001 | Stockemann |
| 6,227,202 B1 | 5/2001 | Matapurkar |
| 6,228,383 B1 | 5/2001 | Hansen |
| 6,228,852 B1 | 5/2001 | Shaak |
| 6,242,509 B1 | 6/2001 | MacQueen |
| 6,245,811 B1 | 6/2001 | Horrobin |
| 6,262,115 B1 | 7/2001 | Guittard et al. |
| 6,267,984 B1 | 7/2001 | Hamlin |
| 6,274,165 B1 | 8/2001 | Meconi |
| 6,277,418 B1 | 8/2001 | Marakverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Vo |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Leyba |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Houze |
| 6,465,005 B1 | 10/2002 | Biali |
| 6,465,006 B1 | 10/2002 | Zhang |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Seibertz |
| 6,526,980 B2 | 3/2003 | Tracy et al. |
| 6,528,094 B1 | 3/2003 | Savoir et al. |
| 6,531,149 B1 | 3/2003 | Meconi |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Murray |
| 6,548,491 B2 | 4/2003 | Tanabe et al. |
| 6,551,611 B2 | 4/2003 | Elliesen et al. |
| 6,555,131 B1 | 4/2003 | Wolff |
| 6,562,367 B1 | 5/2003 | Wolff |
| 6,562,370 B2 | 5/2003 | Luo |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo |
| 6,610,652 B2 | 8/2003 | Adams et al. |
| 6,610,670 B2 | 8/2003 | Blckensfeld et al. |
| 6,610,674 B1 | 8/2003 | Schreiber |
| 6,635,274 B1 | 10/2003 | Carter |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Tamarkin |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Pike |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Boyd |
| 6,977,250 B2 | 12/2005 | Rodriguez |
| 6,978,945 B2 | 12/2005 | Wong et al. |
| 6,995,149 B1 | 2/2006 | Reilhac |
| 7,004,321 B1 | 2/2006 | Hackbarth |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Paris |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang |

(56) References Cited

U.S. PATENT DOCUMENTS

| | | |
|---|---|---|
| 7,097,853 B1 | 8/2006 | Keister |
| 7,101,342 B1 | 9/2006 | Caillouette |
| 7,105,573 B2 | 9/2006 | Krajcik |
| 7,135,190 B2 | 11/2006 | Piao et al. |
| 7,153,522 B1 | 12/2006 | Ikeura |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villaneuva et al. |
| 7,497,855 B2 | 3/2009 | Ausiello et al. |
| 7,498,303 B2 | 3/2009 | Arnold |
| 7,534,765 B2 | 5/2009 | Gregg et al. |
| 7,534,780 B2 | 5/2009 | Ring |
| 7,550,142 B2 | 6/2009 | Giles-Komar et al. |
| 7,563,565 B1 | 7/2009 | Matsuo et al. |
| 7,569,274 B2 | 8/2009 | Alphonse |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White |
| 7,815,936 B2 | 10/2010 | Hasenzahl |
| 7,815,949 B2 | 10/2010 | Cohen |
| 7,829,115 B2 | 11/2010 | Besins et al. |
| 7,829,116 B2 | 11/2010 | Frye |
| RE42,012 E | 12/2010 | Deaver et al. |
| 7,850,992 B2 | 12/2010 | Hwang, II |
| 7,854,753 B2 | 12/2010 | Kraft |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Rao |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Visser |
| 8,071,729 B2 | 12/2011 | Giles-Komar et al. |
| 8,075,916 B2 | 12/2011 | Park |
| 8,075,917 B2 | 12/2011 | Park |
| 8,076,317 B2 | 12/2011 | Kulmann |
| 8,076,319 B2 | 12/2011 | Leonard |
| 8,080,553 B2 | 12/2011 | Auspitz |
| 8,088,605 B2 | 1/2012 | Beudet et al. |
| 8,096,940 B2 | 1/2012 | Iverson |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker |
| 8,119,741 B2 | 2/2012 | Pavlin |
| 8,121,886 B2 | 2/2012 | Azar |
| 8,124,118 B2 | 2/2012 | Lennernaes |
| 8,124,595 B2 | 2/2012 | Boissonneault |
| 8,147,561 B2 | 4/2012 | Binmoeller |
| 8,148,546 B2 | 4/2012 | Baasner |
| 8,158,613 B2 | 4/2012 | Staniforth |
| 8,158,614 B2 | 4/2012 | Lambert et al. |
| 8,163,722 B2 | 4/2012 | Savor |
| 8,177,449 B2 | 5/2012 | Watkinson |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Wood, Jr. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Narkunan |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack |
| 8,257,725 B2 | 9/2012 | Cromack |
| 8,268,352 B2 | 9/2012 | Karan |
| 8,268,806 B2 | 9/2012 | Labrie |
| 8,268,878 B2 | 9/2012 | Johnson |
| 8,273,730 B2 | 9/2012 | Fernandez et al. |
| 8,287,888 B2 | 10/2012 | Song et al. |
| 8,288,366 B2 | 10/2012 | Gonzalez |
| 8,318,898 B2 | 11/2012 | Fasel |
| 8,324,193 B2 | 12/2012 | Sepsick |
| 8,329,680 B2 | 12/2012 | Evans et al. |
| 8,337,814 B2 | 12/2012 | Osbakken |
| 8,344,007 B2 | 1/2013 | Chui |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Besonov |
| 8,372,424 B2 | 2/2013 | Berry |
| 8,372,806 B2 | 2/2013 | Bragagna |
| 8,377,482 B2 | 2/2013 | Laurie |
| 8,377,994 B2 | 2/2013 | Drechsler |
| 8,394,759 B2 | 3/2013 | Barathur |
| 8,415,332 B2 | 4/2013 | Reape |
| 8,420,111 B2 | 4/2013 | Hermsmeyer |
| 8,435,561 B2 | 5/2013 | Besins et al. |
| 8,435,972 B2 | 5/2013 | Sayeed |
| 8,449,879 B2 | 5/2013 | Applegate |
| 8,450,108 B2 | 5/2013 | Boyce |
| 8,454,945 B2 | 6/2013 | Narain |
| 8,455,468 B2 | 6/2013 | Kellermann |
| 8,461,138 B2 | 6/2013 | Boissonneault |
| 8,476,252 B2 | 7/2013 | Pickersgill |
| 8,481,488 B2 | 7/2013 | Carter |

(56) References Cited

U.S. PATENT DOCUMENTS

| | | |
|---|---|---|
| 8,486,374 B2 | 7/2013 | Zlatkis |
| 8,486,442 B2 | 7/2013 | Yamaji |
| 8,492,368 B2 | 7/2013 | Lewandowski |
| 8,507,467 B2 | 8/2013 | Ueda |
| 8,512,693 B2 | 8/2013 | Azevedo |
| 8,512,754 B2 | 8/2013 | Needham |
| 8,518,376 B2 | 8/2013 | Schuz |
| 8,536,159 B2 | 9/2013 | Zeng |
| 8,540,967 B2 | 9/2013 | Trivedi |
| 8,541,400 B2 | 9/2013 | Joabsson |
| 8,551,462 B2 | 10/2013 | Marenus |
| 8,551,508 B2 | 10/2013 | Lee et al. |
| 8,557,281 B2 | 10/2013 | Tuominen |
| 8,568,374 B2 | 10/2013 | De Graaff |
| 8,591,951 B2 | 11/2013 | Kohn |
| 8,613,951 B2 | 12/2013 | Troiano |
| 8,633,178 B2 | 1/2014 | Cacace |
| 8,633,180 B2 | 1/2014 | Zeng |
| 8,636,787 B2 | 1/2014 | Sabaria |
| 8,636,982 B2 | 1/2014 | Schuz |
| 8,653,129 B2 | 2/2014 | Fein |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller |
| 8,663,703 B2 | 3/2014 | Moldavski |
| 8,664,207 B2 | 3/2014 | Zheng |
| 8,669,293 B2 | 3/2014 | Sharoni |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Zeng |
| 8,703,105 B2 | 4/2014 | Besonov |
| 8,709,385 B2 | 4/2014 | Schuz |
| 8,709,451 B2 | 4/2014 | Rapoport |
| 8,715,735 B2 | 5/2014 | Funke |
| 8,721,331 B2 | 5/2014 | Raghuprasad |
| 8,722,021 B2 | 5/2014 | Eini |
| 8,734,846 B2 | 5/2014 | Hrkach |
| 8,735,381 B2 | 5/2014 | Podolski |
| 8,741,336 B2 | 6/2014 | Dipierro |
| 8,741,373 B2 | 6/2014 | Rao |
| 8,753,661 B2 | 6/2014 | Gassner |
| 8,784,882 B2 | 7/2014 | Mattern |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,006,222 B2 | 4/2015 | Bernick et al. |
| 9,012,434 B2 | 4/2015 | Bernick et al. |
| 9,114,145 B2 | 8/2015 | Bernick et al. |
| 9,114,146 B2 | 8/2015 | Bernick et al. |
| 9,180,091 B2 | 11/2015 | Bernick et al. |
| 9,248,136 B2 | 2/2016 | Bernick et al. |
| 9,289,382 B2 | 3/2016 | Bernick et al. |
| 9,301,920 B2 | 4/2016 | Bernick et al. |
| 2001/0005728 A1 | 2/2001 | Guittard et al. |
| 2001/0009673 A1 | 7/2001 | Gunther |
| 2001/0021816 A1 | 9/2001 | Caillouette |
| 2001/0023261 A1 | 9/2001 | Ryoo |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2001/0053383 A1 | 12/2001 | Sablotsky |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik |
| 2002/0119198 A1 | 8/2002 | Gao |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Garfield |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman |
| 2003/0003139 A1 | 1/2003 | Gunther |
| 2003/0004145 A1 | 1/2003 | Leonard |
| 2003/0007994 A1 | 1/2003 | Bunt et al. |
| 2003/0027772 A1 | 2/2003 | Breton |
| 2003/0091620 A1 | 2/2003 | Venkateshwaran |
| 2003/0044453 A1 | 3/2003 | Volkel |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1* | 4/2003 | Chen .................... A61K 9/1617 424/400 |
| 2003/0078245 A1 | 4/2003 | Bennink et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Beckmann |
| 2003/0113268 A1 | 6/2003 | Buenafae |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Yoon |
| 2003/0175329 A1 | 9/2003 | Mak |
| 2003/0175333 A1 | 9/2003 | Shefer |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Bernstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Friedman |
| 2003/0225048 A1 | 12/2003 | Friedman |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki |
| 2004/0043043 A1 | 3/2004 | Schlyter |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |

(56) References Cited

U.S. PATENT DOCUMENTS

| | | |
|---|---|---|
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Sciano |
| 2004/0234606 A1 | 11/2004 | Levine et al. |
| 2004/0241219 A1 | 12/2004 | Hille |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Deaver |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Latif |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Paterson |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theoblld |
| 2005/0118272 A1 | 6/2005 | Besse et al. |
| 2005/0129756 A1 | 6/2005 | Podhaisky |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Wuttke |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yuan |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 11/2005 | Jorda et al. |
| 2005/0266088 A1 | 12/2005 | Frijlink |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides |
| 2006/0083778 A1 | 4/2006 | Allison et al. |
| 2006/0084704 A1 | 4/2006 | Shih |
| 2006/0088580 A1 | 4/2006 | Seibertz |
| 2006/0089337 A1 | 4/2006 | Casper et al. |
| 2006/0093678 A1 | 5/2006 | Chickering, III et al. |
| 2006/0100180 A1 | 5/2006 | Bohlmann |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Anyarambhatla |
| 2006/0193789 A1 | 8/2006 | Tamarkin |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Pushpala |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh Bennink |
| 2006/0251581 A1 | 11/2006 | Madenjian |
| 2006/0252049 A1 | 11/2006 | Shuler et al. |
| 2006/0257472 A1 | 11/2006 | Neilsen |
| 2006/0275218 A1 | 12/2006 | Besonov |
| 2006/0275360 A1 | 12/2006 | Ahmed et al. |
| 2006/0276414 A1 | 12/2006 | Coelingh Bennink |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Mc Ilroy |
| 2007/0004693 A1 | 1/2007 | Woolfson et al. |
| 2007/0004694 A1 | 1/2007 | Woolfson et al. |
| 2007/0009559 A1 | 1/2007 | Alosio |
| 2007/0009594 A1 | 1/2007 | Grubb |
| 2007/0010550 A1 | 1/2007 | McKenzie |
| 2007/0014839 A1 | 1/2007 | Bracht |
| 2007/0015698 A1 | 1/2007 | Goldstein |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0037780 A1 | 2/2007 | Anigbogu |
| 2007/0037782 A1 | 2/2007 | Suzuki |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0078091 A1 | 4/2007 | Hubler |
| 2007/0088029 A1 | 4/2007 | Balog et al. |
| 2007/0093548 A1 | 4/2007 | Diffendal et al. |

(56) References Cited

U.S. PATENT DOCUMENTS

| | | |
|---|---|---|
| 2007/0116729 A1 | 5/2007 | Palepu |
| 2007/0116829 A1 | 5/2007 | Prakash et al. |
| 2007/0128263 A1 | 6/2007 | Wall |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson |
| 2007/0190022 A1 | 8/2007 | Chiao |
| 2007/0191319 A1 | 8/2007 | Ke et al. |
| 2007/0196415 A1 | 8/2007 | Houston |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Bernard |
| 2007/0238713 A1 | 10/2007 | Gast et al. |
| 2007/0243229 A1 | 10/2007 | Smith et al. |
| 2007/0248658 A1 | 10/2007 | Bracht |
| 2007/0254858 A1 | 11/2007 | Cronk |
| 2007/0255197 A1 | 11/2007 | Wilkins |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | DeVries et al. |
| 2007/0287688 A1 | 12/2007 | Chan |
| 2007/0287789 A1 | 12/2007 | Jones et al. |
| 2007/0292359 A1 | 12/2007 | Schuz |
| 2007/0292387 A1 | 12/2007 | Jon et al. |
| 2007/0292461 A1 | 12/2007 | Danziger |
| 2007/0292493 A1 | 12/2007 | Brierre |
| 2007/0298089 A1 | 12/2007 | Yoshinaga |
| 2008/0026035 A1 | 1/2008 | Chollet et al. |
| 2008/0026040 A1 | 1/2008 | Guzman |
| 2008/0026062 A1 | 1/2008 | Farr et al. |
| 2008/0038219 A1 | 2/2008 | Carlson |
| 2008/0038350 A1 | 2/2008 | Gerecke et al. |
| 2008/0039405 A1 | 2/2008 | Joseph |
| 2008/0050317 A1 | 2/2008 | Besonov |
| 2008/0051351 A1 | 2/2008 | Ghisalberti |
| 2008/0063607 A1 | 3/2008 | Berman |
| 2008/0069779 A1 | 3/2008 | Schuz |
| 2008/0069791 A1 | 3/2008 | Beissert |
| 2008/0085877 A1 | 4/2008 | Bortz |
| 2008/0095831 A1 | 4/2008 | McGraw |
| 2008/0095838 A1 | 4/2008 | Abou Chacra-Vemet |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Gricenko |
| 2008/0139392 A1 | 6/2008 | Yuan |
| 2008/0145423 A1 | 6/2008 | Khan et al. |
| 2008/0153789 A1 | 6/2008 | Dmowski |
| 2008/0175814 A1 | 7/2008 | Phiasivongsa et al. |
| 2008/0175905 A1 | 7/2008 | Blksh |
| 2008/0175908 A1 | 7/2008 | Blksh |
| 2008/0188829 A1 | 8/2008 | Creasy |
| 2008/0206156 A1 | 8/2008 | Cronk |
| 2008/0206159 A1 | 8/2008 | Schuz |
| 2008/0206161 A1 | 8/2008 | Tamarkin et al. |
| 2008/0214512 A1 | 9/2008 | Seitz |
| 2008/0220069 A1 | 9/2008 | Allison |
| 2008/0226698 A1 | 9/2008 | Beste |
| 2008/0227763 A1 | 9/2008 | Paris |
| 2008/0234199 A1 | 9/2008 | Katamreddy |
| 2008/0234240 A1 | 9/2008 | Duesterberg |
| 2008/0255078 A1 | 10/2008 | Katamreddy |
| 2008/0255089 A1 | 10/2008 | Katamreddy |
| 2008/0261931 A1 | 10/2008 | Stenlof |
| 2008/0113953 A1 | 12/2008 | DeVries et al. |
| 2008/0114050 A1 | 12/2008 | Fensome et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson |
| 2009/0010968 A1 | 1/2009 | Peyrot |
| 2009/0011041 A1 | 1/2009 | Musaeva |
| 2009/0017120 A1 | 1/2009 | Brisco |
| 2009/0022683 A1 | 1/2009 | Park |
| 2009/0047357 A1 | 2/2009 | Tomohira |
| 2009/0053294 A1 | 2/2009 | Prendergast |
| 2009/0060982 A1 | 3/2009 | Ron et al. |
| 2009/0060997 A1 | 3/2009 | Seitz |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Kresevic |
| 2009/0130029 A1 | 5/2009 | Tamarkin |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin |
| 2009/0181088 A1 | 7/2009 | Song et al. |
| 2009/0186081 A1 | 7/2009 | Slot |
| 2009/0197843 A1 | 8/2009 | Notelovitz |
| 2009/0203658 A1 | 8/2009 | Rose |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Kresevic |
| 2009/0325916 A1 | 12/2009 | Zhang et al. |
| 2010/0008985 A1 | 1/2010 | Vermeulen |
| 2010/0028360 A1 | 2/2010 | Atwood |
| 2010/0034838 A1 | 2/2010 | Staniforth |
| 2010/0034880 A1 | 2/2010 | Sintov |
| 2010/0040671 A1 | 2/2010 | Ahmed et al. |
| 2010/0048523 A1 | 2/2010 | Bachman et al. |
| 2010/0055138 A1 | 3/2010 | Jacobs |
| 2010/0074959 A1 | 3/2010 | Hansom et al. |
| 2010/0086501 A1 | 4/2010 | Chang |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Lee |
| 2010/0143481 A1 | 6/2010 | Shenoy |
| 2010/0150993 A1 | 6/2010 | Theobald |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Ziv |
| 2010/0227797 A1 | 9/2010 | Danielsson |
| 2010/0240626 A1 | 9/2010 | Kulkarni et al. |
| 2010/0247482 A1 | 9/2010 | Chen |
| 2010/0247632 A1 | 9/2010 | Dong et al. |
| 2010/0247635 A1 | 9/2010 | Schmidt |
| 2010/0255085 A1 | 10/2010 | Liu et al. |
| 2010/0273730 A1 | 10/2010 | Hsu |
| 2010/0278759 A1 | 11/2010 | Murad |
| 2010/0279988 A1 | 11/2010 | Setiawan |

(56) References Cited

U.S. PATENT DOCUMENTS

| | | |
|---|---|---|
| 2010/0291191 A1 | 11/2010 | Lapitsky |
| 2010/0292199 A1 | 11/2010 | Leverd |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Wilkins |
| 2010/0330168 A1 | 12/2010 | Gicquel et al. |
| 2011/0028439 A1 | 2/2011 | Witt-Enderby et al. |
| 2011/0039814 A1 | 2/2011 | Ross |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland |
| 2011/0091555 A1 | 4/2011 | De Luigi Bruschi et al. |
| 2011/0098258 A1 | 4/2011 | Canet |
| 2011/0098631 A1 | 4/2011 | McIntyre et al. |
| 2011/0104268 A1 | 5/2011 | Segot |
| 2011/0104289 A1 | 5/2011 | Savoir Vilboeuf et al. |
| 2011/0130372 A1 | 6/2011 | Marliani |
| 2011/0135719 A1 | 6/2011 | Besins et al. |
| 2011/0142945 A1 | 6/2011 | Chen |
| 2011/0152840 A1 | 6/2011 | Lee |
| 2011/0158920 A1 | 6/2011 | Fisher |
| 2011/0171140 A1 | 7/2011 | Illum |
| 2011/0182997 A1 | 7/2011 | Lewis et al. |
| 2011/0190201 A1 | 8/2011 | Wood, Jr. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Karabelas |
| 2011/0244043 A1 | 10/2011 | Wang |
| 2011/0250256 A1 | 10/2011 | Hyun Oh |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Volkmann |
| 2011/0281832 A1 | 11/2011 | Wennogle |
| 2011/0287094 A1 | 11/2011 | Penhasi |
| 2011/0293720 A1 | 12/2011 | General et al. |
| 2011/0294738 A1 | 12/2011 | Kuliopulos |
| 2011/0300167 A1 | 12/2011 | Covic |
| 2011/0301087 A1 | 12/2011 | McBride |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi |
| 2012/0028888 A1 | 2/2012 | Janz |
| 2012/0028910 A1 | 2/2012 | Takruri |
| 2012/0028936 A1 | 2/2012 | Popova |
| 2012/0045532 A1 | 2/2012 | Cohen |
| 2012/0046264 A1 | 2/2012 | Lieb |
| 2012/0046518 A1 | 2/2012 | Yoakum |
| 2012/0052077 A1 | 3/2012 | Truitt, III et al. |
| 2012/0058171 A1 | 3/2012 | Zeeman |
| 2012/0058962 A1 | 3/2012 | Sparrow |
| 2012/0058979 A1 | 3/2012 | Auspitz |
| 2012/0064135 A1 | 3/2012 | Harms |
| 2012/0065179 A1 | 3/2012 | Andersson |
| 2012/0065221 A1 | 3/2012 | Babul |
| 2012/0087872 A1 | 4/2012 | Schuz |
| 2012/0101073 A1 | 4/2012 | Mannion |
| 2012/0121517 A1 | 5/2012 | Kim |
| 2012/0121692 A1 | 5/2012 | Fang |
| 2012/0122829 A1 | 5/2012 | Masini |
| 2012/0128625 A1 | 5/2012 | Shalwitz et al. |
| 2012/0128654 A1 | 5/2012 | Terpstra |
| 2012/0128683 A1 | 5/2012 | Shantha |
| 2012/0128733 A1 | 5/2012 | Perrin |
| 2012/0128777 A1 | 5/2012 | Keck et al. |
| 2012/0129773 A1 | 5/2012 | Geier |
| 2012/0129819 A1 | 5/2012 | Vancaillie |
| 2012/0136013 A1 | 5/2012 | Wennogle |
| 2012/0142645 A1 | 6/2012 | Marx |
| 2012/0148670 A1 | 6/2012 | Lee |
| 2012/0149748 A1 | 6/2012 | Shanler et al. |
| 2012/0172343 A1 | 7/2012 | Schuermann |
| 2012/0184515 A1 | 7/2012 | Schwede |
| 2012/0231052 A1 | 9/2012 | Brinton |
| 2012/0232011 A1 | 9/2012 | Kneissel |
| 2012/0232042 A1 | 9/2012 | Krenz |
| 2012/0263679 A1 | 10/2012 | Wallace |
| 2012/0269721 A1 | 10/2012 | Weng et al. |
| 2012/0269878 A2 | 10/2012 | Cantor et al. |
| 2012/0277249 A1 | 11/2012 | Tarrand |
| 2012/0277727 A1 | 11/2012 | Doshi |
| 2012/0283671 A1 | 11/2012 | Shibata et al. |
| 2012/0295911 A1 | 11/2012 | Mannion |
| 2012/0301517 A1 | 11/2012 | Warner |
| 2012/0301538 A1 | 11/2012 | Latere |
| 2012/0302535 A1 | 11/2012 | Caufriez |
| 2012/0316130 A1 | 12/2012 | Hendrix |
| 2012/0316496 A1 | 12/2012 | Horres |
| 2012/0321579 A1 | 12/2012 | Edelson |
| 2012/0322779 A9 | 12/2012 | Voskuhl |
| 2012/0328549 A1 | 12/2012 | Edelson |
| 2012/0329738 A1 | 12/2012 | Liu |
| 2013/0004619 A1 | 1/2013 | Goh |
| 2013/0011342 A1 | 1/2013 | Hazot |
| 2013/0017239 A1 | 1/2013 | Fernandez |
| 2013/0022674 A1 | 1/2013 | Dudley et al. |
| 2013/0023505 A1 | 1/2013 | Garfield |
| 2013/0023823 A1 | 1/2013 | Volland |
| 2013/0028850 A1 | 1/2013 | Hazot |
| 2013/0029947 A1 | 1/2013 | Nachaegari et al. |
| 2013/0029957 A1 | 1/2013 | Venkateshwaran |
| 2013/0045266 A1 | 2/2013 | Kang |
| 2013/0045953 A1 | 2/2013 | Grenier |
| 2013/0059795 A1 | 3/2013 | Lo |
| 2013/0064897 A1 | 3/2013 | Binay |
| 2013/0072466 A1 | 3/2013 | Choi |
| 2013/0084257 A1 | 4/2013 | Ishida |
| 2013/0085123 A1 | 4/2013 | Zhao |
| 2013/0089574 A1 | 4/2013 | Stock |
| 2013/0090318 A1 | 4/2013 | Gainer |
| 2013/0102781 A1 | 4/2013 | Ely |
| 2013/0108551 A1 | 5/2013 | Gruell |
| 2013/0116215 A1 | 5/2013 | Lleo |
| 2013/0116222 A1 | 5/2013 | Altomari |
| 2013/0122051 A1 | 5/2013 | Gullapalli |
| 2013/0123175 A1 | 5/2013 | McKee |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Schmitz |
| 2013/0131028 A1 | 5/2013 | Snyder |
| 2013/0131029 A1 | 5/2013 | Baltussen |
| 2013/0149314 A1 | 6/2013 | Bullerdiek |
| 2013/0164225 A1 | 6/2013 | Besonov |
| 2013/0164346 A1 | 6/2013 | Son |
| 2013/0165744 A1 | 6/2013 | Carson |
| 2013/0178452 A1 | 7/2013 | King |
| 2013/0183254 A1 | 7/2013 | Cochran |
| 2013/0183325 A1 | 7/2013 | Sforzini |
| 2013/0189193 A1 | 7/2013 | Besonov |
| 2013/0189196 A1 | 7/2013 | Tamarkin |
| 2013/0189230 A1 | 7/2013 | Van D Kooy |
| 2013/0189368 A1 | 7/2013 | Mosqueira |
| 2013/0210709 A1 | 8/2013 | Covic |
| 2013/0216550 A1 | 8/2013 | Penninger |
| 2013/0216596 A1 | 8/2013 | Fernandez |
| 2013/0224177 A1 | 8/2013 | Kim |
| 2013/0224257 A1 | 8/2013 | Sah |
| 2013/0224268 A1 | 8/2013 | Jaikaria |

(56) References Cited

U.S. PATENT DOCUMENTS

| | | |
|---|---|---|
| 2013/0224300 A1 | 8/2013 | Maggio |
| 2013/0225412 A1 | 8/2013 | Sardari Lodriche |
| 2013/0225542 A1 | 8/2013 | Frick |
| 2013/0226113 A1 | 8/2013 | Langguth |
| 2013/0243696 A1 | 9/2013 | Wang |
| 2013/0245253 A1 | 9/2013 | Mook |
| 2013/0245570 A1 | 9/2013 | Jackson |
| 2013/0261096 A1 | 10/2013 | Merian |
| 2013/0266645 A1 | 10/2013 | Schoenecker |
| 2013/0267485 A1 | 10/2013 | Da Silva Maia Filho |
| 2013/0273167 A1 | 10/2013 | Kim |
| 2013/0274211 A1 | 10/2013 | Prusthy |
| 2013/0280213 A1 | 10/2013 | Voskuhl |
| 2013/0316374 A1 | 11/2013 | Menon |
| 2013/0317065 A1 | 11/2013 | Seto |
| 2013/0317315 A1 | 11/2013 | Tsang |
| 2013/0324565 A1 | 12/2013 | Zhao |
| 2013/0331363 A1 | 12/2013 | Zhao |
| 2013/0338122 A1 | 12/2013 | Bernick et al. |
| 2013/0338123 A1 | 12/2013 | Bernick et al. |
| 2013/0338124 A1 | 12/2013 | Zhao |
| 2013/0345187 A1 | 12/2013 | Rodriguez Oquendo |
| 2014/0018335 A1 | 1/2014 | Seto |
| 2014/0024590 A1 | 1/2014 | Taylor |
| 2014/0031289 A1 | 1/2014 | Kim |
| 2014/0031323 A1 | 1/2014 | Perez |
| 2014/0066416 A1 | 3/2014 | Leunis |
| 2014/0072531 A1 | 3/2014 | Oh |
| 2014/0079686 A1 | 3/2014 | Prouty |
| 2014/0088051 A1 | 3/2014 | Bernick et al. |
| 2014/0088058 A1 | 3/2014 | Maurizio |
| 2014/0088059 A1 | 3/2014 | Santha |
| 2014/0094426 A1 | 4/2014 | Drummond |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Cacace |
| 2014/0113889 A1 | 4/2014 | Haine |
| 2014/0127185 A1 | 5/2014 | Sayeed |
| 2014/0127280 A1 | 5/2014 | Jukarainen |
| 2014/0127308 A1 | 5/2014 | Opara |
| 2014/0128798 A1 | 5/2014 | Malanchin |
| 2014/0148491 A1 | 5/2014 | Valia et al. |
| 2014/0186332 A1 | 7/2014 | Ezrin |
| 2014/0187487 A1 | 7/2014 | Shoichet |
| 2014/0193523 A1 | 7/2014 | Henry |
| 2014/0194396 A1 | 7/2014 | Wennogle |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |

FOREIGN PATENT DOCUMENTS

| | | | |
|---|---|---|---|
| CN | 102258455 | A | 11/2011 |
| EP | 0275716 | A1 | 7/1988 |
| EP | 0279977 | A2 | 8/1988 |
| EP | 0622075 | A1 | 11/1994 |
| EP | 0785211 | A1 | 7/1997 |
| EP | 0785212 | A1 | 7/1997 |
| EP | 0811381 | A1 | 12/1997 |
| EP | 0904064 | A1 | 3/1999 |
| EP | 1094781 | B1 | 7/2008 |
| EP | 2191833 | A1 | 6/2010 |
| GB | 452238 | A | 8/1936 |
| GB | 720561 | A | 12/1954 |
| GB | 848881 | A | 9/1960 |
| GB | 874368 | A | 8/1961 |
| GB | 1589946 | A | 5/1981 |
| IN | 2005KOL00053 | | 8/2005 |
| IN | 216026 | | 3/2008 |
| IN | 244217 | | 11/2010 |
| JP | H4-503810 | | 9/1990 |
| JP | H2-264725 | A | 10/1990 |
| WO | 1990011064 | | 10/1990 |
| WO | 1993017686 | | 9/1993 |
| WO | 1994022426 | | 10/1994 |
| WO | 1995030409 | | 11/1995 |
| WO | 1996009826 | | 4/1996 |
| WO | 1996019975 | | 7/1996 |
| WO | 1996030000 | | 10/1996 |
| WO | 1997005491 | | 2/1997 |
| WO | 1997043989 | | 11/1997 |
| WO | 1998010293 | | 3/1998 |
| WO | 1998032465 | | 7/1998 |
| WO | 1998051280 | | 11/1998 |
| WO | 1999022680 | A1 | 5/1999 |
| WO | 1999032072 | | 7/1999 |
| WO | 1999039700 | | 8/1999 |
| WO | 1999042109 | | 8/1999 |
| WO | 1999043304 | | 9/1999 |
| WO | 1999048477 | | 9/1999 |
| WO | 1999053910 | | 10/1999 |
| WO | 1999062497 | A1 | 12/1999 |
| WO | 1999063974 | | 12/1999 |
| WO | 2000001351 | | 1/2000 |
| WO | 2000006175 | | 2/2000 |
| WO | 2000038659 | | 6/2000 |
| WO | 2000045795 | | 8/2000 |
| WO | 2000050007 | | 8/2000 |
| WO | 2000059577 | | 10/2000 |
| WO | 2000076522 | | 12/2000 |
| WO | 2001037808 | | 5/2001 |
| WO | 2001054699 | | 8/2001 |
| WO | 2001060325 | | 8/2001 |
| WO | 2001087276 | | 11/2001 |
| WO | 2001091757 | | 12/2001 |
| WO | 2002007700 | | 1/2002 |
| WO | 2002011768 | | 2/2002 |
| WO | 2002022132 | | 3/2002 |
| WO | 2002040008 | | 5/2002 |
| WO | 2002041878 | | 5/2002 |
| WO | 2002053131 | | 7/2002 |
| WO | 2002078602 | | 10/2002 |
| WO | 2002078604 | | 10/2002 |
| WO | 2003028667 | | 4/2003 |
| WO | 2003041718 | | 5/2003 |
| WO | 2003041741 | | 5/2003 |
| WO | 2003068186 | | 8/2003 |
| WO | 2003077923 | | 9/2003 |
| WO | 2003082254 | | 10/2003 |
| WO | 2003092588 | | 11/2003 |
| WO | 2004014397 | A1 | 2/2004 |
| WO | 2004014432 | | 2/2004 |
| WO | 2004017983 | | 3/2004 |
| WO | 2004032897 | | 4/2004 |
| WO | 2004052336 | | 6/2004 |

(56) References Cited

FOREIGN PATENT DOCUMENTS

| | | |
|---|---|---|
| WO | 2004054540 | 7/2004 |
| WO | 2004080413 | 9/2004 |
| WO | 2004110408 A2 | 12/2004 |
| WO | 2005027911 | 3/2005 |
| WO | 2005030175 | 4/2005 |
| WO | 2007076144 A2 | 7/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013078422 A2 | 5/2013 |
| WO | 2013088254 | 6/2013 |
| WO | 2013102665 A1 | 7/2013 |
| WO | 2013106437 A1 | 7/2013 |
| WO | 2013112947 A1 | 8/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |
| WO | 2015179782 A1 | 11/2015 |
| WO | 2016018993 A1 | 2/2016 |

OTHER PUBLICATIONS

U.S. Appl. No. 14/099,545, filed Dec. 6, 2013, U.S Pat. No. 8,846,648, Sep. 30, 2014.
U.S. Appl. No. 14/099,562, filed Dec. 6, 2013, U.S. Pat. No. 8,987,237, Mar. 24, 2015.
U.S. Appl. No. 14/099,571, filed Dec. 6, 2013, U.S. Pat. No. 8,846,649, Sep. 30, 2014.
U.S. Appl. No. 14/099,582, filed Dec. 6, 2013, U.S. Pat. No. 9,012,434, Apr. 21, 2015.
U.S. Appl. No. 14/099,598, filed Dec. 6, 2013, U.S. Pat. No. 8,987,238, Mar. 24, 2015.
U.S. Appl. No. 14/099,612, filed Dec. 6, 2013, U.S. Pat. No. 8,933,059, Jan. 13, 2015.
U.S. Appl. No. 14/099,623, filed Dec. 6, 2013, U.S. Pat. No. 9,006,222, Apr. 14, 2015.
U.S. Appl. No. 14/106,655, filed Dec. 13, 2013.
U.S. Appl. No. 14/125,554, filed Jan. 25, 2013, U.S. Pat. No. 9,248,136, Feb. 2, 2016.
U.S. Appl. No. 14/136,048, filed Dec. 20, 2013, U.S. Pat. No. 9,180,091, Nov. 10, 2015.
U.S. Appl. No. 14/475,814, filed Sep. 3, 2014, U.S. Pat. No. 8,993,548, Mar. 31, 2015.
U.S. Appl. No. 14/475,864, filed Sep. 3, 2014, U.S. Pat. No. 8,993,549, Mar. 31, 2015.
U.S. Appl. No. 14/475,946, filed Sep. 3, 2014, U.S. Pat. No. 9,114,145, Aug. 25, 2015.
U.S. Appl. No. 14/476,040, filed Sep. 3, 2014, U.S. Pat. No. 9,114,146, Aug. 25, 2015.
U.S. Appl. No. 14/512,046, filed Oct. 10, 2014.
U.S. Appl. No. 14/521,002, filed Oct. 22, 2014.
U.S. Appl. No. 14/521,230, filed Oct. 22, 2014.
U.S. Appl. No. 14/624,051, filed Feb. 17, 2015, U.S. Pat. No. 9,289,382, Mar. 22, 2016.
U.S. Appl. No. 14/649,818, filed Jun. 18, 2013.
U.S. Appl. No. 14/690,913, filed Apr. 20, 2015.
U.S. Appl. No. 14/690,955, filed Apr. 20, 2015.
U.S. Appl. No. 14/812,179, filed Jul. 29, 2015.
U.S. Appl. No. 14/830,398, filed Aug. 19, 2015.
U.S. Appl. No. 15/090,493, filed Apr. 4, 2016.
U.S. Appl. No. 15/372,385, filed Dec. 7, 2016.
U.S. Appl. No. 15/420,019, filed Jan. 30, 2017.
U.S. Appl. No. 15/475,052, filed Mar. 30, 2017.

(56) References Cited

OTHER PUBLICATIONS

U.S. Appl. No. 15/475,068, filed Mar. 30, 2017.
U.S. Appl. No. 15/832,750, filed Dec. 5, 2017.
U.S. Appl. No. 15/832,757, filed Dec. 5, 2017.
U.S. Appl. No. 15/893,542, filed Feb. 9, 2018.
U.S. Appl. No. 15/893,546, filed Feb. 9, 2018.
U.S. Appl. No. 15/893,550, filed Feb. 9, 2018.
Abbas et al., Regression of endometrial implants treated with vitamin D3 in a rat model of endometriosis, European J of Pharma, 715 (2013) 72-75, Elsevier.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Abitec, Excipients for the Pharmaceutical Industry—Regulatory and Product Information, 2013, 2 pages.
Acarturk, Fusun, Mucoadhesive Vaginal Drug Delivery System, Recent Patents on Drug Delivery & Formulation, 2009, vol. 3, pp. 193-195.
Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
Alvarez et al., Ectopic uterine tissue as a chronic pain generator, Neuroscience, Dec. 6, 2012, 225: 269-272.
Application Note FT-IR: JI-Ap-FT0508-008, CD spectra of pharmaceuticals substances—Steroids (2), JASCO International Co., Ltd., 2 pages.
Araya-Siblja et al., Crystallization of progesterone polymorphs using polymer-induced heteronucleation (PIHn) method, Drug Development and Industrial Pharmacy, Early Online, pp. 1-8, 2014, Informa Healthcare.
Araya-Siblja, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Siblja, Andrea Manela, et al., Chemical Properties of Progesterone Selected Refer., SciFinder, 2014, American Chemical Society & US Natl. Lib. of Med.
Araya-Siblja, Andrea Manela, et al., Polymorphism in Progesterone Selected References, SciFinder, Feb. 24, 2014, pp. 1-12, American Chem. Society & Natl. Lib. of Med.
Araya-Siblja, Andrea Manela, et al., Polymorphism in Progesterone, SciFinder, pp. 1-46, Feb. 24, 2014, American Chem. Society & Natl. Lib. of Med.
Archer et al., Effects of ospemifene on the female reproductive and urinary tracts: translation from preclinical models into clinical evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.
Azure Pharma, Inc., ELESTRIN™—Estradiol Gel, Drug Info, http://dailymed.nlm.nih.gov/dailymed/archives/fdaDrugInfo.cfm?archiveid=11885, 26 pages, Aug. 2009.

Bakhmutova-Albert, Ekaterina, et al., Enhancing Aqueous Dissolution Rates of Progesterone via Cocrystallization, SSCI, Division of Aptuit, Poster No. R6247, West Lafayette.
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bartosova, Transdermal Drug Delivery In Vitro Using Diffusion Cells, Current Medicinal Chemistry, 2012, 19, 4671-4677, Bentham Science Publishers.
Benbow et al., Distribution and Metabolism of Maternal Progesterone in the Uterus, Placenta, and Fetus during Rat Pregnancy, Biology of Reproduction 52, 1327-1333 (1995).
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani Bhagu R. et al., "Misconception and Concerns about Bioidentical Hormones Used for Custom-Compounded Hormone Therapy," J Clin Endocrinol Metab, Mar. 2012, 97(3):756-759.
Bhavnani et al., Structure Activity Relationships and Differential Interactions and Functional Activity of Various Equine Estrogens Mediated via Estrogen Receptors (ERs) ERα and ERβ, Endocrinology, Oct. 2008, 149(10):4857-4870.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
British Pharmacocopoeia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.
Castelo-Branco Camil et al., "Treatment of atrophic vaaginitis," Therapy, 2007, vol. 4, No. 3, pp. 349-353.
Cendejas-Santana, G, et al., Growth and characterization of progesterone crystallites, Revista Mexicana de Fisica, 50, Suplemento 1 pp. 1-3, 2004.
Chambin et al., Interest of Multifunctional Lipid Excipients: Case of Gelucire® 44/14, Drug Development and Industrial Pharmacy, vol. 31, No. 6, pp. 527-534 (Year: 2005).
ChemPro, Top-Notch Technology in Production of Oils and Fats, Chempro-Edible-Oil-Refining-ISO-TUV-Austria.
Cho, Y.A. et al., Transdermal Delivery of Ketorolac Tromethamine: Effects of Vehicles and Penetration Enhancers, Drug Development and Industrial Pharmacy, 30(6):557-564, Jun. 2004.
Christen et al., Phase I/Pharmacokinetic Study of High-Dose Progesterone and Doxorubicin, J Clin Oncol 11:2417-2426, 1993.

(56) References Cited

OTHER PUBLICATIONS

Christensson et al., Limonene hydroperoxide analogues differ in allergenic activity, Contact Dermatitis 2008: 59: 344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance , Contact Dermatitis, 71, 264-272, 2014.
Chun et al., Transdermal Delivery of Estradiol and Norethrindrone Acetate: Effect of Vehicles . . . , J. Kor. Pharm. Sci., vol. 35, No. 3, pp. 173-177 (2005).
Cicinelli et al., Direct Transport of Progesterone From Vagina to Uterus, Obstetrics & Gynecology, vol. 95, No. 3, March 2000, pp. 403-406.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Committee Opinion, Incidentally Detected Short Cervical Length, Committee of Obstetric Practice, Obstetrics & Gynecology, ACOG, vol. 119, No. 4, Apr. 2012, pp. 879-882.
Commodari, Fernando, Comparison of 17β-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998.
Corbett et al., "Trends in Pharmacy Compounding for Women's Health in North Carolina: Focus on Vulvodynia," Southern Medical Journal, vol. 107, No. 7, Jul. 2014, pp. 433-436.
Corn Refiners Association, Corn Oil, 5th Edition, Washington, D.C., 2006.
Crandall, Carolyn, "Vaginal Estrogen Preparations: A Review of Safety and Efficacy for Vaginal Atrophy," Journal of Women's Health, 2002, vol. 11, No. 10, pp. 857-877.
CREMER Care, ""MIGLYOL® 810, 812 INCI: Caprylic/Capric Triglyceride,"" CREMER OLEO GmbH & Co. KG, pp. 1-7, available at http://s3.amazonaws.com/petercremerna/products/spec_sheets/159/339/301 /originai/MIGL YOL_81 0_812_ TDS.pdf? 1389204445 (Mar. 2013) accessed on Dec. 30, 2016.
Critchley et al., Estrogen Receptor β, But Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.
Dauqan, Eqbal M. A., et al., Fatty Acids Composition of Four Different Vegetable Oils (Red Palm Olein, Palm Olein, Corn Oil, IPCBEE, vol. 14, 2011, IACSIT Press, Singapore.
Dideberg, O, et al., Crystal data on progesterone (C21H30O2), desoxycorticosterone (C21H30O3), corticosterone (C21H30O4) and aldosterone . . . , J. Appl. Cryst. vol. 4 pp. 80, 1971.
Diramio, Jackie A., Polyethylene Glycol Methacrylate/Dimetacrylate Hydrogels for Controlled Release of Hydrophobic Drugs, Masters of Science Thesis, University of Georgia, Athens, Georgia, 2002, 131 pages.
Drakulic, Branko J, Role of complexes formation between drugs and penetration enhancers in transdermal . . . , Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of The North American Menopause Society, 2013, vol. 20, No. 11, pp. 1-7.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Engelhardt et al., Conceptus Influences the Distribution of Uterine Leukocytes During Early Porcine Pregnancy, Biology of Reproduction 66, 1875-1880 (2002).
Estradiol, The Merck Index Online, Royal Society of Chemistry, https://www.rsc.org/Merck-Index/monograph/mono1500003758/estradiol?q=unauthorize.
Ettinger et al., Comparison of endometrial growth produced by unopposed conjugated estrogens or by micronized estradiol in postmenopausal women, Am J Obstet Gynecol 1997; 176:112-117.
Excipients for Pharmaceuticals, SASOL OLEFINS & SURFACTANTS GMBH, 2010, 28 pages.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Ferrari, Roseli AP., et al., Oxidative Stability of Biodiesel From Soybean Oil Fatty Acid Ethyl Esters, Sci. Agric., vol. 62(3), pp. 291-295, 2005, PiracicaB1, Braz.
Filipsson et al., Concise International Chemical Assessment Document 5: Limonene, first draft, World Health Organization, Geneva, 1998, 36 pages.
Final Report on the Safety Assessment of BHT, International Journal of Toxicology, 21(Suppl. 2):19-94, 2002/.
Flyvholm, Sensitizing risk of butylated hydroxytoluene B1sed on exposure and effect data, Contact Dermatitis 1990: 23: 341-345.
Fotherby, K., Bioavailability of Orally Administered Sex Steroids Used in Oral Contraception and Hormone Replacement Therapy, Contraception, 1996; 54:59-69.
Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Freedman, R.R., Menopausal hot flashes: Mechanisms, endocrinology, treatment, J. Steroid Biochem. Mol. Biol.(2013), Elsevier.
Fuchs et al., The Effects of an Estrogen and Glycolic Acid Cream on the Facial Skin of Postmenopausal Women: A Randomized Histologic Study, Cutis. Jun. 2003;71(6):481-8.
Fugh-Berman, Adriane, Bioidentical Hormones for Menopausal Hormone Therapy: Variation on a Theme, Journal of General Internal Medicine, vol. 22, pp. 1030-1034, 2007.
Furness et al., Hormone therapy in postmenopausal women and risk of endometrial hyperplasia (Review), 2012, pp. 1-204, The Cochrane Collaboration. Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Garad S. et al., "Preclinical Development for Suspensions," A.K. Kulshreshtha et al. (eds.), *Pharmaceutical Suspensions: From Formulation Development to Manufacturing*, Springer, New York 2010, pp. 127-176.
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-NonInvasive-Deliv-5.aspx#.

(56) References Cited

OTHER PUBLICATIONS

Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.

Gillet et al., Induction of amenorrhea during hormone replacement therapy: optimal micronized progesterone dose. A multicenter study, Maturitas 19 (1994) 103-115.

Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.

Giron-Forest, D, Thermal analysis and calorimetric methods in the characterisation of polymorphs and solvates, Thermochimica Acta, vol. 248 pp. 1-59, 1995, Elsevier.

Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.

Golatowski et al., Comparative evaluation of saliva collection methods for proteome analysis, Clinica Chimica Acta 419 (2013) 42-46.

Graham et al, Physiological Action of Progesterone in Target Tissues, Endocrine Reviews, 1997, vol. 18, No. 4, pp. 502-519.

Groothuis et al., Estrogen and the endometrium: lessons learned from gene expression profiling in rodents and human, Human Reproduction Update, vol. 13, No. 4 pp. 405-417, 2007.

Gunstone, Frank D, et al., Vegetable Oils in Food Technology: Composition, Properties and Uses, Blackwell Publishing, CRC Press, 2002.

Gurney, E.P. et al., The Women's Health Initiative trial and related studies: 10 years later: A clinician's view, J.Steroid Biochem. Mol. Biol. (2013), Elsevier.

Hamid et al., The effects of common solubilizing agents on the intestinal membrane B1rrier functions and membrane toxicity in rats, International Journal of Pharmaceutics 379 (2009) 100-108, Elsevier.

Haner, Barbara, Crystal data (I) for some pregnenes and pregnadienes, Acta Cryst., vol. 17 pp. 1610, 1964.

Hapgood, J.P., et al., Potency of progestogens used in hormonal therapy: Toward understanding differential actions, J. Steroid Biochem. Mol. Biol. (2013), Elsevier.

Hargrove et al., Menopausal Hormone Replacement Therapy with Continuous Daily Oral Micronize Estradiol and Progesterone, Obstet Gynecol, vol. 73, No. 4, Apr. 1989, pp. 606-612.

Hatton et al., "Safety and efficacy of a lipid emulsion containing medium-chain triglycerides," Clinical Pharmacy, 1990, vol. 9, No. 5, pp. 366-371.

He et al., Apoptotic Signaling Pathways in Uteri of Rats with Endometrial Hyperplasia Induced by Ovariectomy Combined with Estrogen, Gynecol Obstet Invest 2013;76:51-56.

Helbling, Ignacio M, et al., The Optimization of an Intravaginal Ring Releasing Progesterone Using a Mathematical Model, Pharm Res, vol. 31 pp. 795-808, 2014, Springer Science.

Helmy et al., Estrogenic Effect of Soy Phytoestrogens on the Uterus of Ovariectomized Female Rats, Clinic Pharmacol Biopharmaceut, 2014, S2, 7 pages.

Henderson, V.W., Alzheimer's disease: Review of hormone therapy trials and implications for treatment and prevention after . . . , J. Steroid Biochem. Mol. Biol. (2013), Elsevier.

Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.

Herman, Aima et al., "Essential oils and their constituents as skin penetration enhancer for transdermal drug delivery: a review," 2014 Royal Pharmaceutical Society, Journal of Pharmacy and Pharmacology, pp. 1-13.

Hodis, H.N., Mack, W.J., Hormone replacement therapy and the association with heart disease and overall mortality: Clinical . . . , J. Steroid Biochem. Mol. Biol. (2013), Elsevier.

Holm et al., "Examination of oral absorption and lymphatic transport of halofantrine in a triple-cannulated canine model after administration in self-microemulsifying drug delivery systems (SMEDDS) containing structured triglycerides," European Journal of Pharmaceutical Sciences 20 (2003) 91-97.

Hospital, Michel, et al., X-ray Crystallography of Estrogens and Their Binding to Receptor Sites, Mol. Pharmacology, vol. 8 pp. 438-445, Acedemic Press, Inc., 1972.

Hostynek, JJ, Predictinga bsorptiono f fragrancec hemicalst hrough human skin, j. Soc.C osmeCt. hem.,4 6, 221-229 (Jul./Aug. 1 995).

Hulsmann, Stefan, Stability of Extruded 17B-Estradiol Solid Dispersions, Pharmaceutical Development and Tech., vol. 6(2) pp. 223-229, 2001, Marcel Dekker, Inc.

Humberstone, Andrew et al., "Lipid-based vehicles for the oral delivery of poorly water soluble drugs," Advanced Drug Delivery Reviews, 25 (1997) 103-128.

Hurn et al., Estrogen as a Neuroprotectant in Stroke, Journal of Cerebral Blood Flow and Metabolism 20:631-652, 2000, Lippincott Williams & Wilkins, Inc., Philadelphia.

Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.

Idder, Salima, et al., Physicochemical properties of Progesterone, SciFinder, pp. 1-26, Feb. 24, 2014, American Chem. Society & US Natl. Lib. of Med.

Johanson, Gunnar, Toxicity Review of Ethylene Glycol Monomethyl Ether and its Acetate Ester, Critical Reviews in Toxicology, 2000, vol. 30, No. 3 , pp. 307-345 (abstract only). http://informahealthcare.com/doi/abs/a0.1080/10408440091159220.

Johnson, William S, et al., Racemic Progesterone, Tetrahedron Letters No. 4, pp. 193-196, 1963, Pergamon Press Ltd., Great Britain.

Joshi et al., Detection and synthesis of a progestagen-dependent protein in human endometrium, J Reprod Fert (1980) 59, 273-285.

Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.

Karande, et al. Enhancement of transdermal drug delivery via synergistic action of chemicals, Biochimica et Biophysica Acta, 1788:2362-2373, Sep. 2009.

Karlberg et al., Air oxidation of d-limonene (the citrus solvent) creates potent allergens, Contact Dermatitis, 1992: 26: 332-340.

Karlberg et al., Influence of an anti-oxidant on the formation of allergenic compounds during auto-oxication of d-limonene, Ann. Occup. Hyg., vol. 38, No. 2, pp. 199-207, 1994.

Kaunitz, Andrew M., Extended duration use of menopausal hormone therapy, Menopause: The Journal of the North American Menopause Society, 2014, vol. 21, No. 6, pp. 1-3.

Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.

Kharode et al., The Pairing of a Selective Estrogen Receptor Modulator, B1zedoxifene, with Conjugated Estrogens as a New Paradigm for the Treatment of Menopausal Symptoms and Osteoporosis Prevention, Endocrinology 149(12):6084-6091, 2008.

Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.

Kincl et al., Increasing Oral Bioavailability of Progesterone by Formulation, Journal of Steroid Biochemistry, 1978, vol. 9, pp. 83-84.

Knuth et al., Hydrogel delivery systems for vaginal and oral applications: Formulation and biological considerations, Advanced Drug Delivery Reviews, vol. 11, No. 1-2, Jul.-Aug. 1993, pp. 137-167 (abstract only).

Koga et al., Enhancing mechanism of Labrasol on intestinal membrane permeability of the hydrophilic drug gentamicin sulfate, European Journal of Pharmaceutics and Biopharmaceutics 64 (2006) 82-91.

(56) References Cited

OTHER PUBLICATIONS

Komm et al., B1zedoxifene Acetate: A Selective Estrogen Receptor Modulator with Improved Selectivity, Endocrinology 146(9):3999-4008, 2005.

Korkmaz, Filiz, Byophysical Studies of Progesterone-Model Membrane Interactions, Thesis, Grad. School of Nat. and App. Sci. of the Middle East Tech. University, Sep. 2003.

Kotiyan, P.N., Stability indicating HPTLC method for the estimation of estradiol, Journal of Pharmaceutical and Biomedical Analysis, vol. 22 pp. 667-671, 2000, Elsevier.

Krzyminiewski, R, et al., EPR Study of the Stable Radical in a y-Irradiated Single Crystal of Progesterone, Jour. of Mag. Resonance, vol. 46 pp. 300-305, 1982, Acedemic Press.

Kubli-Garfias, C, et al., Ab initio calculations of the electronic structure of glucocorticoids, Jour. of Mol. Structure, Theochem, vol. 454 pp. 267-275, 1998, Elsevier.

Kubli-Garfias, Carlos, Ab initio study of the electronic structure of progesterone and related progestins, Jour. of Mol. Structure, Theochem vol. 425, pp. 171-179, 1998, Elsevier (abstract only).

Kuhnert-Brandstaetter and Grimm. Zur Unterscheidung von losungsmittelhaltigen pseudopolymorphen Kristallformen und polymorphen Modifikationen bei Steroidhormonen.II, Mikrochimica Acta, vol. 1, pp. 127-139, 1968.

Kuhnert-Brandstaetter and Junger and Kofler. Thermo-microscopic and spectrophotometric: Determination of steroid hormones, Microchemical Journal 9, pp. 105-133, 1965.

Kuhnert-Brandstaetter and Kofler. Zur mikroskopischen Identitatsprufung und zur Polymorphie der Sexualhormone, Mikrochimica Acta, vol. 6, pp. 847-853, 1959.

Kuhnert-Brandstaetter and Linder. Zur Hydratbildung bei Steroidhormonen, Sci. Pharm, vol. 41(2), pp. 109-116, 1973.

Kumasaka et al., Effects of Various Forms of Progestin on the the Estrogen-Primed, Ovariectomized Rat, Endocrine Journal 1994, 41(2), 161-169.

Kuon et al., A Novel Optical Method to Assess Cervical Changes during Pregnancy and Use to Evaluate the Effects of Progestins on Term and Preterm Labor, Am J Obstet Gynecol. Jul. 2011 ; 205(1): 82.e15-82.e20.

Kuon et al., Actions of progestins for the inhibition of cervical ripening and uterine contractions to prevent preterm birth, FVV in OBGYN, 2012, 4 (2): 110-119.

Kuon et al., Pharmacological actions of progestins to inhibit cervical ripening and prevent delivery depend upon their properties, the route of administration and the vehicle, Am J Obstet Gynecol. May 2010 ; 202(5): 455.e1-455.e9.

Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.

Lacey, J.V. Jr., The WHI ten year's later: An epidemiologist's view, J. Steroid Biochem. Mol. Biol. (2013), Elsevier.

Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.

Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.

Land, Laura M, The influence of water content of triglyceride oils on the solubility of steriods, Pharmaceutical Research, vol. 22(5) May 2005, Springer Science+Business Media.

Lane, Majella E., "Skin penetration enhancers," International Journal of Pharmaceutics 447 (2013) 12-21.

Lauer et al., "Evaluation of the hairless rat as a model for in vivo percutaneous absorption," Journal of Pharmaceutical Sciences, vol. 86, No. 1, Jan. 1997, pp. 13-18.

Leonetti et al., Transdermal progesterone cream as an alternative progestin in hormone therapy, Alternative Therapies, Nov./Dec. 2005, vol. 11, No. 6, pp. 36-38.

Leonetti, Helene B, et al., Topical progesterone cream has an antiproliferative effect on estrogen-stimulated endometrium, Fertility and Sterility, vol. 79(1), Jan. 2003.

Lewis, John G. et al., Caution on the use of saliva measurements to monitor absorption of progesterone from transdermal creams in postmenopausal women, Maturitas, The European Menopause Journal, vol. 41, pp. 1-6, 2002.

Li, Guo-Chian, Solid-state NMR analysis of steroidal conformation of 17a- and 17B-estradiol in the absence and presence of lipi . . . , Steroids, Elsevier, vol. 77, pp. 185-192, 2012.

Lindmark, Tuulikki et al., "Absorption Enhancement through Intracellular Regulation of Tight Junction Permeability by Medium Chain Fatty Acids in Caco-2 Cells," JPET 284(1):362-369, 1998.

Lindmark, Tuulikki et al., "Mechanisms of Absorption Enhancement by Medium Chain Fatty Acids in Intestinal Epithelial Caco-2 Cell Monolayers," JPET 275(2):958-964, 1995.

Lobo, R.A., Foreword, J. Steroid Biochem. Mol. Biol. (2014), Elsevier.

Lopes, Luciana B. et al., Enhancement of transdermal delivery of progesterone using medium-chain mono and diglycerides as skin penetration enhancers, Pharmaceutical Development and Technology, 14:5, 524-529, Mar. 2009.

López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.

Lucy et al., Gonadotropin-releasing hormone at estrus: lutenizing hormone, estradiol, and progesterone during . . . Biol Reprod Sep. 1986;35(2):300-311 (abstract only).

Lvova, M. SH., et al., Thermal Analysis in the Quality Control and Standardization of Some Drugs, J Thermal Anal., vol. 40 pp. 405-411, 1993, Wiley.

Mac Bride, Maire B. et al., "Vulvovaginal Atrophy," Mayo Clin Proc, Jan. 2010, 85(1):87-94.

Madishetti et al., Development of domperidone bilayered matrix type transdermal patches: physicochemical, in vitro and ex vivo characterization, DARU vol. 18, No. 3, 2010, pp. 221-229.

Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.

Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.

McGuffy, Irena, Softgel Technology as a Lipid-B1sed Delivery Tool for Bioavailability Enhancement, Catalent Pharma Solutions, Somerset, NJ, Mar. 2011.

Mesley, R.J., Clathrate Formation from Steroids, Chemistry and Industry, vol. 37 pp. 1594-1595, Sep. 1965.

Miao, Wenbin, et al., Chemical Properties of Progesterone, SciFinder, 2014, American Chemical Society & US Natl. Lib. of Med.

Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.

Miller et al., Safety and Feasibility of Topical Application of Limonene as a Massage Oil to the Breast, Journal of Cancer Therapy, 2012, 3, 749-754.

Monti, D. et al., Effect of different terpene-containing essential oils on permeation of estradiol through hairless mouse skin, International Journal of Pharmaceutics, 237:209-24, 2002.

Mueck, A.O. et al., Genomic and non-genomic actions of progestogens in the breast, J. Steroid Biochem. Mol.Biol. (2013), Elsevier.

Muramatsu, Mitsuo, Thermodynamic Relationship between a- and B- Forms of Crystalline Progesterone, J. Pharmaceutical Sciences, vol. 68(2) pp. 175-178, 1979, Amer. Pharm. Assoc.

Ng, Jo-Han et al., Advances in biodiesel fuel for application in compression ignition engines, Clean Techn Environ Policy, vol. 12, pp. 459-493, 2010, Springer-Verlag.

Nicklas, Martina, Preparation and characterization of marine sponge collagen nanoparticles and employment for the trans . . . , Drug Devel. & Indust. Pharmacy,35(9) pp. 1035, 2009.

(56) References Cited

OTHER PUBLICATIONS

Nilsson et al., Analysis of Contact Allergenic Compounds in Oxidized d-Limonene, Chromatographia vol. 42, No. 3/4, Feb. 1996, pp. 199-205.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
NuGen, What is NuGen HP Hair Growth System.
NuGest900, NuGest 900™.
O'Leary, Peter, Salivary, but not serum or urinary levels of progesterone are elevated after topical application of pregersterone cream to pre-and post-menopausal women, Clinical Endocrinology, vol. 53 pp. 615-620, Blackwell Science 2000.
Opinion on the Diethylene Glycol Momoethyl Ether (DEGEE), Scientific Committee on Consumer Products, Dec. 19, 2006, 27 pages.
Outterson, K., The Drug Quality and Security Act—Mind the Gaps, n engl j med 370;2 nejm.org Jan. 9, 2014, pp. 97-99.
Palamakula et al., Preparation and In Vitro Characterization of Self-Nanoemulsified Drug Delivery Systems of Coenzyme Q10 Using Chiral Essential Oil Components, Pharmaceutical Technology Oct. 2004, pp. 74-88.
Panay et al., The 2013 British Menopause Society & Women's Health Concern recommendations on hormone replacement therapy, Menopause International: The Integrated Journal of Postreproductive Health, published online May 23, 2013, Sage Publications. http://min.sagepub.com/content/early/2013/05/23/1754045313489645. 1.
Panchangnula et al., Development and evaluation of an intracutaneous depot formulation of corticosteroids using Transcutol . . . , J Pharm Pharmacol. Sep. 1991;43(9):609-614 (abstract only).
Parasuraman et al., Blood sample collection in small laboratory animals, Journal of Pharmacology & Pharmacotherapeutics | Jul.-Dec. 2010 | vol. 1 | Issue 2, pp. 87-93.
Park, Jeong-Sook, Solvent effects on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Patel et al., Transdermal Drug Delivery System: A Review, www.thepharmajournal.com, vol. 1, No. 4, 2012, pp. 78-87.
Payne, R.S., et al., Examples of successful crystal structure prediction: polymorphs of primidone and progesterone, Intl. Jour. of Pharma., vol. 177 pp. 231-245, 1999, Elsevier.
PCCA, Apothogram, PCCA, May 2014, Houston, TX.
Persson, Linda C, et al., Physicochemical Properties of Progesterone Selecte, SciFinder, pp. 1-5, Feb. 24, 2014, American Chem. Society & US Natl. Lib. of Med.
Pfaus et al., Selective facilitation of sexual solicitation in the female rat by a melanocortin receptor agonist, PNAS, Jul. 6, 2004, vol. 101, No. 27, pp. 10201-10204.
Pheasant, Richard, Polymorphism of 17-Ethinylestradiol, Schering Corporation, Bloomfield, NJ, May 1950.
Pickles, VR, Cutaneous reactions to injection of progesterone solutions into the skin, Br Med Journal, Aug. 16, 1952, pp. 373-374.
Pinkerton et al., What are the concerns about custom-compounded "bioidentical" hormone therapy? Menopause: The Journal of the North American Menopause Society, vol. 21, No. 12, 2014,pp. 1-3.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Portman, David et al., One-year treatment persistence with local estrogen therapy in postmenopausal women diagnosed as having vaginal atrophy, Menopause, vol. 22, No. 11, 2015, pp. 000/000 (8 pages).
Position Statement, Management of symptomatic vulvovaginal atrophy: 2013 position statement of the North American Menopause Society (NAMS), Menopause, vol. 20, No. 9, pp. 888-902.
Potluri, Praveen and Guru V. Betageri, "Mixed-micellar proliposomal systems for enhanced oral delivery of progesterone," Drug Delivery, 2006, vol. 13, No. 3, pp. 227-232.
Practice Bulletin No. 141, Management of Menopausal Symptoms, Obstetrics & Gynecology, ACOG, vol. 123, No. 1, Jan. 2014, pp. 202-216.
Prajapati Hetal N. et al., "A Comparative Evaluation of Mono-, Di- and Triglyceride of Medium Chain Fatty Acids by Lipid/Surfactant/ Water Phase Diagram, Solubility Determination and Dispersion Testing for Application in Pharmaceutical Dosage Form Development," Pharm Res. Jan. 2012; 29(1): 285-305. Published online Aug. 23, 2011. doi: 10.1007/s11095-011-0541-3.
Prajapati Hetal N. et al., "Effect of Difference in Fatty Acid Chain Lengths of Medium-Chain Lipids on Lipid/Surfactant/Water Phase Diagrams and Drug Solubility," J. Excipients and Food Chem. 2 (3) 2011:73-88.
Prajapati, Hetal N, et al., A comparative Evaluation of Mono-, Di- and Triglyceride of Medium Chain Fatty Acids by Lipid/Surfactant/ Water, Springerlink.com, pp. 1-21, Apr. 2011.
Prausnitz et al., Transdermal drug delivery, Nat Biotechnol. Nov. 2008 ; 26(11): 1261-1268.
Price, Sarah L, The computational prediction of pharmaceutical crystal structures and polymorphism, Adv. Drug Delivery Reviews, vol. 56 pp. 301-319, 2004, Elsevier.
Product Information Sheet, Body B1lance Cream, Tahitian Noni International, 2013, 1 page.
Product Safety Assessment: Diethylene Glycol Monoethyl Ether, Created: Sep. 24, 2007 The Dow Chemical Company Page, 5 pages.
Progesterone, The Merck Index Online, Royal Society of Chemistry, 2013, search Feb. 17, 2014 https://www.rsc.org/Merck-Index/ monograph/print/mono1500007889/progesterone?q=authorize.
Progynova TS 100, available online at file:///C:/Users/Call%20Family/ Desktop/Progynova%20TS%20100%2012%20Patches_Pack%20% 28Estradiol%20Hemihydrate%29.html, 2010.
Provider Data Sheet, About Dried Blood Spot Testing, ZRT Laboratory, 2014, 3 pages.
Rahn et al., Vaginal Estrogen for Genitourinary Syndrome of Menopause a Systematic Review, Obstet Gynecol 2014;124(6):1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.
Rao, R. et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability, 7(2):095-107, 2015.
Reisman et al., Topical Application of the Synthetic Triterpenoid RTA 408 Protects Mice from Radiation-Induced Dermatitis, Radiation Research 181, 512-520 (2014).
Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.
Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Sallee, Verney L. et al., "Determinants of intestinal mucosal uptake of short- and medium-chain fatty acids and alcohols," Journal of Lipid Research, 1973, vol. 14, 475-484.

(56) References Cited

OTHER PUBLICATIONS

Salole, Eugene G., Estradiol, Analytical Profiles of Drug Substances, vol. 15, pp. 283-318, 1986.
Salole, Eugene G., The physicochemical properties of oestradiol, Journal of Pharmaceutical & Biomedical Analysis, vol. 5, No. 7, pp. 635-648, 1987.
Santen, R.J., Menopausal hormone therapy and breast cancer, J. Steroid Biochem. Mol. Biol. (2013), Elsevier.
Santen, RJ, Vaginal administration of estradiol: effects of dose, preparation and timing on plasma estradiol levels, CLIMACTERIC 2014;17:1-14.
Sarkar, B1SU, et al., Chemical Stability of Progesterone in Compounded Topical Preparations using PLO Transdermal Cream™ and HRT Cream™ B1se . . . , J Steroids Horm Sci, 4:2, 2013.
Sarpal, K. et al., "Self emulsifying drug delivery systems: a strategy to improve oral bioavailability," Current Research & Information on Pharmaceuticals Sciences (CRIPS), 2010, vol. 11, No. 3, pp. 42-49.
Sarrel, et al., The Mortality Toll of Estrogen Avoidance: An Analysis of Excess Deaths Among Hysterectomized Women Aged 50 to 59 Years, American Journal of Public Health, Research and Practice, e1-e6. Published online ahead of print Jul. 18, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague-Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Search Report, Extended European Search Report for EP13741053.6, dated Jul. 1, 2015.
Search Report, Extended European Search Report for EP13807188.1, dated Nov. 23, 2015.
Search Report, International Search Report and Written Opinion for PCT/US12/66406, dated Jan. 24, 2013.
Search Report, International Search Report and Written Opinion for PCT/US13/23309, dated Apr. 9, 2013.
Search Report, International Search Report and Written Opinion for PCT/US13/46442, dated Nov. 1, 2013.
Search Report, International Search Report and Written Opinion for PCT/US13/46443, dated Oct. 31, 2013.
Search Report, International Search Report and Written Opinion for PCT/US13/46444, dated Oct. 31, 2013.
Search Report, International Search Report and Written Opinion for PCT/US13/46445, dated Nov. 1, 2013.
Search Report, International Search Report and Written Opinion for PCT/US14/61811, dated Jan. 21, 2015.
Search Report, International Search Report and Written Opinion for PCT/US15/23041, dated Jun. 30, 2015.
Search Report, International Search Report and Written Opinion for PCT/US15/42621, dated Oct. 29, 2015.
Serantoni, Foresti, et al., 4-Pregnen-3,20-dione (progesterone, form II), Crystal Structure Comm., vol. 4(1) pp. 189-192, 1975, CAPLUS Database.
Shao et al., Review Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Sharma, H.C., et al., Physical Properties of Progesterone Selected Refer, SciFinder, pp. 1-5, Feb. 24, 2014, American Chem. Society & US Natl. Lib. of Med.
Shrier et al., "Mucosal Immunity of the Adolescent Female Genital Tract," Journal of Adolescent Health, 2003; 32:183-186.
Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.
Siew, Adeline, moderator, Bioavailability Enhancement with Lipid-Based Drug-Delivery Systems, Pharmaceutical Technology, Aug. 2014, pp. 28, 30-31.
Sigma-Aldrich, Progesterone-Water Soluble: powder, BioReagent, suitable for cell culture), MSDS available online: http://www.sigmaaldrich.com/catalog/product/sigma/p7556.
Simon et al., Effective Treatment of Vaginal atrophy with an Ultra-low-dose estradiol vaginal tablet, Obstetrics & Gynocology, vol. 112, No. 5, Nov. 2008, pp. 1053-1060.
Simon, James A., What if the Women's Health Initiative had used transdermal estradiol and oral progesterone instead? Menopause: The Journal of the North American Menopause Society, 2014, vol. 21, No. 7, pp. 1-15.
Sitruk-Ware et al., Progestogens in hormonal replacement therapy: new molecules, risks, and benefits, Menopause: The Journal of the North American Menopause Society. vol. 9, No. 1, pp. 6-15, 2002.
Sitruk-Ware, Regine, "Pharmacological profile of progestins," Maturitas 47 (2004) 277-283.
Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.
Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.
Smyth et al., Summary of Toxicological Data, A 2-yr Study of Diethylene Glycol Monoethyl Ether in Rats, Fd Cosmet. Toxicol. vol. 2, pp. 641-642, 1964.
Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of the North American Menopause Society, 2005, vol. 12, No. 2, pp. 232-237.
Stanczyk, F.Z. et al., Ethinyl estradiol and 17β-estradiol in combined oral contraceptives: pharmacokinetics, pharmacodynamics and risk assessment, Contraception 87 (Jun. 2013) vol. 87, No. 6, pp. 706-727.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014;17 (Suppl 2):8-11.
Stanczyk, F.Z., Bhavnani, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.
Strickley, Robert T., Solubilizing excipients in oral and injectable formulations, Pharmaceutical Research Feb. 2004, vol. 21, Issue 2, pp. 201-230 (abstract only).
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.

(56) References Cited

OTHER PUBLICATIONS

Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M. et al., The light sensitivity of corticosteroids in crystalline form, Pharmaceutica acta Helvetiae, vol. 66 (5-6) pp. 137-140, 1991, Hardin Library.
Tan, Melvin S. et al., A Sensitive Method for the Determination of Progesterone in Human Plasma by LC-MS-MS, M1025, Cedra Corporation, Austin, Texas.
Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.
Tripathi, R, et al., Study of Polymorphs of Progesterone by Novel Melt Sonocrystallization Technique: A Technical Note, AAPS PhamSciTech, vol. 11, No. 3, Sep. 2010.
Trommer et al., Overcoming the stratum Corneum: The modulation of Skin Penetration, Skin Pharmacol Physiol 2006;19:106-121.
Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
USP, 401 Fats and Fixed Oils, Chemical Tests, Second Suplement to USP36-NF 31, pp. 6141-6151, 2013.
USP, Certificate-Corn Oil, Lot G0L404, Jul. 2013.
USP, Lauroyl Polyoxylglycerides, Safety Data Sheet, US, 5611 Version #02, pp. 1-9, 2013.
USP, Monographs: Progesterone, USP29, www.pharmacopeia.cn/v29240/usp29nf24s0_m69870.html, search done: Feb. 25, 2014.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
U.S. Appl. No. 13/843,428, filed Jul. 2, 2015 Non-Final Office Action.
U.S. Appl. No. 14/106,655, filed Jun. 19, 2015 Final Office Action.
U.S. Appl. No. 13/684,002, filed Mar. 20, 2013_Non-Final_Office_Action.
U.S. Appl. No. 13/684,002, filed Jul. 16, 2013_Final_Office_Action.
U.S. Appl. No. 13/684,002, filed Dec. 6, 2013_Notice_of_Allowance.
U.S. Appl. No. 13/843,362, filed Mar. 16, 2015_Restriction_Requirement.
U.S. Appl. No. 13/843,428, filed Apr. 14, 2015_Restriction_Requirement.
U.S. Appl. No. 14/099,545, filed Feb. 18, 2014_Non-Final_Office_Action.
U.S. Appl. No. 14/099,545, filed Jul. 14, 2014_Notice_of_Allowance.
U.S. Appl. No. 14/099,562, filed Feb. 20, 2014_Restriction_Requirement.
U.S. Appl. No. 14/099,562, filed Mar. 27, 2014_Non-Final_Office_Action.
U.S. Appl. No. 14/099,562, filed Jul. 2, 2014_Final_Office_Action.
U.S. Appl. No. 14/099,562, filed Dec. 10, 2014_Notice_of_Allowance.
U.S. Appl. No. 14/099,571, filed Mar. 28, 2014_Restriction_Requirement.
U.S. Appl. No. 14/099,571, filed Jul. 15, 2014_Notice_of_Allowance.
U.S. Appl. No. 14/099,582, filed Apr. 29, 2014_Restriction_Requirement.
U.S. Appl. No. 14/099,582, filed Jun. 17, 2014_Non-Final_Office_Action.
U.S. Appl. No. 14/099,582, filed Nov. 7, 2014_Notice_of_Allowance.
U.S. Appl. No. 14/099,582, filed Jan. 22, 2015_Notice_of_Allowance.
U.S. Appl. No. 14/099,598, filed May 13, 2014_Restriction_Requirement.
U.S. Appl. No. 14/099,598, filed Jul. 3, 2014_Non-Final_Office_Action.
U.S. Appl. No. 14/099,598, filed Dec. 10, 2014_Notice_of_Allowance.
U.S. Appl. No. 14/099,612, filed Mar. 20, 2014_Restriction_Requirement.
U.S. Appl. No. 14/099,612, filed Oct. 30, 2014_Non-Final_Office_Action.
U.S. Appl. No. 14/099,612, filed Nov. 26, 2014_Notice_of_Allowance.
U.S. Appl. No. 14/099,623, filed Mar. 5, 2014_Restriction_Requirement.
U.S. Appl. No. 14/099,623, filed Jul. 18, 2014_Non-Final_Office_Action.
U.S. Appl. No. 14/099,623, filed Dec. 15, 2014_Notice_of_Allowance.
U.S. Appl. No. 14/106,655, filed Jul. 3, 2014_Restriction_Requirement.
U.S. Appl. No. 14/106,655, filed Dec. 8, 2014_Non-Final_Office_Action.
U.S. Appl. No. 14/125,554, filed Dec. 5, 2014_Restriction_Requirement.
U.S. Appl. No. 14/125,554, filed Apr. 14, 2015_Non-Final_Office_Action.
U.S. Appl. No. 14/136,048, filed Nov. 4, 2014_Restriction_Requirement.
U.S. Appl. No. 14/136,048, filed Mar. 12, 2015_Non-Final_Office_Action.
U.S. Appl. No. 14/475,814, filed Oct. 1, 2014_Non-Final_Office_Action.
U.S. Appl. No. 14/475,814, filed Feb. 13, 2015_Notice_of_Allowance.
U.S. Appl. No. 14/475,864, filed Oct. 2, 2014_Non-Final_Office_Action.
U.S. Appl. No. 14/475,864, filed Feb. 11, 2015_Notice_of_Allowance.
U.S. Appl. No. 14/476,040, filed Mar. 26, 2015_Restriction_Requirement.
U.S. Appl. No. 14/521,230, filed Dec. 5, 2014_Restriction_Requirement.
U.S. Appl. No. 14/521,230, filed Feb. 18, 2015_Non-Final_Office_Action.
U.S. Appl. No. 14/624,051, filed Apr. 7, 2015_Non-Final_Office_Action.

(56) References Cited

OTHER PUBLICATIONS

Utian, Wulf H, et al., Relief of vasomotor symptoms and vaginal atrophy with lower doses of conjugated equine estrogens, Fertility and Sterility, vol. 75(6) pp. 1065, Jun. 2001.

Voegtline et al., Dispatches from the interface of salivary bioscience and neonatal research, Frontiers in Endocrinology, Mar. 2014, vol. 5, article 25, 8 pages.

Waddell et al., Distribution and metabolism of topically applied progesterone in a rat model, Journal of Steroid Biochemistry & Molecular Biology 80 (2002) 449-455.

Waddell et al., The Metabolic Clearance of Progesterone in the Pregnant Rat: Absence of a Physiological Role For the Lung, Biology of Reproduction 40, 1188-1193 (1989).

Walter et al., The role of progesterone in endometrial angiogenesis in pregnant and ovariectomised mice, Reproduction (2005) 129 765-777.

Weber, E.J., Corn Lipids, Cereal Chem., vol. 55(5), pp. 572-584, The American Assoc of Cereal Chem, Sep.-Oct. 1978.

Weber, M.T., et al., Cognition and mood in perimenopause: A systematic review and meta-analysis, J. Steroid Biochem. Mol. Biol. (2013), Elsevier.

Weintraub, Arlene, "Women fooled by untested hormones from compounding pharmacies," Forbes, Feb. 20, 2015; retrieved online at http://onforb.es/1LIUm1V, on Feb. 23, 2015, 3 pages.

Whitehead et al., Absorption and metabolism of oral progesterone, The British Medical Journal, vol. 280, No. 6217 (Mar. 22, 1980), pp. 825-827, BMJ Publishing Group.

Wiranidchapong, Chutima, Method of preparation does not affect the miscibility between steroid hormone and polymethacrylate, Thermochimica Acta 485, Elsevier, pp. 57, 2009.

Wood et al., Effects of estradiol with micronized progesterone or medroxyprogesterone acetate on risk markers for breast cancer in postmenopausal monkeys, Breast Cancer Res Treat (2007) 101:125-134.

Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.

Wu et al., Gene Expression Profiling of the Effects of Castration and Estrogen Treatment in the Rat Uterus, Biology of Reproduction 69, 1308-1317 (2003).

Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.

Yalkowsky, Samuel H, Handbook of Acqueous Solubility Data, Solutions, 2003, pp. 1110-1111, CRC Press, Boca Raton, London, New York, Wash. D.C.

Yue, W., Genotoxic metabolites of estradiol in breast: potential mechanism of estradiol induced carcinogenesis, Journal of Steroid Biochem & Mol Biology, vol. 86 pp. 477-486, 2003.

Zava, David T. et al., Percutaneous absorption of progesterone, Maturitas 77 (2014) 91-92, Elsevier.

Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.

* cited by examiner

NATURAL COMBINATION HORMONE REPLACEMENT FORMULATIONS AND THERAPIES

CROSS-REFERENCE TO RELATED APPLICATIONS

This application claims priority to U.S. Provisional Application Ser. No. 62/002,090, filed May 22, 2014, the content of which is incorporated by reference herein in its entirety.

FIELD OF THE INVENTION

This application relates to pharmaceutical compositions and methods for hormone replacement therapy.

BACKGROUND OF THE INVENTION

Hormone Replacement Therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones in a pre-menopausal, peri-menopausal, menopausal or post-menopausal subject.

BRIEF SUMMARY OF THE INVENTION

In one aspect, pharmaceutical compositions for co-administering estradiol and progesterone to a subject in need of natural hormone replacement therapies are provided. In some embodiments, the pharmaceutical composition comprises: solubilized estradiol, suspended progesterone, and a solubilizing agent, wherein the solubilizing agent is a medium chain (C6-C12) oil and wherein the pharmaceutical composition, when administered to a subject, produces in a plasma sample from the subject one or more pharmacokinetic parameters as described herein (e.g., an area under the curve $AUC_{(0-t)}$ or a $C_{max}$ for estradiol, progesterone, estrone, or total estrone as described herein, e.g., in Tables 18-21).

In some embodiments, the pharmaceutical composition comprises a solubilizing agent that comprises a glyceride of at least one C6-C12 fatty acid. In some embodiments, the glyceride ester is a mixture of mono- and diglycerides (e.g., glyceryl caprylate/caprate). In some embodiments, the fatty acid is predominantly a C8 to C10 fatty acid. In some embodiments, the pharmaceutical composition further comprises a surfactant (e.g., lauroyl polyoxyglyceride). In some embodiments, the pharmaceutical composition comprises estradiol at a dosage of about 0.05, 0.1, 0.125, 0.15, 0.20, 0.25, 0.30, 0.35, 0.375, 0.40, 0.45, 0.50, 0.55, 0.60, 0.625, 0.65, 0.70, 0.75, 0.80, 0.85, 0.90, 0.95, 1.00, 1.125, 1.25, 1.375, 1.50, 1.625, 1.75, or 2.00 mg, and comprises progesterone at a dosage of about 25, 50, 75, 100, 125, 150, 175, 200, 250, 300, 350, or 400 mg. In some embodiments, the pharmaceutical composition comprises estradiol at a dosage of about 0.25 mg and comprises progesterone at a dosage of about 50 mg. In some embodiments, the pharmaceutical composition comprises estradiol at a dosage of about 0.50 mg and comprises progesterone at a dosage of about 50 mg. In some embodiments, the pharmaceutical composition comprises estradiol at a dosage of about 0.50 mg and comprises progesterone at a dosage of about 100 mg. In some embodiments, the pharmaceutical composition comprises estradiol at a dosage of about 1 mg and comprises progesterone at a dosage of about 100 mg. In some embodiments, the pharmaceutical composition comprises estradiol at a dosage of about 2 mg and comprises progesterone at a dosage of about 200 mg.

In some embodiments, the pharmaceutical composition comprises about 0.25 mg estradiol and about 50 mg progesterone, and administration of the composition to the subject produces, in a plasma sample from the subject, one or more parameters selected from:
  (i) an area under the curve $(AUC)_{(0-t)}$ for estradiol that is from 140.3733 pg·hr/ml to 219.3333 pg·hr/ml;
  (ii) a $C_{max}$ for estradiol that is from 6.4790 pg/ml to 10.1235 pg/ml;
  (iii) an $AUC_{(0-t)}$ for progesterone that is from 24.0174 ng·hr/ml to 37.5272 ng·hr/ml; and
  (iv) a $C_{max}$ for progesterone that is from 17.8444 ng/ml to 27.8819 ng/ml.

In some embodiments, administration of the composition to the subject further produces, in a plasma sample from the subject, one or both parameters selected from: an $AUC_{(0-t)}$ for estrone that is from 909.6091 pg·hr/ml to 1421.2642 pg·hr/ml; and a $C_{max}$ for estrone that is from 42.6549 pg/ml to 66.6483 pg/ml.

In some embodiments, administration of the composition to subject further produces, in a plasma sample from the subject, one or both parameters selected from: an $AUC_{(0-t)}$ for total estrone that is from 20.1752 ng·hr/ml to 31.5238 ng·hr/ml; and a $C_{max}$ for total estrone that is from 3.5429 ng/ml to 5.5358 ng/ml.

In some embodiments, the pharmaceutical composition comprises about 0.25 mg estradiol and about 50 mg progesterone, and administration of the composition to a subject produces, in a plasma sample from the subject, the following parameters:
  (i) one or both of (a) an $AUC_{(0-t)}$ for estradiol that is from 140.3733 pg·hr/ml to 219.3333 pg·hr/ml and (b) a $C_{max}$ for estradiol that is from 6.4790 pg/ml to 10.1235 pg/ml; and
  (ii) one or both of (a) an $AUC_{(0-t)}$ for progesterone that is from 24.0174 ng·hr/ml to 37.5272 ng·hr/ml and (b) a $C_{max}$ for progesterone that is from 17.8444 ng/ml to 27.8819 ng/ml; and optionally
  (iii) one or both of (a) an $AUC_{(0-t)}$ for estrone that is from 909.6091 pg·hr/ml to 1421.2642 pg·hr/ml and (b) a $C_{max}$ for estrone that is from 42.6549 pg/ml to 66.6483 pg/ml; and optionally
  (iv) one or both of (a) an $AUC_{(0-t)}$ for total estrone that is from 20.1752 ng·hr/ml to 31.5238 ng·hr/ml and (b) a $C_{max}$ for total estrone that is from 3.5429 ng/ml to 5.5358 ng/ml.

In some embodiments, a pharmaceutical composition for co-administering estradiol and progesterone to a human subject in need thereof comprises about 0.50 mg estradiol and about 50 mg progesterone, and administration of the composition to the subject produces, in a plasma sample from the subject, one or more parameters selected from:
  (i) an $AUC_{(0-t)}$ for estradiol that is from 280.7467 pg·hr/ml to 438.6667 pg·hr/ml;
  (ii) a $C_{max}$ for estradiol that is from 12.9580 pg/ml to 20.2469 pg/ml;
  (iii) an $AUC_{(0-t)}$ for progesterone that is from 24.0174 ng·hr/ml to 37.5272 ng·hr/ml; and
  (iv) a $C_{max}$ for progesterone that is from 17.8444 ng/ml to 27.8819 ng/ml.

In some embodiments, administration of the composition to the subject further produces, in a plasma sample from the subject, one or both parameters selected from: an $AUC_{(0-t)}$ for estrone that is from 1819.2181 pg·hr/ml to 2842.5283 pg·hr/ml, and a $C_{max}$ for estrone that is from 85.3098 pg/ml to 133.2966 pg/ml.

In some embodiments, administration of the composition to the subject further produces, in a plasma sample from the subject, one or both parameters selected from: an $AUC_{(0-t)}$ for total estrone that is from 40.3505 ng·hr/ml to 63.0476 ng·hr/ml, and a $C_{max}$ for total estrone that is from 7.0858 ng/ml to 11.0715 ng/ml.

In some embodiments, the pharmaceutical composition comprises about 0.50 mg estradiol and about 50 mg progesterone, and administration of the composition to a subject produces, in a plasma sample from the subject, the following parameters:
  (i) one or both of (a) an $UC_{(0-t)}$ for estradiol that is from 280.7467 pg·hr/ml to 438.6667 pg·hr/ml and (b) a $C_{max}$ for estradiol that is from 12.9580 pg/ml to 20.2469 pg/ml; and
  (ii) one or both of (a) an $AUC_{(0-t)}$ for progesterone that is from 24.0174 ng·hr/ml to 37.5272 ng·hr/ml and (b) a $C_{max}$ for progesterone that is from 17.8444 ng/ml to 27.8819 ng/ml; and optionally
  (iii) one or both of (a) an $AUC_{(0-t)}$ for estrone that is from 1819.2181 pg·hr/ml to 2842.5283 pg·hr/ml and (b) a $C_{max}$ for estrone that is from 85.3098 pg/ml to 133.2966 pg/ml; and optionally
  (iv) one or both of (a) an $AUC_{(0-t)}$ for total estrone that is from 40.3505 ng·hr/ml to 63.0476 ng·hr/ml and (b) a $C_{max}$ for total estrone that is from 7.0858 ng/ml to 11.0715 ng/ml.

In some embodiments, a pharmaceutical composition for co-administering estradiol and progesterone to a human subject in need thereof comprises about 0.50 mg estradiol and about 100 mg progesterone, and administration of the composition to the subject produces, in a plasma sample from the subject, one or more parameters selected from:
  (i) an area under the curve $(AUC)_{(0-t)}$ for estradiol that is from 280.7467 pg·hr/ml to 438.6667 pg·hr/ml;
  (ii) a $C_{max}$ for estradiol that is from 12.9580 pg/ml to 20.2469 pg/ml;
  (iii) an $AUC_{(0-t)}$ for progesterone that is from 48.0348 ng·hr/ml to 75.0543 ng·hr/ml; and
  (iv) a $C_{max}$ for progesterone that is from 35.6889 ng/ml to 55.7639 ng/ml.

In some embodiments, administration of the composition to the subject further produces, in a plasma sample from the subject, one or both parameters selected from: an $AUC_{(0-t)}$ for estrone that is from 1819.2181 pg·hr/ml to 2842.5283 pg·hr/ml, and a $C_{max}$ for estrone that is from 85.3098 pg/ml to 133.2966 pg/ml.

In some embodiments, administration of the composition to the subject further produces, in a plasma sample from the subject, one or both parameters selected from: an $AUC_{(0-t)}$ for total estrone that is from 40.3505 ng·hr/ml to 63.0476 ng·hr/ml, and a $C_{max}$ for total estrone that is from 7.0858 ng/ml to 11.0715 ng/ml.

In some embodiments, the pharmaceutical composition comprises about 0.50 mg estradiol and about 100 mg progesterone, and administration of the composition to a subject produces, in a plasma sample from the subject, the following parameters:
  (i) one or both of (a) an $AUC_{(0-t)}$ for estradiol that is from 280.7467 pg·hr/ml to 438.6667 pg·hr/ml and (b) a $C_{max}$ for estradiol that is from 12.9580 pg/ml to 20.2469 pg/ml; and
  (ii) one or both of (a) an $AUC_{(0-t)}$ for progesterone that is from 48.0348 ng·hr/ml to 75.0543 ng·hr/ml and (b) a $C_{max}$ for progesterone that is from 35.6889 ng/ml to 55.7639 ng/ml; and optionally
  (iii) one or both of (a) an $AUC_{(0-t)}$ for estrone that is from 1819.2181 pg·hr/ml to 2842.5283 pg·hr/ml and (b) a $C_{max}$ for estrone that is from 85.3098 pg/ml to 133.2966 pg/ml; and optionally
  (iv) one or both of (a) an $AUC_{(0-t)}$ for total estrone that is from 40.3505 ng·hr/ml to 63.0476 ng·hr/ml and (b) a $C_{max}$ for total estrone that is from 7.0858 ng/ml to 11.0715 ng/ml.

In some embodiments, a pharmaceutical composition for co-administering estradiol and progesterone to a human subject in need thereof comprises about 1 mg estradiol and about 100 mg progesterone, and administration of the composition to the subject produces, in a plasma sample from the subject, one or more parameters selected from:
  (i) an area under the curve $(AUC)_{(0-t)}$ for estradiol that is from 561.4933 pg·hr/ml to 877.3333 pg·hr/ml;
  (ii) a $C_{max}$ for estradiol that is from 25.9161 pg/ml to 40.4939 pg/ml;
  (iii) an $AUC_{(0-t)}$ for progesterone that is from 48.0348 ng·hr/ml to 75.0543 ng·hr/ml; and
  (iv) a $C_{max}$ for progesterone that is from 35.6889 ng/ml to 55.7639 ng/ml.

In some embodiments, administration of the composition to the subject further produces, in a plasma sample from the subject, one or both parameters selected from: an $AUC_{(0-t)}$ for estrone that is from 3638.4363 pg·hr/ml to 5685.0567 pg·hr/ml, and a $C_{max}$ for estrone that is from 170.6197 pg/ml to 266.5933 pg/ml.

In some embodiments, administration of the composition to the subject further produces, in a plasma sample from the subject, one or both parameters selected from: an $AUC_{(0-t)}$ for total estrone that is from 80.7010 ng·hr/ml to 126.0953 ng·hr/ml, and a $C_{max}$ for total estrone that is from 14.1716 ng/ml to 22.1431 ng/ml.

In some embodiments, the pharmaceutical composition comprises about 0.50 mg estradiol and about 100 mg progesterone, and administration of the composition to a subject produces, in a plasma sample from the subject, the following parameters:
  (i) one or both of (a) an $AUC_{(0-t)}$ for estradiol that is from 561.4933 pg·hr/ml to 877.3333 pg·hr/ml and (b) a $C_{max}$ for estradiol that is from 25.9161 pg/ml to 40.4939 pg/ml; and
  (ii) one or both of (a) an $AUC_{(0-t)}$ for progesterone that is from 48.0348 ng·hr/ml to 75.0543 ng·hr/ml and (b) a $C_{max}$ for progesterone that is from 35.6889 ng/ml to 55.7639 ng/ml; and optionally
  (iii) one or both of (a) an $AUC_{(0-t)}$ for estrone that is from 3638.4363 pg·hr/ml to 5685.0567 pg·hr/ml and (b) a $C_{max}$ for estrone that is from 170.6197 pg/ml to 266.5933 pg/ml; and optionally
  (iv) one or both of (a) an $AUC_{(0-t)}$ for total estrone that is from 80.7010 ng·hr/ml to 126.0953 ng·hr/ml and (b) a $C_{max}$ for total estrone that is from 14.1716 ng/ml to 22.1431 ng/ml.

In some embodiments, the pharmaceutical composition has the blood plasma estradiol concentration profile of FIG. 1. In some embodiments, the pharmaceutical composition has the blood plasma progesterone concentration profile of FIG. 2. In some embodiments, the pharmaceutical composition has the blood plasma estrone concentration profile of FIG. 3. In some embodiments, the pharmaceutical composition has the blood plasma total estrone concentration profile of FIG. 4.

In some embodiments, the one or more parameters as described herein (e.g., the $AUC_{(0-t)}$ or $C_{max}$ for progesterone, estradiol, estrone, or total estrone) are measured at regular intervals (e.g., about every 30 minutes, about every 60 minutes, or about every 90 minutes) or at irregular intervals over a period of time such as 24 hours or 48 hours. In some embodiments, the one or more parameters as described herein (e.g., the $AUC_{(0-t)}$ or $C_{max}$ for progesterone, estradiol, estrone, or total estrone) are measured at about 0.25 hr, 0.5 hr, 0.67 hr, 0.83 hr, 1 hr, 1.33 hr, 1.67 hr, 2 hr, 2.5 hr, 3 hr, 4 hr, 5 hr, 6 hr, 7 hr, 8 hr, 10 hr, 12 hr, 18 hr, 24 hr, 36 hr, or 48 hr after administering the pharmaceutical composition to the subject. In some embodiments, the one or more parameters as described herein are measured at regular or irregular intervals following the administration of a single dose or of a first dose of the pharmaceutical composition to the subject.

In another aspect, methods of treating a subject are provided. In some embodiments, the subject has a condition that is caused at least in part by an estrogen deficiency (e.g., one or more symptoms of menopause, such as vasomotor symptoms). In some embodiments, the method comprises administering to the subject a pharmaceutical composition comprising solubilized estradiol, suspended progesterone, and a solubilizing agent that comprises a medium chain (C6-C12) oil as described herein, wherein administration of the pharmaceutical composition produces, in a plasma sample from the subject, one or more pharmacokinetic parameters as described herein. In some embodiments, the method comprises administering a pharmaceutical composition comprising estradiol at a dosage of about 0.05, 0.1, 0.125, 0.15, 0.20, 0.25, 0.30, 0.35, 0.375, 0.40, 0.45, 0.50, 0.55, 0.60, 0.625, 0.65, 0.70, 0.75, 0.80, 0.85, 0.90, 0.95, 1.00, 1.125, 1.25, 1.375, 1.50, 1.625, 1.75, or 2.00 mg, and comprising progesterone at a dosage of about 25, 50, 75, 100, 125, 150, 175, 200, 250, 300, 350, or 400 mg. In some embodiments, the method comprises administering a pharmaceutical composition comprising: estradiol at a dosage of about 0.25 mg and progesterone at a dosage of about 50 mg; estradiol at a dosage of about 0.50 mg and progesterone at a dosage of about 50 mg; estradiol at a dosage of about 0.50 mg and progesterone at a dosage of about 100 mg; estradiol at a dosage of about 1 mg and progesterone at a dosage of about 100 mg; or estradiol at a dosage of about 2 mg and progesterone at a dosage of about 200 mg.

In some embodiments, the method comprises administering to the subject a pharmaceutical composition comprising about 0.25 mg estradiol and about 50 mg progesterone, wherein administration of the pharmaceutical composition produces, in a plasma sample from the subject, one or more parameters selected from:
  (i) an area under the curve $(AUC)_{(0-t)}$ for estradiol that is from 140.3733 pg·hr/ml to 219.3333 pg·hr/ml;
  (ii) a $C_{max}$ for estradiol that is from 6.4790 pg/ml to 10.1235 pg/ml;
  (iii) an $AUC_{(0-t)}$ for progesterone that is from 24.0174 ng·hr/ml to 37.5272 ng·hr/ml; and
  (iv) a $C_{max}$ for progesterone that is from 17.8444 ng/ml to 27.8819 ng/ml.

In some embodiments, administration of the pharmaceutical composition further produces, in a plasma sample from the subject, one or more parameters selected from: an $AUC_{(0-t)}$ for estrone that is from 909.6091 pg·hr/ml to 1421.2642 pg·hr/ml; a $C_{max}$ for estrone that is from 42.6549 pg/ml to 66.6483 pg/ml; an $AUC_{(0-t)}$ for total estrone that is from 20.1752 ng·hr/ml to 31.5238 ng·hr/ml; and a $C_{max}$ for total estrone that is from 3.5429 ng/ml to 5.5358 ng/ml.

In some embodiments, the method comprises administering to the subject a pharmaceutical composition comprising about 0.25 mg estradiol and about 50 mg progesterone, wherein administration of the pharmaceutical composition produces, in a plasma sample from the subject, the following parameters:
  (i) one or both of (a) an $AUC_{(0-t)}$ for estradiol that is from 140.3733 pg·hr/ml to 219.3333 pg·hr/ml and (b) a $C_{max}$ for estradiol that is from 6.4790 pg/ml to 10.1235 pg/ml; and
  (ii) one or both of (a) an $AUC_{(0-t)}$ for progesterone that is from 24.0174 ng·hr/ml to 37.5272 ng·hr/ml and (b) a $C_{max}$ for progesterone that is from 17.8444 ng/ml to 27.8819 ng/ml; and optionally
  (iii) one or both of (a) an $AUC_{(0-t)}$ for estrone that is from 909.6091 pg·hr/ml to 1421.2642 pg·hr/ml and (b) a $C_{max}$ for estrone that is from 42.6549 pg/ml to 66.6483 pg/ml; and optionally
  (iv) one or both of (a) an $AUC_{(0-t)}$ for total estrone that is from 20.1752 ng·hr/ml to 31.5238 ng·hr/ml and (b) a $C_{max}$ for total estrone that is from 3.5429 ng/ml to 5.5358 ng/ml.

In some embodiments, the method comprises administering to the subject a pharmaceutical composition comprising about 0.50 mg estradiol and about 50 mg progesterone, wherein administration of the pharmaceutical composition produces, in a plasma sample from the subject, one or more parameters selected from:
  (i) an $AUC_{(0-t)}$ for estradiol that is from 280.7467 pg·hr/ml to 438.6667 pg·hr/ml;
  (ii) a $C_{max}$ for estradiol that is from 12.9580 pg/ml to 20.2469 pg/ml;
  (iii) an $AUC_{(0-t)}$ for progesterone that is from 24.0174 ng·hr/ml to 37.5272 ng·hr/ml; and
  (iv) a $C_{max}$ for progesterone that is from 17.8444 ng/ml to 27.8819 ng/ml.

In some embodiments, administration of the composition to the subject further produces, in a plasma sample from the subject, one or more parameters selected from: an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; an $AUC_{(0-t)}$ for total estrone that is from 40.3505 ng·hr/ml to 63.0476 ng·hr/ml; and a $C_{max}$ for total estrone that is from 7.0858 ng/ml to 11.0715 ng/ml.

In some embodiments, the method comprises administering to the subject a pharmaceutical composition comprising about 0.50 mg estradiol and about 50 mg progesterone, wherein administration of the pharmaceutical composition produces, in a plasma sample from the subject, the following parameters:
  (i) one or both of (a) an $AUC_{(0-t)}$ for estradiol that is from 280.7467 pg·hr/ml to 438.6667 pg·hr/ml and (b) a $C_{max}$ for estradiol that is from 12.9580 pg/ml to 20.2469 pg/ml; and
  (ii) one or both of (a) an $AUC_{(0-t)}$ for progesterone that is from 24.0174 ng·hr/ml to 37.5272 ng·hr/ml and (b) a $C_{max}$ for progesterone that is from 17.8444 ng/ml to 27.8819 ng/ml; and optionally
  (iii) one or both of (a) an $AUC_{(0-t)}$ for estrone that is from 1819.2181 pg·hr/ml to 2842.5283 pg·hr/ml and (b) a $C_{max}$ for estrone that is from 85.3098 pg/ml to 133.2966 pg/ml; and optionally
  (iv) one or both of (a) an an $AUC_{(0-t)}$ for total estrone that is from 40.3505 ng·hr/ml to 63.0476 ng·hr/ml and (b) a $C_{max}$ for total estrone that is from 7.0858 ng/ml to 11.0715 ng/ml.

In some embodiments, the method comprises administering to the subject a pharmaceutical composition comprising about 0.50 mg estradiol and about 100 mg progesterone, wherein administration of the pharmaceutical composition produces, in a plasma sample from the subject, one or more parameters selected from:
 (i) an area under the curve $(AUC)_{(0-t)}$ for estradiol that is from 280.7467 pg·hr/ml to 438.6667 pg·hr/ml;
 (ii) a $C_{max}$ for estradiol that is from 12.9580 pg/ml to 20.2469 pg/ml;
 (iii) an $AUC_{(0-t)}$ for progesterone that is from 48.0348 ng·hr/ml to 75.0543 ng·hr/ml; and
 (iv) a $C_{max}$ for progesterone that is from 35.6889 ng/ml to 55.7639 ng/ml.

In some embodiments, administration of the composition to the subject further produces, in a plasma sample from the subject, one or more parameters selected from: an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; an $AUC_{(0-t)}$ for total estrone that is from 40.3505 ng·hr/ml to 63.0476 ng·hr/ml, and a $C_{max}$ for total estrone that is from 7.0858 ng/ml to 11.0715 ng/ml.

In some embodiments, the method comprises administering to the subject a pharmaceutical composition comprising about 0.50 mg estradiol and about 100 mg progesterone, wherein administration of the pharmaceutical composition produces, in a plasma sample from the subject, the following parameters:
 (i) one or both of (a) an $AUC_{(0-t)}$ for estradiol that is from 280.7467 pg·hr/ml to 438.6667 pg·hr/ml and (b) a $C_{max}$ for estradiol that is from 12.9580 pg/ml to 20.2469 pg/ml; and
 (ii) one or both of (a) an $AUC_{(0-t)}$ for progesterone that is from 48.0348 ng·hr/ml to 75.0543 ng·hr/ml and (b) a $C_{max}$ for progesterone that is from 35.6889 ng/ml to 55.7639 ng/ml; and optionally
 (iii) one or both of (a) an $AUC_{(0-t)}$ for estrone that is from 1819.2181 pg·hr/ml to 2842.5283 pg·hr/ml and (b) a $C_{max}$ for estrone that is from 85.3098 pg/ml to 133.2966 pg/ml; and optionally
 (iv) one or both of (a) $AUC_{(0-t)}$ for total estrone that is from 40.3505 ng·hr/ml to 63.0476 ng·hr/ml and (b) a $C_{max}$ for total estrone that is from 7.0858 ng/ml to 11.0715 ng/ml.

In some embodiments, the method comprises administering to the subject a pharmaceutical composition comprising about 1 mg estradiol and about 100 mg progesterone, wherein administration of the pharmaceutical composition produces, in a plasma sample from the subject, one or more parameters selected from:
 (i) an area under the curve $(AUC)_{(0-t)}$ for estradiol that is from 561.4933 pg·hr/ml to 877.3333 pg·hr/ml;
 (ii) a $C_{max}$ for estradiol that is from 25.9161 pg/ml to 40.4939 pg/ml;
 (iii) an $AUC_{(0-t)}$ for progesterone that is from 48.0348 ng·hr/ml to 75.0543 ng·hr/ml; and
 (iv) a $C_{max}$ for progesterone that is from 35.6889 ng/ml to 55.7639 ng/ml.

In some embodiments, administration of the composition to the subject further produces, in a plasma sample from the subject, one or more parameters selected from: an $AUC_{(0-t)}$ for estrone that is from 3638.4363 pg·hr/ml to 5685.0567 pg·hr/ml; a $C_{max}$ for estrone that is from 170.6197 pg/ml to 266.5933 pg/ml; an $AUC_{(0-t)}$ for total estrone that is from 80.7010 ng·hr/ml to 126.0953 ng·hr/ml, and a $C_{max}$ for total estrone that is from 14.1716 ng/ml to 22.1431 ng/ml.

In some embodiments, the method comprises administering to the subject a pharmaceutical composition comprising about 1 mg estradiol and about 100 mg progesterone, wherein administration of the pharmaceutical composition produces, in a plasma sample from the subject, the following parameters:
 (i) one or both of (a) an $AUC_{(0-t)}$ for estradiol that is from 561.4933 pg·hr/ml to 877.3333 pg·hr/ml and (b) a $C_{max}$ for estradiol that is from 25.9161 pg/ml to 40.4939 pg/ml; and
 (ii) one or both of (a) an $AUC_{(0-t)}$ for progesterone that is from 48.0348 ng·hr/ml to 75.0543 ng·hr/ml and (b) a $C_{max}$ for progesterone that is from 35.6889 ng/ml to 55.7639 ng/ml; and optionally
 (iii) one or both of (a) an $AUC_{(0-t)}$ for estrone that is from 3638.4363 pg·hr/ml to 5685.0567 pg·hr/ml and (b) a $C_{max}$ for estrone that is from 170.6197 pg/ml to 266.5933 pg/ml; and optionally
 (iv) one or both of (a) an $AUC_{(0-t)}$ for total estrone that is from 80.7010 ng·hr/ml to 126.0953 ng·hr/ml and (b) a $C_{max}$ for total estrone that is from 14.1716 ng/ml to 22.1431 ng/ml.

In still another aspect, pharmaceutical compositions for use in a method of treating a disease or condition that is caused at least in part by an estrogen deficiency are provided. In some embodiments, the pharmaceutical composition comprises solubilized estradiol, suspended progesterone, and a solubilizing agent that comprises a medium chain (C6-C12) oil, wherein the treatment produces, in a plasma sample from the subject, one or more pharmacokinetic parameters as described herein (e.g., an $AUC_{(0-t)}$ or $C_{max}$ for estradiol, progesterone, estrone, or total estrone as described herein, e.g., as described in any of Tables 18-21). In some embodiments, the pharmaceutical compositions for use in a method of treating a disease or condition that is caused at least in part by an estrogen deficiency comprise estradiol at a dosage of about 0.05, 0.1, 0.125, 0.15, 0.20, 0.25, 0.30, 0.35, 0.375, 0.40, 0.45, 0.50, 0.55, 0.60, 0.625, 0.65, 0.70, 0.75, 0.80, 0.85, 0.90, 0.95, 1.00, 1.125, 1.25, 1.375, 1.50, 1.625, 1.75, or 2.00 mg, and comprise progesterone at a dosage of about 25, 50, 75, 100, 125, 150, 175, 200, 250, 300, 350, or 400 mg.

In some embodiments, a pharmaceutical composition for use in a method of treating a disease or condition that is caused at least in part by an estrogen deficiency (e.g., one or more symptoms of menopause) comprises estradiol at a dosage of about 0.25 mg and progesterone at a dosage of about 50 mg, and produces one or more pharmacokinetic values disclosed in Table 18 following administration of a single dose of the pharmaceutical composition to a subject (e.g., about 24 hours or about 48 hours after administration).

In some embodiments, a pharmaceutical composition for use in a method of treating a disease or condition that is caused at least in part by an estrogen deficiency (e.g., one or more symptoms of menopause) comprises estradiol at a dosage of about 0.50 mg and progesterone at a dosage of about 50 mg, and produces one or more pharmacokinetic values disclosed in Table 19 following administration of a single dose of the pharmaceutical composition to a subject (e.g., about 24 hours or about 48 hours after administration).

In some embodiments, a pharmaceutical composition for use in a method of treating a disease or condition that is caused at least in part by an estrogen deficiency (e.g., one or more symptoms of menopause) comprises estradiol at a dosage of about 0.50 mg and progesterone at a dosage of about 100 mg, and produces one or more pharmacokinetic values disclosed in Table 20 following administration of a single dose of the pharmaceutical composition to a subject (e.g., about 24 hours or about 48 hours after administration).

In some embodiments, a pharmaceutical composition for use in a method of treating a disease or condition that is caused at least in part by an estrogen deficiency (e.g., one or more symptoms of menopause) comprises estradiol at a dosage of about 1 mg and progesterone at a dosage of about 100 mg, and produces one or more pharmacokinetic values disclosed in Table 21 following administration of a single dose of the pharmaceutical composition to a subject (e.g., about 24 hours or about 48 hours after administration).

DETAILED DESCRIPTION OF THE INVENTION

Figure 1:
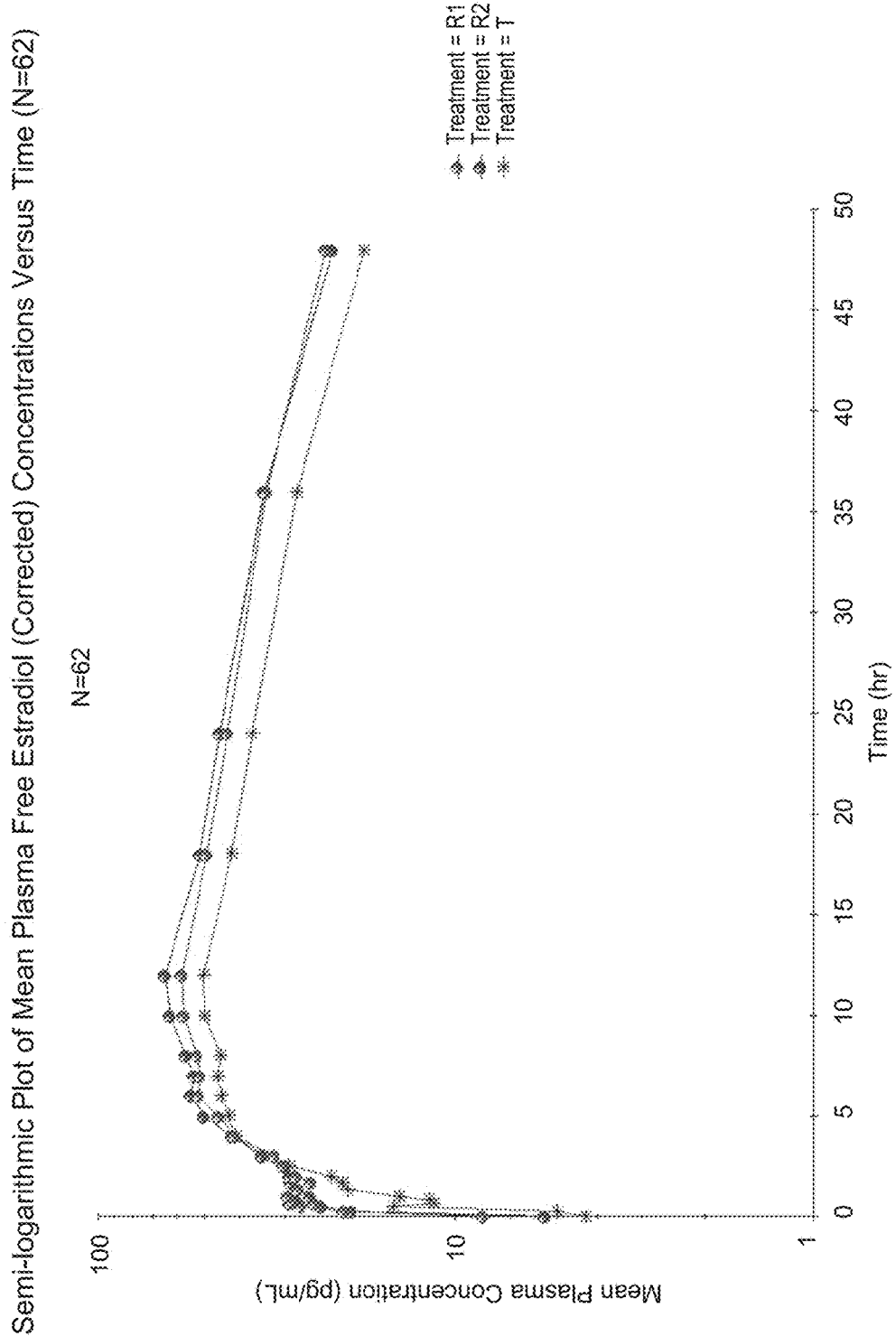
FIG. 1 illustrates a semilogarithmic plot of mean plasma concentration (pg/ml) over time (hrs) for estradiol.

In the following detailed description of embodiments of this disclosure, reference is made to the accompanying drawings in which like references indicate similar elements, and in which is shown, by way of illustration, specific embodiments in which this disclosure may be practiced. These embodiments are described in sufficient detail to enable those skilled in the art to practice this disclosure, and it is to be understood that other embodiments may be utilized and that other changes may be made without departing from the scope of this disclosure. The following detailed description is, therefore, not to be taken in a limiting sense, and the scope of this disclosure is defined only by the appended claims. As used in this disclosure, the term "or" shall be understood to be defined as a logical disjunction (i.e., and/or) and shall not indicate an exclusive disjunction unless expressly indicated as such with the term "either," "unless," "alternatively," and words of similar effect.

I. DEFINITIONS

The term "area under the curve" ("AUC") refers to the area under the curve defined by changes in the blood, plasma, or serum concentration of an active pharmaceutical ingredient (e.g., estradiol or progesterone), or one or more metabolites of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with measurable concentration.

The term "$C_{max}$" refers to the maximum value of blood, plasma, or serum concentration shown on the curve that represents changes in blood, plasma, or serum concentrations of an active pharmaceutical ingredient (e.g., progesterone or estradiol), or one or more metabolites of the active pharmaceutical ingredient, over time.

The term "$T_{max}$" refers to the time that it takes for the blood, plasma, or serum concentration of an active pharmaceutical ingredient (e.g., estradiol or progesterone), or of one or more metabolites of the active pharmaceutical ingredient, to reach the maximum value.

Collectively, AUC, $C_{max}$, and, optionally, $T_{max}$ are the principal pharmacokinetic parameters that can characterize the pharmacokinetic response of a particular drug product, such as progesterone or estradiol, in an animal, especially a mammal, including human, subject.

An "active pharmaceutical ingredient" (API), as used herein, means the active compound or compounds used in formulating a drug product. APIs are generally safe for administering to animals, especially mammals, including humans, according to established governmental standards, including those promulgated by the United States Food and Drug Administration.

The term "bioavailability" has the meaning as defined in 21 C.F.R. § 320.1(a): the rate and extent to which an API or active ingredient or active moiety is absorbed from a drug product and becomes available at the site of action. For drug products that are not intended to be absorbed into the bloodstream, bioavailability may be assessed by measurements intended to reflect the rate and extent to which the API or active ingredient or active moiety becomes available at the site of action. For example, bioavailability can be measured as the amount of API in the blood (whole blood, serum, or plasma) as a function of time. In embodiments, the amount of API is measured in blood plasma. Pharmacokinetic (PK) parameters such as AUC, $C_{max}$, or $T_{max}$ may be used to measure and assess bioavailability.

The term "bioequivalent" has the meaning as defined in 21 C.F.R. § 320.1(e): the absence of a significant difference in the rate and extent to which the API or active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms or modified release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC, $C_{max}$, or optionally $T_{max}$ is within 80.00% to 125.00%.

The term "bio-identical hormone" or "body-identical hormone" refers to an active pharmaceutical ingredient that is structurally identical to a hormone naturally or endogenously found in the human body (e.g., estradiol and progesterone).

The term "estrogen" refers to a group of several female sex hormones produced primarily by the ovaries, including estradiol, estrone, and estriol. As used herein, unless otherwise specified, estrogen refers to estradiol.

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

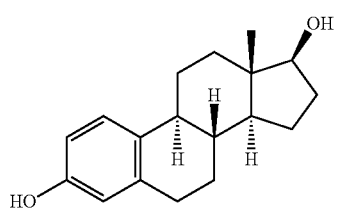

As used herein, unless specified, estradiol includes estradiol in anhydrous or hemi-hydrate forms. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agents or the formulations disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body having the structure:

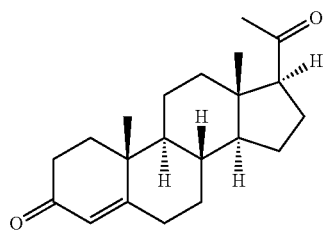

The term "solubilized progesterone" means that the progesterone or a portion thereof is solubilized or dissolved in the solubilizing agents or the formulations disclosed herein disclosed herein. In some embodiments, the progesterone is "partially solubilized" with a portion of the progesterone being solubilized or dissolved in the solubilizing agent and a portion of the progesterone being suspended in the solubilizing agent. Partially solubilized progesterone may include progesterone that is about 1% solubilized, about 5% solubilized, about 10% solubilized, about 15% solubilized, about 20% solubilized, about 30% solubilized, about 40% solubilized, about 50% solubilized, about 60% solubilized, about 70% solubilized, about 80% solubilized, about 85% solubilized, about 90% solubilized or about 95% solubilized. In other embodiments, the progesterone is "fully solubilized" with all or substantially all of the progesterone being solubilized or dissolved in the solubilizing agent. Fully solubilized progesterone may include progesterone that is about 97% solubilized, about 98% solubilized, about 99% solubilized or about 100% solubilized. Solubility can be expressed as a mass fraction (% w/w, which is also referred to as wt %).

The terms "micronized progesterone" and "micronized estradiol," as used herein, include micronized progesterone and micronized estradiol, respectively, having an X50 particle size value below about 15 microns or having an X90 particle size value below about 25 microns. The term "X50" means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "solubilizing agent" refers to an agent or combination of agents that solubilize an active pharmaceutical ingredient (e.g., estradiol or progesterone). For example and without limitation, suitable solubilizing agents include medium chain oils and other solvents and co-solvents that solubilize or dissolve an active pharmaceutical ingredient to a desirable extent. Solubilizing agents suitable for use in the formulations disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc. In some embodiments, the solubilizing agent is a medium chain oil and, in some other embodiments, the medium chain oil is combined with a co-solvent(s) or other excipient(s).

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain between 6 (C6) and 14 (C14) carbon atoms.

The terms "medium chain fatty acid" and "medium chain fatty acid derivative" are used to describe fatty acids or fatty acid derivatives with aliphatic tails (i.e., carbon chains) having 6 to 14 carbons. Fatty acids consist of an unbranched aliphatic tail attached to a carboxylic acid functional group. Fatty acid derivatives include, for example, fatty acid esters and fatty acid containing molecules, including, without limitation, mono-, di- and triglycerides that include components derived from fatty acids as well as fatty acid esters of ethylene or propylene glycol. Those of skill will appreciate that the aliphatic tails can be saturated or unsaturated (one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. In embodiments, medium chain fatty acids or medium chain fatty acid derivatives are those that are saturated. Examples include, without limitation, caproic acid, caprylic acid, capric acid, lauric acid, myristic acid, and derivatives thereof.

The term "oil," as used herein, refers to any pharmaceutically acceptable oil, and specifically excluding peanut oil, that can suspend or solubilize any suitable progesterone or estradiol, starting material, or precursor, including micronized progesterone or estradiol as described herein.

The term "medium chain oil" refers to an oil wherein the composition of the fatty acid fraction of the oil is substantially medium chain (i.e., C6 to C14) fatty acids, i.e., the composition profile of fatty acids in the oil is substantially medium chain. As used herein, "substantially" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. Those of skill in the art that will readily appreciate that the terms "alkyl content" or "alkyl distribution" of an oil can be used in place of the term "fatty acid fraction" of an oil in characterizing a given oil or solubilizing agent, and these terms are used interchangeable herein. As such, medium chain oils suitable for use in the formulations disclosed herein include medium chain oils wherein the fatty acid fraction of the oil is substantially medium chain fatty acids, or medium chain oils wherein the alkyl content or alkyl distribution of the oil is substantially medium chain alkyls (C6-C12 alkyls). It will be understood by those of skill in the art that the medium chain oils suitable for use in the formulations disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16, and 16; 10, 14, and 16; 8, 14, and 18; etc. Naturally occurring oils are frequently "mixed" with respect to specific fatty acids, but tend not to contain both long chain fatty acids and medium chain fatty acids in the same glycerol backbone. Thus, triglycerides with ECNs of 21-42 typically contain predominantly medium chain fatty acids; while triglycerides with ECNs of greater than 43 typically contain predominantly long chain fatty acids. For example, the ECN of corn oil triglyceride in the US Pharmacopeia (USP) would be in the range of 51-54. Medium chain diglycerides with ECNs of 12-28 will often contain predominantly medium chain fatty acids, while diglycerides with ECNs of 32 or greater will typically contain predominantly long chain fatty acids. Monoglycerides will have an ECN that matches the chain length of the sole fatty acid chain. Thus, monoglyceride ECNs in the range of 6-14 contain mainly medium chain fatty acids, and monoglycerides with ECNs 16 or greater will contain mainly long chain fatty acids.

The average ECN of a medium chain triglyceride oil is typically 21-42. For example, as listed in the USP, medium chain triglycerides have the following composition as the exemplary oil set forth in the table below:

| Fatty Acid Tail Length | % of Oil | Exemplary Oil |
|---|---|---|
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | and would have an average ECN of 3*[(6*0.02)+(8*0.070)+(10*0.25)+(12*0.02)+(14*0.01)]=25.8. The ECN of the exemplary medium chain triglycerides oil can also be expressed as a range (per the ranges set forth in the USP) of 24.9-27.0. For oils that have mixed mono-, di-, and triglycerides, or single and double fatty acid glycols, the ECN of the entire oil can be determined by calculating the ECN of each individual component (e.g., C8 monoglycerides, C8 diglycerides, C10 monoglycerides, and C10 diglycerides) and taking the sum of the relative percentage of the component multiplied by the ECN normalized to a monoglyceride for each component. For example, the oil having C8 and C10 mono- and diglycerides shown in the table below has an ECN of 8.3, and is thus a medium chain oil:

| Fatty Acid Chain Length | % of Oil | ECN as % of Oil [(chain length) × (% in oil)] | ECN as % of Oil Normalized to Monoglyceride |
|---|---|---|---|
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: (8*0.85)+(10*0.15)=8.3.

The term "excipients," as used herein, refers to non-active pharmaceutical ingredients such as solubilizing agents, antioxidants, oils, lubricants, and others used in formulating pharmaceutical products.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

II. PHARMACEUTICAL COMPOSITIONS

In one aspect, this disclosure relates to pharmaceutical compositions for co-administering estradiol and progesterone to a human subject in need thereof. In some embodiments, the composition comprises estradiol, progesterone, and a solubilizing agent (e.g., a medium chain oil, e.g., a C6-C12 oil). In some embodiments, a pharmaceutical composition comprising estradiol, progesterone, and a solubilizing agent as described herein, when administered to a subject or a population of subjects, produces one or more AUC, $C_{max}$, or $T_{max}$ parameters for estradiol, progesterone, estrone, or total estrone as described below.

Formulations of Estradiol and Progesterone Compositions

In some embodiments, a pharmaceutical composition for use as described herein comprises solubilized estradiol with suspended progesterone; solubilized estradiol with both partially solubilized progesterone and partially suspended progesterone; or solubilized estradiol with fully solubilized progesterone. In some embodiments, the composition comprises solubilized estradiol and suspended progesterone. The underlying formulation concepts provided herein may be used with other natural or synthetic forms of estradiol and progesterone, although the natural or bio-identical forms of estradiol and progesterone are preferred.

In some embodiments, the composition comprises estradiol at a dosage of about 0.05, 0.1, 0.125, 0.15, 0.20, 0.25, 0.30, 0.35, 0.375, 0.40, 0.45, 0.50, 0.55, 0.60, 0.625, 0.65, 0.70, 0.75, 0.80, 0.85, 0.90, 0.95, 1.00, 1.125, 1.25, 1.375, 1.50, 1.625, 1.75, or 2.00 mg. In some embodiments, the composition comprises progesterone at a dosage of about 25, 50, 75, 100, 125, 150, 175, 200, 250, 300, 350, or 400 mg.

In some embodiments, estradiol is solubilized. Solubilized estradiol may include estradiol that is approximately 80% to 100% soluble in a solubilizing agent, including specifically embodiments that are: 80%, 81%, 82%, 83%, 84%, 85%, 86%, 87%, 88%, 89%, 90%, 91%, 92%, 93%, 94%, 95%, 96%, 97%, 98%, 99%, or 100% soluble in a solubilizing agent. Solubility may be expressed as a mass fraction (% w/w, also referred to as wt %). In some embodiments, estradiol is micronized. In some embodiments, micronized estradiol has an X50 particle size value of less than about 15 microns, less than about 10 microns, less than about 5 microns or less than about 3 microns. In some embodiments, micronized estradiol has an X90 particle size value of less than about 25 microns, less than about 20 microns, or less than about 15 microns. In some embodiments, the composition comprises micronized and partially solubilized estradiol.

In some embodiments, the composition comprises micronized progesterone. The progesterone active pharmaceutical ingredient may be micronized via any one of the multiple methods typically utilized by the ordinarily skilled artisan. In various embodiments, micronized progesterone has an X50 particle size value of less than about 15 microns, less than about 10 microns, less than about 5 microns or less than about 3 microns. In various embodiments, micronized progesterone has an X90 particle size value of less than about 25 microns, less than about 20 microns, or less than about 15 microns. Particle size may be determined in any suitable manner. For example, a Beckman Coulter LS 13 320 Laser Diffraction Particle Size Analyzer (the "Beckman Device") may be used to determine particle size.

Estradiol and progesterone compositions and methods of preparing such compositions are described in U.S. Pat. No. 8,633,178; U.S. Publication No. 2013/0129818; U.S. Publication No. 2013/0338123; International Publication No. WO 2013/078422; and International Publication No. WO 2013/192251; each of which is incorporated by reference in its entirety.

Solubilizing Agents

Estradiol and progesterone compositions of the present disclosure are prepared via blending with a solubilizing agent. In some embodiments, the solubilizing agent is a pharmaceutically acceptable oil that comprises a medium chain oil. In some embodiments, the solubilizing agent is a medium chain oil comprised substantially of C6-C12 medium chains, e.g., at least 20%, at least 30%, at least 40%, at least 50%, at least 60%, at least 70%, at least 80%, or at least 90% of the chains present in the oil are C6-C12. In some embodiments, the oil comprises at least one medium chain fatty acid such as medium chain fatty acids having at least one mono-, di-, or triglyceride, or derivatives thereof, or combinations thereof. In some embodiments, the medium chain oil comprises at least one medium chain fatty acid or propylene glycol, polyethylene glycol, or glyceride having esters of medium chain fatty acids. In some embodiments, the solubilizing agent is not peanut oil.

In some embodiments, oils used to solubilize estradiol and to suspend, partially suspend and partially solubilize, or fully solubilize progesterone include medium chain fatty acid esters, (e.g., esters of glycerol, polyethylene glycol, or propylene glycol) and mixtures thereof. In some embodiments, the medium chain fatty acids are C6, C8, C10, C12, C6-C12, C8-C12, C6-C10, C8-C10, or C10-C12 fatty acids. In some embodiments, the medium chain fatty acids are saturated, or predominantly saturated, e.g., greater than about 50% saturated, greater than about 60% saturated, or greater than about 75% saturated. In some embodiments, a solubilizing agent comprises predominantly medium chain length, saturated fatty acids or derivatives thereof, specifically predominantly C8 to C12 saturated fatty acids or derivatives thereof.

In some embodiments, medium chain solubilizing agents include, for example and without limitation, saturated medium chain fatty acids or derivatives of saturated medium chain fatty acids: caproic acid (C6), enanthic acid (C7), caprylic acid (C8), pelargonic acid (C9), capric acid (C10), undecylic acid (C11), lauric acid (C12), tridecylic acid (C13), or myristic acid (C14). In some embodiments, the solubilizing agent comprises oils made of these free medium chain fatty acids, oils of medium chain fatty acid esters of glycerin, propylene glycol, or ethylene glycol, or combinations thereof. These examples comprise predominantly saturated medium chain fatty acids (i.e., greater than 50% of the fatty acids are medium chain saturated fatty acids). In some embodiments, the solubilizing agent comprises predominantly C6 to C12 saturated fatty acids or derivatives of fatty acids.

In some embodiments, the solubilizing agent comprises one or more mono-, di-, or triglycerides or combinations thereof. Exemplary glycerin based solubilizing agents include MIGLYOLs®, which are caprylic/capric triglycerides (SASOL Germany GMBH, Hamburg). MIGLYOLs® includes MIGLYOL® 810 (caprylic/capric triglyceride), MIGLYOL® 812 (caprylic/capric triglyceride), MIGLYOL® 816 (caprylic/capric triglyceride), and MIGLYOL® 829 (caprylic/capric/succinic triglyceride). Other caprylic/capric triglyceride solubilizing agents are likewise contemplated, including, for example: caproic/caprylic/capric/lauric triglycerides; caprylic/capric/linoleic triglycerides; or caprylic/capric/succinic triglycerides. Other exemplary caprylic/capric mono-, di-, or triglyceride solubilizing agents include CAPMULs® (ABITEC, Columbus, Ohio), including, but are not limited to, CAPMUL® MCM, CAPMUL® MCM C10, CAPMUL® MCM C8, CAPMUL® MCM C8 EP, and CAPMUL® 708 G. Other mono-, di-, and triglycerides of fractionated vegetable fatty acids, and combinations or derivatives thereof can be the solubilizing agent, according to embodiments. For example, the solubilizing agent can be 1,2,3-propanetriol (glycerol, glycerin, glycerine) esters of saturated coconut and palm kernel oil and derivatives thereof.

In some embodiments, the solubilizing agent comprises one or more esters of propylene glycol, polyethylene glycol, or combinations thereof. Exemplary propylene and polyethylene glycol based solubilizing agents include glyceryl mono- and di-caprylates; propylene glycol monocaprylate (e.g., CAPMUL® PG-8 or CAPMUL® PG-8 NF); propylene glycol monocaprate (e.g., CAPMUL® PG-10); propylene glycol monolaurate (e.g., CAPMUL® PG-12 EP/NF); propylene glycol mono- and dicaprylates; propylene glycol mono- and dicaprate; propylene glycol dicaprylate/dicaprate (e.g., MIGLYOL® 840); propylene glycol dilaurate (e.g., CAPMUL® PG-2L EP/NF); diethylene glycol mono ester (e.g., TRANSCUTOL®, 2-(2-Ethoxyethoxyl)ethanol, GATTEFOSSÉ SAS, Saint-Priest, France); and diethylene glycol monoethyl ether.

In some embodiments, commercially available fatty acid glycerol and glycol ester solubilizing agents are prepared from natural oils and therefore may comprise components in addition to the fatty acid esters that predominantly comprise and characterize the solubilizing agent. Such other components may be, e.g., other fatty acid mono-, di-, and triglycerides, fatty acid mono- and diester ethylene or propylene glycols, free glycerols or glycols, or free fatty acids. For example, the Technical Data Sheet by ABITEC for CAPMUL® MCM C8 describes CAPMUL® MCM C8 as being composed of mono- and diglycerides of medium chain fatty acids (mainly caprylic) and describes the alkyl content as ≤1% C6, ≥95% C8, ≤5% C10, and ≤1.5% C12 and higher. By way of further example, MIGLYOL® 812 is generally described as a C8-C10 triglyceride because the fatty acid composition is at least about 80% caprylic (C8) acid and capric (C10) acid. However, it can also comprise small amounts of other fatty acids, e.g., less than about 5% of caproic (C6) acid, lauric (C12) acid, and myristic (C14) acid.

In some embodiments, the pharmaceutical composition comprises about 20% to about 85% solubilizing agent by weight, e.g., about 60% to about 85% solubilizing agent by weight. In some embodiments, the composition comprises progesterone, e.g., dissolved and micronized, from about 20 to about 50 wt %, e.g., about 30 to about 35 wt %. In some embodiments, the composition comprises estradiol from about 0.1 to about 0.8 wt %, e.g., about 0.15 to about 0.40 wt %.

Surfactants

In some embodiments, the pharmaceutical composition further comprises one or more non-ionic or ionic surfactants. In some embodiments, the non-ionic surfactant is selected from one or more of glycerol and polyethylene glycol esters of medium chain fatty acids or long chain fatty acids, for example, lauroyl macrogol-32 glycerides or lauroyl polyoxyl-32 glycerides, commercially available as GELUCIRE®, including, for example, GELUCIRE® 39/01 (glycerol esters of saturated C12-C18 fatty acids); GELUCIRE® 43/01 (hard fat NF/JPE); GELUCIRE® 44/14 (lauroyl macrogol-32 glycerides EP, lauroyl polyoxyl-32 glycerides NF, lauroyl polyoxylglycerides (USA FDA IIG)); and GELUCIRE® 50/13 (stearoyl macrogol-32 glycerides EP, stearoyl polyoxyl-32 glycerides NF, stearoyl polyoxylglycerides (USA FDA IIG)).

In some embodiments, non-ionic surfactants comprise combinations of mono- and di-propylene and ethylene glycols and mono-, di-, and triglyceride combinations. For example, in some embodiments, polyethylene glycol glyceride (GELUCIRE®, GATTEFOSSÉ SAS, Saint-Priest, France) can be used herein as the surfactant. For example, GELUCIRE® 44/14 (PEG-32 glyceryl laurate EP), a medium chain fatty acid esters of polyethylene glycol, is a polyethylene glycol glyceride composed of mono-, di- and triglycerides and mono- and diesters of polyethylene glycol.

In some embodiments, non-ionic surfactants include, for example and without limitation: one or more of oleic acid, linoleic acid, palmitic acid, and stearic acid. In some embodiments, non-ionic surfactants comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids.

In some embodiments, non-ionic surfactants include PEG-6 palmitostearate and ethylene glycol palmitostearate, which are available commercially as TEFOSE® 63 (GATTEFOSSÉ SAS, Saint-Priest, France). which can be used with, for example, CAPMUL® MCM having ratios of MCM to TEFOSE® 63 of, for example, 8:2 or 9:1. Other exemplary solubilizing agents/non-ionic surfactants combinations include, without limitation: MIGLYOL® 812:GELUCIRE 50/13 or MIGLYOL® 812:TEFOSE® 63.

A non-ionic or ionic surfactant may be used at concentrations greater than about 0.01%, for example at a concentration of about 0.01%-10.0%, about 0.1% to 10.0%, or about 1% to 10.0%. In some embodiments, the pharmaceutical composition comprises about 10.0% surfactant by weight. In some embodiments, the pharmaceutical composition comprises about 0.1% to about 5.0% surfactant by weight, e.g., about 1.0 wt %.

Other Excipients

In some embodiments, the pharmaceutical composition further comprises one more other excipients, such as but not limited to colorants, flavoring agents, preservatives, and taste-masking agents. The choice of excipients will, to a large extent, depend on factors such as the particular mode of administration, the effect of the excipients on solubility and stability, and the nature of the dosage form. Colorants, for example, may comprise about 0.1% to about 2% by weight. Preservatives may comprise methyl and propyl paraben, for example, in a ratio of about 10:1, and at a proportion of about 0.005% and 0.05% by weight.

Generally, the solubilizing agents, surfactants, and excipients used in the pharmaceutical compositions described herein are non-toxic, pharmaceutically acceptable, compatible with each other, and maintain stability of the pharmaceutical composition and the various components with respect to each other. Additionally, the combination of various components that comprise the pharmaceutical compositions will maintain will result in the desired therapeutic effect when administered to a subject.

Formulation

In some embodiments, combinations of solubilizing agents (e.g., two or more oils) or combinations of one or more solubilizing agents and one or more surfactants are used to form estradiol and progesterone compositions. Various ratios of these solubilizing agents or solubilizing agents and surfactants can be used. For example, CAPMUL® MCM and a non-ionic surfactant, e.g., GELUCIRE® 44/14 (lauroyl macrogol-32 glycerides EP; lauroyl polyoxyl-32 glycerides NF; lauroyl polyoxylglycerides (USA FDA IIG)), can be used at ratios of about 99:1 to about 2:1, including, for example and without limitation: 60:40, 65:35, 70:30, 75:25, 80:10, 80:15, 85:20, 90:10, and 98:1. As another example, CAPMUL® MCM and a non-ionic surfactant, e.g., TEFOSE® 63, can be used as rations of about 8:2 or 9:1. Other exemplary solubilizing agent/surfactant combinations include, without limitation: MIGLYOL® 812:GELUCIRE® 50/13 or MIGLYOL® 812:TEFOSE® 63. The ratios of oil (e.g., medium chain fatty acid esters of monoglycerides and diglycerides) to non-ionic surfactant can be significantly higher. For example, CAPMUL® MCM and GELUCIRE® can be used in ratios of up to about 65:1, e.g., 8:1, 22:1, 49:1, 65:1 and 66:1. Thus, useful ratios can be 8:1 or greater, e.g., 60 to 70:1.

In some embodiments, estradiol or progesterone is soluble in the solubilizing agent at room temperature, although it may be desirable to warm certain solubilizing agents. For example, when the formulation comprises medium chain fatty acid mono- and diglycerides (e.g., CAPMUL® MCM) and polyethylene glycol glycerides (e.g., GELUCIRE®) as a surfactant, the oil or the surfactant can be warmed up, e.g., to about 65° C. for the surfactant and less for the oil, to facilitate mixing of the oil and surfactant. The estradiol can be added at this temperature, or at lower temperatures as the mixture cools, e.g., about 40° C. or about 30° C., or even after the mixture has cooled to room temperature. The progesterone can also be added as the mixture cools, e.g., to below about 40° C. or to below about 30° C., or after the mixture has cooled to room temperature.

As a non-limiting example, a composition of this disclosure comprises solubilized estradiol; progesterone, at least 30% (e.g., at least about 30%, about 40%, about 50%, about 60%, about 70%, about 75%, about 80%, about 85%, or more) of the progesterone being solubilized (the balance being micronized as discussed elsewhere herein); and a solubilizing agent that is an oil, wherein the oil comprises medium chain fatty acid mono-, di-, or triglycerides, with or without a surfactant. In certain embodiments, a specification for progesterone is set at >80% solubilized, <20% micronized or >85% solubilized, <15% micronized. Specific examples of such illustrative embodiments, with CAPMUL® MCM NF (glyceryl caprylate/caprate) as a solubilizing agent and GELUCIRE® 44/14 (lauroyl polyoxyglyceride) as a surfactant, in which at least about 85% of the progesterone can be solubilized, include, e.g., the following five formulations A-E:

TABLE 1

Pharmaceutical Composition A - progesterone 50 mg/estradiol 0.25 mg

| Ingredient | Amount (% w/w) | Qty/Capsule (mg) |
|---|---|---|
| Progesterone, USP, micronized | 33.33 | 50.00 |
| Estradiol Hemihydrate | 0.17 | 0.26 |
| CAPMUL ® MCM, NF | 65.49 | 98.24 |
| GELUCIRE ® 44/14, NF | 1.00 | 1.50 |
| Total | 100.00 | 150.00 |

TABLE 2

Pharmaceutical Composition B - progesterone 50 mg/estradiol 0.5 mg

| Ingredient | Amount (% w/w) | Qty/Capsule (mg) |
|---|---|---|
| Progesterone, USP, micronized | 33.33 | 50.00 |
| Estradiol Hemihydrate | 0.35 | 0.52 |
| CAPMUL ® MCM, NF | 65.32 | 97.98 |
| GELUCIRE ® 44/14, NF | 1.00 | 1.50 |
| Total | 100.00 | 150.00 |

TABLE 3

Pharmaceutical Composition C - progesterone 100 mg/estradiol 0.5 mg

| Ingredient | Amount (% w/w) | Qty/Capsule (mg) |
|---|---|---|
| Progesterone, USP, micronized | 33.33 | 100.00 |
| Estradiol Hemihydrate | 0.17 | 0.52 |
| CAPMUL ® MCM, NF | 65.49 | 196.48 |
| GELUCIRE ® 44/14, NF | 1.00 | 3.00 |
| Total | 100.00 | 300.00 |

TABLE 4

Pharmaceutical Composition D - progesterone 100 mg/estradiol 1 mg

| Ingredient | Amount (% w/w) | Qty/Capsule (mg) |
|---|---|---|
| Progesterone, USP, micronized | 33.33 | 100.00 |
| Estradiol Hemihydrate | 0.34 | 1.03 |
| CAPMUL ® MCM, NF | 65.32 | 195.97 |
| GELUCIRE ® 44/14, NF | 1.00 | 3.00 |
| Total | 100.00 | 300.00 |

*Note:
1.00 mg Estradiol is equivalent to 1.03 mg Estradiol Hemihydrate

TABLE 5

Pharmaceutical Composition E - progesterone 200 mg/estradiol 2 mg

| Ingredient | Amount (% w/w) | Qty/Capsule (mg) |
|---|---|---|
| Progesterone, USP, micronized | 33.33 | 200.00 |
| Estradiol Hemihydrate | 0.34 | 2.06 |
| CAPMUL ® MCM, NF | 65.32 | 391.94 |
| GELUCIRE ® 44/14, NF | 1.00 | 6.00 |
| Total | 100.00 | 600.00 |

In general terms, the above formulations comprise 30 to 35 wt % progesterone, 0.1 to 0.4 wt % estradiol (or estradiol hemihydrate), 55 to 75 wt % of an oil that is predominantly medium chain fatty acid mono-, di-, or triglycerides, such as CAPMUL® MCM, and 0.5 to 10 wt % of a non-ionic surfactant, such as GELUCIRE® 44/14. The above formulations may be modified to comprise excipients, e.g., gelatin such as Gelatin 200 Bloom, glycerin, coloring agents such as Opatint red and white, and, optionally, MIGLYOL® 812.

Estradiol solubilization helps ensure high content uniformity and enhanced stability. Fully solubilized progesterone formulations or partially solubilized progesterone formulations in which at least about 50% of the progesterone, e.g., at least about 50%, 60%, 70%, 75%, 80%, 85%, 90%, 95% or more, is solubilized appear to provide improved PK-related properties.

Pharmacokinetic Parameters of Estradiol and Progesterone Compositions

The pharmaceutical compositions of this disclosure can be formulated to provide desirable pharmacokinetic parameters in a subject (e.g., a female subject) to whom the composition is administered. In some embodiments, a pharmaceutical composition as described herein produces desirable pharmacokinetic parameters for progesterone in the subject. In some embodiments, a pharmaceutical composition as described herein produces desirable pharmacokinetic parameters for estradiol in the subject. In some embodiments, a pharmaceutical composition as described herein produces desirable pharmacokinetic parameters for one or more metabolites of progesterone or estradiol in the subject, for example, estrone or total estrone.

Following the administration of a composition comprising progesterone and estradiol to a subject, the concentration and metabolism of progesterone or estradiol can be measured in a sample (e.g., a blood, serum, or plasma sample) from the subject. Progesterone is metabolized to pregnanediols and pregnanolones, which are then conjugated to glucuronide and sulfate metabolites that are excreted or further recycled. Estradiol is converted reversibly to estrone, and both estradiol and estrone can be converted to the metabolite estriol. In postmenopausal women, a significant proportion of circulating estrogens exist as sulfate conjugates, especially estrone sulfate. Thus, estrone can be measured with respect to "estrone" amounts (excluding conjugates such as estrone sulfate) and "total estrone" amounts (including both free, or unconjugated, estrone and conjugated estrone such as estrone sulfate).

The pharmaceutical compositions of this disclosure can be characterized for one or more pharmacokinetic parameters of progesterone, estradiol, or a metabolite thereof following administration of the composition to a subject or to a population of subjects. These pharmacokinetic parameters include AUC, $C_{max}$, and $T_{max}$. AUC is a determination of the area under the curve (AUC) plotting the blood, serum, or plasma concentration of drug along the ordinate (Y-axis) against time along the abscissa (X-axis). AUCs are well understood, frequently used tools in the pharmaceutical arts and have been extensively described. $C_{max}$ is well understood in the art as an abbreviation for the maximum drug concentration in blood, serum, or plasma of a subject. $T_{max}$ is well understood in the art as an abbreviation for the time to maximum drug concentration in blood, serum, or plasma of a subject.

In some embodiments, one or more pharmacokinetic parameters, e.g., AUC, $C_{max}$, or $T_{max}$, is measured for estradiol. In some embodiments, one or more pharmacokinetic parameters, e.g., AUC, $C_{max}$, or $T_{max}$, is measured for progesterone. In some embodiments, one or more pharmacokinetic parameters, e.g., AUC, $C_{max}$, or $T_{max}$, is measured for estrone. In some embodiments, one or more pharmacokinetic parameters, e.g., AUC, $C_{max}$, or $T_{max}$, is measured for total estrone.

Any of a variety of methods can be used for measuring the levels of progesterone, estradiol, estrone, or total estrone in a sample, including immunoassays, mass spectrometry (MS), high performance liquid chromatography (HPLC) with ultraviolet fluorescent detection, liquid chromatography in conjunction with mass spectrometry (LC-MS), tandem mass spectrometry (MS/MS), and liquid chromatography-tandem mass spectrometry (LC-MS/MS). In some embodiments, the levels of progesterone, estradiol, estrone, or total estrone are measured using a validated LC-MS/MS method. Methods of measuring hormone levels are well described in the literature.

The levels of progesterone, estradiol, estrone, or total estrone can be measured in any biological sample, e.g. a tissue or fluid such as blood, serum, plasma, or urine. In some embodiments, the sample is blood or plasma. In some embodiments, the levels of progesterone, estradiol, estrone, or total estrone are measured about 0.0, 0.10, 0.20, 0.05, 0.30, 0.35, 0.40, 0.45, 0.5, 1, 2, 3, 4, 5, 6, 7, 8, 9, 10, 12, 15, 18, 21, 24, 27, 30, 33, 36, 39, 42, 45, or 48 hours after dosing, or any other appropriate time period that is common or useful in determining the levels of each of the hormones. In some embodiments, the levels of progesterone, estradiol, estrone, or total estrone are measured about 18 hours, about 24 hours, about 18-36 hours, about 20-30 hours, about 22-26 hours, about 24-36 hours, about 36 hours, about 36-48 hours, about 40-48 hours, or about 48 hours after administration of a single dose or a first dose. Generally, assays to determine the levels of progesterone, estradiol, estrone, or total estrone are measured one or more times every 5, 10, 15, 20, 30, 60, 120, 360, 480, 720, or 1440 minutes after administration, or combinations thereof (e.g., the first measurements are taken every 15 minutes for the first hour, followed by every 120 minutes thereafter). In embodiments, the timing of such measurements are designed to accurately measure $C_{max}$, $T_{max}$, or AUC. Timing can be adjusted based on the given circumstances (i.e., one formulation may cause a more rapid $C_{max}$, in which case the initial times would be clustered closer together, closer to time zero, or both to ensure accurate measurement of $C_{max}$, $T_{max}$, and AUC). In some embodiments, the $C_{max}$, $T_{max}$, or AUC values for progesterone, estradiol, estrone, or total estrone are measured following administration of a single dose of a pharmaceutical composition as described herein.

In some embodiments, the values for $C_{max}$, $T_{max}$, or AUC represent a number of values taken from all the subjects in a patient population and are, therefore, mean values (e.g., arithmetic or geometric means) averaged over the entire population.

In some embodiments, oral administration of a pharmaceutical composition comprising estradiol, progesterone, and a medium chain solubilizing agent as described herein to a subject, or to a population of subjects, produces one or more AUC, $C_{max}$, or $T_{max}$ parameters, or one or more mean AUC, mean $C_{max}$, or mean $T_{max}$ parameters, respectively, for estradiol, progesterone, estrone, or total estrone as described below.

AUC $C_{max}$, and $T_{max}$ Parameters (A)

In some embodiments, a pharmaceutical composition of this disclosure comprises estradiol at a dosage of about 0.25 mg and progesterone at a dosage of about 50 mg. In some embodiments, the pharmaceutical composition comprises the formulation of Formulation A in Table 1 above.

In some embodiments, administration of a composition comprising about 0.25 mg estradiol and about 50 mg progesterone to a subject produces, in a plasma sample from the subject, one or both parameters selected from:
 (i) an $AUC_{(0-t)}$ for estradiol that is from 140.3733 pg·hr/ml to 219.3333 pg·hr/ml; or
 (ii) a $C_{max}$ for estradiol that is from 6.4790 pg/ml to 10.1235 pg/ml.

In some embodiments, administration of the composition to the subject produces both an $AUC_{(0-t)}$ for estradiol that is from 140.3733 pg·hr/ml to 219.3333 pg·hr/ml, and a $C_{max}$ for estradiol that is from 6.4790 pg/ml to 10.1235 pg/ml.

In some embodiments, administration of the composition to the subject further produces, in a plasma sample from the subject, one or both parameters selected from:
 (i) an $AUC_{(0-t)}$ for progesterone that is from 24.0174 ng·hr/ml to 37.5272 ng·hr/ml; or
 (ii) a $C_{max}$ for progesterone that is from 17.8444 ng/ml to 27.8819 ng/ml.

In some embodiments, administration of the composition to the subject produces both an $AUC_{(0-t)}$ for progesterone that is from 24.0174 ng·hr/ml to 37.5272 ng·hr/ml, and a $C_{max}$ for progesterone that is from 17.8444 ng/ml to 27.8819 ng/ml.

In some embodiments, administration of the composition to the subject produces, in a plasma sample from the subject,
(i) an $AUC_{(0-t)}$ for estradiol that is from 140.3733 pg·hr/ml to 219.3333 pg·hr/ml;
(ii) a $C_{max}$ for estradiol that is from 6.4790 pg/ml to 10.1235 pg/ml;
(iii) an $AUC_{(0-t)}$ for progesterone that is from 24.0174 ng·hr/ml to 37.5272 ng·hr/ml; or
(iv) a $C_{max}$ for progesterone that is from 17.8444 ng/ml to 27.8819 ng/ml.

In some embodiments, administration of the composition to the subject further produces, in a plasma sample from the subject, a $T_{max}$ for estradiol that is from 7.2 hr to 11.3 hr. In some embodiments, administration of the composition to the subject further produces, in a plasma sample from the subject, a $T_{max}$ for progesterone that is from 2.4 hr to 3.8 hr.

In some embodiments, administration of the pharmaceutical composition to the subject produces, in a plasma sample from the subject, one, two, three or more parameters selected from:
(i) an $AUC_{(0-t)}$ for estradiol that is from 140.3733 pg·hr/ml to 219.3333 pg·hr/ml;
(ii) a $C_{max}$ for estradiol that is from 6.4790 pg/ml to 10.1235 pg/ml;
(iii) an $AUC_{(0-t)}$ for progesterone that is from 24.0174 ng·hr/ml to 37.5272 ng·hr/ml; or
(iv) a $C_{max}$ for progesterone that is from 17.8444 ng/ml to 27.8819 ng/ml.

In some embodiments, administration of the pharmaceutical composition to the subject produces both parameters (i) and (ii). In some embodiments, administration of the composition to the subject produces both parameters (i) and (iii). In some embodiments, administration of the composition to the subject produces both parameters (i) and (iv). In some embodiments, administration of the composition to the subject produces both parameters (ii) and (iii). In some embodiments, administration of the composition to the subject produces both parameters (ii) and (iv). In some embodiments, administration of the composition to the subject produces both parameters (iii) and (iv). In some embodiments, administration of the composition to the subject produces all of parameters (i), (ii), and (iii). In some embodiments, administration of the composition to the subject produces both parameters (i), (iii), and (iv). In some embodiments, administration of the composition to the subject produces both parameters (ii), (iii), and (iv). In some embodiments, administration of the composition to the subject produces all of parameters (i), (ii), (iii), and (iv).

In some embodiments, administration of the pharmaceutical composition to the subject further produces, in a plasma sample from the subject, one or more parameters selected from:
(i) an $AUC_{(0-t)}$ for estrone that is from 909.6091 pg·hr/ml to 1421.2642 pg·hr/ml;
(ii) a $C_{max}$ for estrone that is from 42.6549 pg/ml to 66.6483 pg/ml; or
(iii) a $T_{max}$ for estrone that is from 4.4 hr to 6.9 hr.

In some embodiments, administration of the pharmaceutical composition to the subject further produces, in a plasma sample from the subject, one or more parameters selected from:
(i) an $AUC_{(0-t)}$ for total estrone that is from 20.1752 ng·hr/ml to 31.5238 ng·hr/ml;
(ii) a $C_{max}$ for total estrone that is from 3.5429 ng/ml to 5.5358 ng/ml; or
(iii) a $T_{max}$ for total estrone that is from 2 hr to 3.1 hr.

In some embodiments, a pharmaceutical composition comprising about 0.25 mg estradiol and about 50 mg progesterone is administered to a population of subjects in need thereof, and mean parameters are determined for samples (e.g., blood or plasma samples) from the subjects administered the composition. Thus, in some embodiments, administration of the composition to a population of subject produces, in plasma samples from the subjects, one or more of a mean $AUC_{(0-t)}$ for estradiol that is from 140.3733 pg·hr/ml to 219.3333 pg·hr/ml, a mean $C_{max}$ for estradiol that is from 6.4790 pg/ml to 10.1235 pg/ml, and a mean $T_{max}$ for estradiol that is from 7.2 hr to 11.3 hr. In some embodiments, administration of the composition to a population of subject produces, in plasma samples from the subjects, one or more of a mean $AUC_{(0-t)}$ for progesterone that is from 24.0174 ng·hr/ml to 37.5272 ng·hr/ml, a mean $C_{max}$ for progesterone that is from 17.8444 ng/ml to 27.8819 ng/ml, and a mean $T_{max}$ for progesterone that is from 2.4 hr to 3.8 hr. In some embodiments, administration of the composition to a population of subject produces, in plasma samples from the subjects, one or more of a mean $AUC_{(0-t)}$ for estrone that is from 909.6091 pg·hr/ml to 1421.2642 pg·hr/ml, a mean $C_{max}$ for estrone that is from 42.6549 pg/ml to 66.6483 pg/ml, and a mean $T_{max}$ for estrone that is from 4.4 hr to 6.9 hr. In some embodiments, administration of the composition to a population of subject produces, in plasma samples from the subjects, one or more of a mean $AUC_{(0-t)}$ for total estrone that is from 20.1752 ng·hr/ml to 31.5238 ng·hr/ml, a mean $C_{max}$ for total estrone that is from 3.5429 ng/ml to 5.5358 ng/ml, and a mean $T_{max}$ for total estrone that is from 2 hr to 3.1 hr.

In some embodiments, methods of treating a subject with a pharmaceutical composition comprising estradiol and progesterone are provided. In some embodiments, the method comprises administering to the subject a pharmaceutical composition comprising about 0.25 mg estradiol and about 50 mg progesterone as described herein (e.g., a pharmaceutical composition having the formulation of Formulation A in Table 1 above), wherein administration of the pharmaceutical composition produces, in a plasma sample from the subject, one or more parameters selected from: an $AUC_{(0-t)}$ for estradiol that is from 140.3733 pg·hr/ml to 219.3333 pg·hr/ml; a $C_{max}$ for estradiol that is from 6.4790 pg/ml to 10.1235 pg/ml; a $T_{max}$ for estradiol that is from 7.2 hr to 11.3 hr; an $AUC_{(0-t)}$ for progesterone that is from 24.0174 ng·hr/ml to 37.5272 ng·hr/ml; a $C_{max}$ for progesterone that is from 17.8444 ng/ml to 27.8819 ng/ml; a $T_{max}$ for progesterone that is from 2.4 hr to 3.8 hr; an $AUC_{(0-t)}$ for estrone that is from 909.6091 pg·hr/ml to 1421.2642 pg·hr/ml; a $C_{max}$ for estrone that is from 42.6549 pg/ml to 66.6483 pg/ml; a $T_{max}$ for estrone that is from 4.4 hr to 6.9 hr; an $AUC_{(0-t)}$ for total estrone that is from 20.1752 ng·hr/ml to 31.5238 ng·hr/ml; a $C_{max}$ for total estrone that is from 3.5429 ng/ml to 5.5358 ng/ml; and a $T_{max}$ for total estrone that is from 2 hr to 3.1 hr.

In some embodiments, the method further comprises obtaining a sample from the subject (e.g., a blood or plasma sample) following administration of a single dose of the pharmaceutical composition (e.g., a pharmaceutical composition having the formulation of Formulation A in Table 1 above), and measuring one or more pharmacokinetic parameters selected from an $AUC_{(0-t)}$ for estradiol, a $C_{max}$ for estradiol, an $AUC_{(0-t)}$ for progesterone, a $C_{max}$ for progesterone, an $AUC_{(0-t)}$ for estrone, a $C_{max}$ for estrone, an $AUC_{(0-t)}$ for total estrone, and a $C_{max}$ for total estrone;

wherein the presence of one or more of the following values is indicative of a therapeutically effective dose: an $AUC_{(0-t)}$ for estradiol that is from 140.3733 pg·hr/ml to 219.3333 pg·hr/ml; a $C_{max}$ for estradiol that is from 6.4790 pg/ml to 10.1235 pg/ml; an $AUC_{(0-t)}$ for progesterone that is from 24.0174 ng·hr/ml to 37.5272 ng·hr/ml; a $C_{max}$ for progesterone that is from 17.8444 ng/ml to 27.8819 ng/ml; an $AUC_{(0-t)}$ for estrone that is from 909.6091 pg·hr/ml to 1421.2642 pg·hr/ml; a $C_{max}$ for estrone that is from 42.6549 pg/ml to 66.6483 pg/ml; an $AUC_{(0-t)}$ for total estrone that is from 20.1752 ng·hr/ml to 31.5238 ng·hr/ml; or a $C_{max}$ for total estrone that is from 3.5429 ng/ml to 5.5358 ng/ml. In some embodiments, the one or more pharmacokinetic parameters are measured about 18 hours, about 24 hours, about 18-36 hours, about 20-30 hours, about 22-26 hours, about 24-36 hours, about 36 hours, about 36-48 hours, about 40-48 hours, or about 48 hours after administration of the single dose.

AUC, $C_{max}$, and $T_{max}$ Parameters (B)

In some embodiments, a pharmaceutical composition of this disclosure comprises estradiol at a dosage of about 0.50 mg and progesterone at a dosage of about 50 mg. In some embodiments, the pharmaceutical composition comprises the formulation of Formulation B in Table 2 above.

In some embodiments, administration of a composition comprising about 0.50 mg estradiol and about 50 mg progesterone to a subject produces, in a plasma sample from the subject, one or both parameters selected from:
 (i) an $AUC_{(0-t)}$ for estradiol that is from 280.7467 pg·hr/ml to 438.6667 pg·hr/ml; or
 (ii) a $C_{max}$ for estradiol that is from 12.9580 pg/ml to 20.2469 pg/ml.

In some embodiments, administration of the composition to the subject produces both an $AUC_{(0-t)}$ for estradiol that is from 280.7467 pg·hr/ml to 438.6667 pg·hr/ml, and a $C_{max}$ for estradiol that is from 12.9580 pg/ml to 20.2469 pg/ml.

In some embodiments, administration of the composition to the subject further produces, in a plasma sample from the subject, one or both parameters selected from:
 (i) an $AUC_{(0-t)}$ for progesterone that is from 24.0174 ng·hr/ml to 37.5272 ng·hr/ml; or
 (ii) a $C_{max}$ for progesterone that is from 17.8444 ng/ml to 27.8819 ng/ml.

In some embodiments, administration of the composition to the subject produces both an $(AUC)_{(0-t)}$ for progesterone that is from 24.0174 ng·hr/ml to 37.5272 ng·hr/ml, and a $C_{max}$ for progesterone that is from 17.8444 ng/ml to 27.8819 ng/ml.

In some embodiments, administration of the composition to the subject produces, in a plasma sample from the subject,
 (i) an $AUC_{(0-t)}$ for estradiol that is from 280.7467 pg·hr/ml to 438.6667 pg·hr/ml;
 (ii) a $C_{max}$ for estradiol that is from 12.9580 pg/ml to 20.2469 pg/ml;
 (iii) an $AUC_{(0-t)}$ for progesterone that is from 24.0174 ng·hr/ml to 37.5272 ng·hr/ml; or
 (iv) a $C_{max}$ for progesterone that is from 17.8444 ng/ml to 27.8819 ng/ml.

In some embodiments, administration of the composition to the subject further produces, in a plasma sample from the subject, a $T_{max}$ for estradiol that is from 7.2 hr to 11.3 hr. In some embodiments, administration of the composition to the subject further produces, in a plasma sample from the subject, a $T_{max}$ for progesterone that is from 2.4 hr to 3.8 hr.

In some embodiments, administration of the pharmaceutical composition to the subject produces, in a plasma sample from the subject, one, two, three or more parameters selected from:
 (i) an $AUC_{(0-t)}$ for estradiol that is from 280.7467 pg·hr/ml to 438.6667 pg·hr/ml;
 (ii) a $C_{max}$ for estradiol that is from 12.9580 pg/ml to 20.2469 pg/ml;
 (iii) an $AUC_{(0-t)}$ for progesterone that is from 24.0174 ng·hr/ml to 37.5272 ng·hr/ml; or
 (iv) a $C_{max}$ for progesterone that is from 17.8444 ng/ml to 27.8819 ng/ml.

In some embodiments, administration of the pharmaceutical composition to the subject produces both parameters (i) and (ii). In some embodiments, administration of the composition to the subject produces both parameters (i) and (iii). In some embodiments, administration of the composition to the subject produces both parameters (i) and (iv). In some embodiments, administration of the composition to the subject produces both parameters (ii) and (iii). In some embodiments, administration of the composition to the subject produces both parameters (ii) and (iv). In some embodiments, administration of the composition to the subject produces both parameters (iii) and (iv). In some embodiments, administration of the composition to the subject produces all of parameters (i), (ii), and (iii). In some embodiments, administration of the composition to the subject produces both parameters (i), (iii), and (iv). In some embodiments, administration of the composition to the subject produces both parameters (ii), (iii), and (iv). In some embodiments, administration of the composition to the subject produces all of parameters (i), (ii), (iii), and (iv).

In some embodiments, administration of the pharmaceutical composition to the subject further produces, in a plasma sample from the subject, one or more parameters selected from:
 (i) an $AUC_{(0-t)}$ for estrone that is from 1819.2181 pg·hr/ml to 2842.5283 pg·hr/ml;
 (ii) a $C_{max}$ for estrone that is from 85.3098 pg/ml to 133.2966 pg/ml; or
 (iii) a $T_{max}$ for estrone that is from 4.4 hr to 6.9 hr.

In some embodiments, administration of the pharmaceutical composition to the subject further produces, in a plasma sample from the subject, one or more parameters selected from:
 (i) an $AUC_{(0-t)}$ for total estrone that is from 40.3505 ng·hr/ml to 63.0476 ng·hr/ml;
 (ii) a $C_{max}$ for total estrone that is from 7.0858 ng/ml to 11.0715 ng/ml; or
 (iii) a $T_{max}$ for total estrone that is from 2 hr to 3.1 hr.

In some embodiments, a pharmaceutical composition comprising about 0.50 mg estradiol and about 50 mg progesterone is administered to a population of subjects in need thereof, and mean parameters are determined for samples (e.g., blood or plasma samples) from the subjects administered the composition. Thus, in some embodiments, administration of the composition to a population of subject produces, in plasma samples from the subjects, one or more of a mean $AUC_{(0-t)}$ for estradiol that is from 280.7467 pg·hr/ml to 438.6667 pg·hr/ml, a mean $C_{max}$ for estradiol that is from 12.9580 pg/ml to 20.2469 pg/ml, and a mean $T_{max}$ for estradiol that is from 7.2 hr to 11.3 hr. In some embodiments, administration of the composition to a population of subject produces, in plasma samples from the subjects, one or more of a mean $AUC_{(0-t)}$ for progesterone that is from 24.0174 ng·hr/ml to 37.5272 ng·hr/ml, a mean $C_{max}$ for progesterone that is from 17.8444 ng/ml to 27.8819 ng/ml, and a mean $T_{max}$ for progesterone that is from 2.4 hr to 3.8 hr. In some embodiments, administration of the composition to a population of subject produces, in plasma samples from the subjects, one or more of a mean $AUC_{(0-t)}$ for estrone that is from 1819.2181 pg·hr/ml to 2842.5283 pg·hr/ml, a mean $C_{max}$ for estrone that is from 85.3098 pg/ml to 133.2966 pg/ml, and a mean $T_{max}$ for estrone that is from 4.4 hr to 6.9 hr. In some embodiments, administration of the composition to a population of subject produces, in plasma samples from the subjects, one or more of a mean $AUC_{(0-t)}$ for total estrone that is from 40.3505 ng·hr/ml to 63.0476 ng·hr/ml, a mean $C_{max}$ for total estrone that is from 7.0858 ng/ml to 11.0715 ng/ml, and a mean $T_{max}$ for total estrone that is from 2 hr to 3.1 hr.

In some embodiments, methods of treating a subject with a pharmaceutical composition comprising estradiol and progesterone are provided. In some embodiments, the method comprises administering to the subject a pharmaceutical composition comprising about 0.50 mg estradiol and about 50 mg progesterone as described herein (e.g., a pharmaceutical composition having the formulation of Formulation B in Table 2 above), wherein administration of the pharmaceutical composition produces, in a plasma sample from the subject, one or more parameters selected from: an $AUC_{(0-t)}$ for estradiol that is from 280.7467 pg·hr/ml to 438.6667 pg·hr/ml; a $C_{max}$ for estradiol that is from 12.9580 pg/ml to 20.2469 pg/ml; a $T_{max}$ for estradiol that is from 7.2 hr to 11.3 hr; an $AUC_{(0-t)}$ for progesterone that is from 24.0174 ng·hr/ml to 37.5272 ng·hr/ml; a $C_{max}$ for progesterone that is from 17.8444 ng/ml to 27.8819 ng/ml; a $T_{max}$ for progesterone that is from 2.4 hr to 3.8 hr; an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; a $T_{max}$ for estrone that is from 4.4 hr to 6.9 hr; an $AUC_{(0-t)}$ for total estrone that is from 40.3505 ng·hr/ml to 63.0476 ng·hr/ml; a $C_{max}$ for total estrone that is from 7.0858 ng/ml to 11.0715 ng/ml; and a $T_{max}$ for total estrone that is from 2 hr to 3.1 hr.

In some embodiments, the method further comprises obtaining a sample from the subject (e.g., a blood or plasma sample) following administration of a single dose of the pharmaceutical composition (e.g., a pharmaceutical composition having the formulation of Formulation B in Table 2 above), and measuring one or more pharmacokinetic parameters selected from an $AUC_{(0-t)}$ for estradiol, a $C_{max}$ for estradiol, an $AUC_{(0-t)}$ for progesterone, a $C_{max}$ for progesterone, an $AUC_{(0-t)}$ for estrone, a $C_{max}$ for estrone, an $AUC_{(0-t)}$ for total estrone, and a $C_{max}$ for total estrone; wherein the presence of one or more of the following values is indicative of a therapeutically effective dose: an $AUC_{(0-t)}$ for estradiol that is from 280.7467 pg·hr/ml to 438.6667 pg·hr/ml; a $C_{max}$ for estradiol that is from 12.9580 pg/ml to 20.2469 pg/ml; an $AUC_{(0-t)}$ for progesterone that is from 24.0174 ng·hr/ml to 37.5272 ng·hr/ml; a $C_{max}$ for progesterone that is from 17.8444 ng/ml to 27.8819 ng/ml; an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; an $AUC_{(0-t)}$ for total estrone that is from 40.3505 ng·hr/ml to 63.0476 ng·hr/ml; and a $C_{max}$ for total estrone that is from 7.0858 ng/ml to 11.0715 ng/ml. In some embodiments, the one or more pharmacokinetic parameters are measured about 18 hours, about 24 hours, about 18-36 hours, about 20-30 hours, about 22-26 hours, about 24-36 hours, about 36 hours, about 36-48 hours, about 40-48 hours, or about 48 hours after administration of the single dose.

AUC, $C_{max}$, and $T_{max}$ Parameters (C)

In some embodiments, a pharmaceutical composition of this disclosure comprises estradiol at a dosage of about 0.50 mg and progesterone at a dosage of about 100 mg. In some embodiments, the pharmaceutical composition comprises the formulation of Formulation C in Table 3 above.

In some embodiments, administration of a composition comprising about 0.50 mg estradiol and about 100 mg progesterone to a subject produces, in a plasma sample from the subject, one or both parameters selected from:
 (i) an $AUC_{(0-t)}$ for estradiol that is from 280.7467 pg·hr/ml to 438.6667 pg·hr/ml; or
 (ii) a $C_{max}$ for estradiol that is from 12.9580 pg/ml to 20.2469 pg/ml.

In some embodiments, administration of the composition to the subject produces both an $AUC_{(0-t)}$ for estradiol that is from 280.7467 pg·hr/ml to 438.6667 pg·hr/ml, and a $C_{max}$ for estradiol that is from 12.9580 pg/ml to 20.2469 pg/ml.

In some embodiments, administration of the composition to the subject further produces, in a plasma sample from the subject, one or both parameters selected from:
 (i) an $AUC_{(0-t)}$ for progesterone that is from 48.0348 ng·hr/ml to 75.0543 ng·hr/ml; or
 (ii) a $C_{max}$ for progesterone that is from 35.6889 ng/ml to 55.7639 ng/ml.

In some embodiments, administration of the composition to the subject produces both an $AUC_{(0-t)}$ for progesterone that is from 48.0348 ng·hr/ml to 75.0543 ng·hr/ml, and a $C_{max}$ for progesterone that is from 35.6889 ng/ml to 55.7639 ng/ml.

In some embodiments, administration of the composition to the subject produces, in a plasma sample from the subject,
 (i) an $AUC_{(0-t)}$ for estradiol that is from 280.7467 pg·hr/ml to 438.6667 pg·hr/ml;
 (ii) a $C_{max}$ for estradiol that is from 12.9580 pg/ml to 20.2469 pg/ml;
 (iii) an $AUC_{(0-t)}$ for progesterone that is from 48.0348 ng·hr/ml to 75.0543 ng·hr/ml; or
 (iv) a $C_{max}$ for progesterone that is from 35.6889 ng/ml to 55.7639 ng/ml.

In some embodiments, administration of the composition to the subject further produces, in a plasma sample from the subject, a $T_{max}$ for estradiol that is from 7.2 hr to 11.3 hr. In some embodiments, administration of the composition to the subject further produces, in a plasma sample from the subject, a $T_{max}$ for progesterone that is from 2.4 hr to 3.8 hr.

In some embodiments, administration of the pharmaceutical composition to the subject produces, in a plasma sample from the subject, one or more parameters selected from:
 (i) an $AUC_{(0-t)}$ for estradiol that is from 280.7467 pg·hr/ml to 438.6667 pg·hr/ml;
 (ii) a $C_{max}$ for estradiol that is from 12.9580 pg/ml to 20.2469 pg/ml;
 (iii) an $AUC_{(0-t)}$ for progesterone that is from 48.0348 ng·hr/ml to 75.0543 ng·hr/ml; or
 (iv) a $C_{max}$ for progesterone that is from 35.6889 ng/ml to 55.7639 ng/ml.

In some embodiments, administration of the pharmaceutical composition to the subject produces both parameters (i) and (ii). In some embodiments, administration of the composition to the subject produces both parameters (i) and (iii). In some embodiments, administration of the composition to the subject produces both parameters (i) and (iv). In some embodiments, administration of the composition to the subject produces both parameters (ii) and (iii). In some embodiments, administration of the composition to the subject produces both parameters (ii) and (iv). In some embodiments, administration of the composition to the subject produces both parameters (iii) and (iv). In some embodiments, administration of the composition to the subject produces all of parameters (i), (ii), and (iii). In some embodiments, administration of the composition to the subject produces both parameters (i), (iii), and (iv). In some embodiments, administration of the composition to the subject produces both parameters (ii), (iii), and (iv). In some embodiments, administration of the composition to the subject produces all of parameters (i), (ii), (iii), and (iv).

In some embodiments, administration of the pharmaceutical composition to the subject further produces, in a plasma sample from the subject, one, two, three or more parameters selected from:
  (i) an $AUC_{(0-t)}$ for estrone that is from 1819.2181 pg·hr/ml to 2842.5283 pg·hr/ml;
  (ii) a $C_{max}$ for estrone that is from 85.3098 pg/ml to 133.2966 pg/ml; or
  (iii) a $T_{max}$ for estrone that is from 4.4 hr to 6.9 hr.

In some embodiments, administration of the pharmaceutical composition to the subject further produces, in a plasma sample from the subject, one or more parameters selected from:
  (i) an $AUC_{(0-t)}$ for total estrone that is from 40.3505 ng·hr/ml to 63.0476 ng·hr/ml;
  (ii) a $C_{max}$ for total estrone that is from 7.0858 ng/ml to 11.0715 ng/ml; or
  (iii) a $T_{max}$ for total estrone that is from 2 hr to 3.1 hr.

In some embodiments, a pharmaceutical composition comprising about 0.50 mg estradiol and about 100 mg progesterone is administered to a population of subjects in need thereof, and mean parameters are determined for samples (e.g., blood and plasma samples) from the subjects administered the composition. Thus, in some embodiments, administration of the composition to a population of subject produces, in plasma samples from the subjects, one or more of a mean $AUC_{(0-t)}$ for estradiol that is from 280.7467 pg·hr/ml to 438.6667 pg·hr/ml, a mean $C_{max}$ for estradiol that is from 12.9580 pg/ml to 20.2469 pg/ml, and a mean $T_{max}$ for estradiol that is from 7.2 hr to 11.3 hr. In some embodiments, administration of the composition to a population of subject produces, in plasma samples from the subjects, one or more of a mean $AUC_{(0-t)}$ for progesterone that is from 48.0348 ng·hr/ml to 75.0543 ng·hr/ml, a mean $C_{max}$ for progesterone that is from 35.6889 ng/ml to 55.7639 ng/ml, and a mean $T_{max}$ for progesterone that is from 2.4 hr to 3.8 hr. In some embodiments, administration of the composition to a population of subject produces, in plasma samples from the subjects, one or more of a mean $AUC_{(0-t)}$ for estrone that is from 1819.2181 pg·hr/ml to 2842.5283 pg·hr/ml, a mean $C_{max}$ for estrone that is from 85.3098 pg/ml to 133.2966 pg/ml, and a mean $T_{max}$ for estrone that is from 4.4 hr to 6.9 hr. In some embodiments, administration of the composition to a population of subject produces, in plasma samples from the subjects, one or more of a mean $AUC_{(0-t)}$ for total estrone that is from 40.3505 ng·hr/ml to 63.0476 ng·hr/ml, a mean $C_{max}$ for total estrone that is from 7.0858 ng/ml to 11.0715 ng/ml, and a mean $T_{max}$ for total estrone that is from 2 hr to 3.1 hr.

In some embodiments, method of treating a subject with a pharmaceutical composition comprising estradiol and progesterone are provided. In some embodiments, the method comprises administering to the subject a pharmaceutical composition comprising about 0.50 mg estradiol and about 100 mg progesterone as described herein (e.g., a pharmaceutical composition having the formulation of Formulation C in Table 3 above), wherein administration of the pharmaceutical composition produces, in a plasma sample from the subject, one or more parameters selected from: an $AUC_{(0-t)}$ for estradiol that is from 280.7467 pg·hr/ml to 438.6667 pg·hr/ml; a $C_{max}$ for estradiol that is from 12.9580 pg/ml to 20.2469 pg/ml; a $T_{max}$ for estradiol that is from 7.2 hr to 11.3 hr; an $AUC_{(0-t)}$ for progesterone that is from 48.0348 ng·hr/ml to 75.0543 ng·hr/ml; a $C_{max}$ for progesterone that is from 35.6889 ng/ml to 55.7639 ng/ml; a $T_{max}$ for progesterone that is from 2.4 hr to 3.8 hr; an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; a $T_{max}$ for estrone that is from 4.4 hr to 6.9 hr; an $AUC_{(0-t)}$ for total estrone that is from 40.3505 ng·hr/ml to 63.0476 ng·hr/ml; a $C_{max}$ for total estrone that is from 7.0858 ng/ml to 11.0715 ng/ml; and a $T_{max}$ for total estrone that is from 2 hr to 3.1 hr.

In some embodiments, the method further comprises obtaining a sample from the subject (e.g., a blood or plasma sample) following administration of a single dose of the pharmaceutical composition (e.g., a pharmaceutical composition having the formulation of Formulation C in Table 3 above), and measuring one or more pharmacokinetic parameters selected from an $AUC_{(0-t)}$ for estradiol, a $C_{max}$ for estradiol, an $AUC_{(0-t)}$ for progesterone, a $C_{max}$ for progesterone, an $AUC_{(0-t)}$ for estrone, a $C_{max}$ for estrone, an $AUC_{(0-t)}$ for total estrone, and a $C_{max}$ for total estrone; wherein the presence of one or more of the following values is indicative of a therapeutically effective dose: an $AUC_{(0-t)}$ for estradiol that is from 280.7467 pg·hr/ml to 438.6667 pg·hr/ml; a $C_{max}$ for estradiol that is from 12.9580 pg/ml to 20.2469 pg/ml; an $AUC_{(0-t)}$ for progesterone that is from 48.0348 ng·hr/ml to 75.0543 ng·hr/ml; a $C_{max}$ for progesterone that is from 35.6889 ng/ml to 55.7639 ng/ml; an $AUC_{(0-t)}$ for estrone that is from 1819.2181 pg·hr/ml to 2842.5283 pg·hr/ml; a $C_{max}$ for estrone that is from 85.3098 pg/ml to 133.2966 pg/ml; an $AUC_{(0-t)}$ for total estrone that is from 40.3505 ng·hr/ml to 63.0476 ng·hr/ml; and a $C_{max}$ for total estrone that is from 7.0858 ng/ml to 11.0715 ng/ml. In some embodiments, the one or more pharmacokinetic parameters are measured about 18 hours, about 24 hours, about 18-36 hours, about 20-30 hours, about 22-26 hours, about 24-36 hours, about 36 hours, about 36-48 hours, about 40-48 hours, or about 48 hours after administration of the single dose.

AUC, $C_{max}$, and $T_{max}$ Parameters (D)

In some embodiments, a pharmaceutical composition of this disclosure comprises estradiol at a dosage of about 1 mg and progesterone at a dosage of about 100 mg. In some embodiments, the pharmaceutical composition comprises the formulation of Formulation D in Table 4 above.

In some embodiments, administration of a composition comprising about 1 mg estradiol and about 100 mg progesterone to a subject produces, in a plasma sample from the subject, one or both parameters selected from:
  (i) an $AUC_{(0-t)}$ for estradiol that is from 561.4933 pg·hr/ml to 877.3333 pg·hr/ml; or
  (ii) a $C_{max}$ for estradiol that is from 25.9161 pg/ml to 40.4939 pg/ml.

In some embodiments, administration of the composition to the subject produces both an $AUC_{(0-t)}$ for estradiol that is from 561.4933 pg·hr/ml to 877.3333 pg·hr/ml, and a $C_{max}$ for estradiol that is from 25.9161 pg/ml to 40.4939 pg/ml.

In some embodiments, administration of the composition to the subject further produces, in a plasma sample from the subject, one or both parameters selected from:

(i) an $AUC_{(0-t)}$ for progesterone that is from 48.0348 ng·hr/ml to 75.0543 ng·hr/ml; or (ii) a $C_{max}$ for progesterone that is from 35.6889 ng/ml to 55.7639 ng/ml.

In some embodiments, administration of the composition to the subject produces both an $AUC_{(0-t)}$ for progesterone that is from 48.0348 ng·hr/ml to 75.0543 ng·hr/ml, and a $C_{max}$ for progesterone that is from 35.6889 ng/ml to 55.7639 ng/ml.

In some embodiments, administration of the composition to the subject produces, in a plasma sample from the subject, (i) an $AUC_{(0-t)}$ for estradiol that is from 561.4933 pg·hr/ml to 877.3333 pg·hr/ml;

(ii) a $C_{max}$ for estradiol that is from 25.9161 pg/ml to 40.4939 pg/ml;

(iii) an $AUC_{(0-t)}$ for progesterone that is from 48.0348 ng·hr/ml to 75.0543 ng·hr/ml; or (iv) a $C_{max}$ for progesterone that is from 35.6889 ng/ml to 55.7639 ng/ml.

In some embodiments, administration of the composition to the subject further produces, in a plasma sample from the subject, a $T_{max}$ for estradiol that is from 7.2 hr to 11.3 hr. In some embodiments, administration of the composition to the subject further produces, in a plasma sample from the subject, a $T_{max}$ for progesterone that is from 2.4 hr to 3.8 hr.

In some embodiments, administration of the composition to the subject produces, in a plasma sample from the subject, one, two, three or more parameters selected from:

(i) an $AUC_{(0-t)}$ for estradiol that is from 561.4933 pg·hr/ml to 877.3333 pg·hr/ml;

(ii) a $C_{max}$ for estradiol that is from 25.9161 pg/ml to 40.4939 pg/ml;

(iii) an $AUC_{(0-t)}$ for progesterone that is from 48.0348 ng·hr/ml to 75.0543 ng·hr/ml; or (iv) a $C_{max}$ for progesterone that is from 35.6889 ng/ml to 55.7639 ng/ml.

In some embodiments, administration of the pharmaceutical composition to the subject produces both parameters (i) and (ii). In some embodiments, administration of the composition to the subject produces both parameters (i) and (iii). In some embodiments, administration of the composition to the subject produces both parameters (i) and (iv). In some embodiments, administration of the composition to the subject produces both parameters (ii) and (iii). In some embodiments, administration of the composition to the subject produces both parameters (ii) and (iv). In some embodiments, administration of the composition to the subject produces both parameters (iii) and (iv). In some embodiments, administration of the composition to the subject produces all of parameters (i), (ii), and (iii). In some embodiments, administration of the composition to the subject produces both parameters (i), (iii), and (iv). In some embodiments, administration of the composition to the subject produces both parameters (ii), (iii), and (iv). In some embodiments, administration of the composition to the subject produces all of parameters (i), (ii), (iii), and (iv).

In some embodiments, administration of the pharmaceutical composition to the subject further produces, in a plasma sample from the subject, one or more parameters selected from:

(i) an $AUC_{(0-t)}$ for estrone that is from 3638.4363 pg·hr/ml to 5685.0567 pg·hr/ml;

(ii) a $C_{max}$ for estrone that is from 170.6197 pg/ml to 266.5933 pg/ml; or (iii) a $T_{max}$ for estrone that is from 4.4 hr to 6.9 hr.

In some embodiments, administration of the pharmaceutical composition to the subject further produces, in a plasma sample from the subject, one or more parameters selected from:

(i) an $AUC_{(0-t)}$ for total estrone that is from 80.7010 ng·hr/ml to 126.0953 ng·hr/ml;

(ii) a $C_{max}$ for total estrone that is from 14.1716 ng/ml to 22/1431 ng/ml; or (iii) a $T_{max}$ for total estrone that is from 2 hr to 3.1 hr.

In some embodiments, a pharmaceutical composition comprising about 1 mg estradiol and about 100 mg progesterone is administered to a population of subjects in need thereof, and mean parameters are determined for samples (e.g., blood or plasma samples) from the subjects administered the composition. Thus, in some embodiments, administration of the composition to a population of subject produces, in plasma samples from the subjects, one or more of a mean $AUC_{(0-t)}$ for estradiol that is from 561.4933 pg·hr/ml to 877.3333 pg·hr/ml, a mean $C_{max}$ for estradiol that is from 25.9161 pg/ml to 40.4939 pg/ml, and a mean $T_{max}$ for estradiol that is from 7.2 hr to 11.3 hr. In some embodiments, administration of the composition to a population of subject produces, in plasma samples from the subjects, one or more of a mean $AUC_{(0-t)}$ for progesterone that is from 48.0348 ng·hr/ml to 75.0543 ng·hr/ml, a mean $C_{max}$ for progesterone that is from 35.6889 ng/ml to 55.7639 ng/ml, and a mean $T_{max}$ for progesterone that is from 2.4 hr to 3.8 hr. In some embodiments, administration of the composition to a population of subjects produces, in plasma samples from the subjects, one or more of a mean $AUC_{(0-t)}$ for estrone that is from 3638.4363 pg·hr/ml to 5685.0567 pg·hr/ml, a mean $C_{max}$ for estrone that is from 170.6197 pg/ml to 266.5933 pg/ml, and a mean $T_{max}$ for estrone that is from 4.4 hr to 6.9 hr. In some embodiments, administration of the composition to a population of subject produces, in plasma samples from the subjects, one or more of a mean $AUC_{(0-t)}$ for total estrone that is from 80.7010 ng·hr/ml to 126.0953 ng·hr/ml, a mean $C_{max}$ for total estrone that is from 14.1716 ng/ml to 22/1431 ng/ml, and a mean $T_{max}$ for total estrone that is from 2 hr to 3.1 hr.

In some embodiments, method of treating a subject with a pharmaceutical composition comprising estradiol and progesterone are provided. In some embodiments, the method comprises administering to the subject a pharmaceutical composition comprising about 1 mg estradiol and about 100 mg progesterone as described herein (e.g., a pharmaceutical composition having the formulation of Formulation D in Table 4 above), wherein administration of the pharmaceutical composition produces, in a plasma sample from the subject, one or more parameters selected from: an $AUC_{(0-t)}$ for estradiol that is from 561.4933 pg·hr/ml to 877.3333 pg·hr/m; a $C_{max}$ for estradiol that is from 25.9161 pg/ml to 40.4939 pg/ml; a $T_{max}$ for estradiol that is from 7.2 hr to 11.3 hr; an $AUC_{(0-t)}$ for progesterone that is from 48.0348 ng·hr/ml to 75.0543 ng·hr/ml; a $C_{max}$ for progesterone that is from 35.6889 ng/ml to 55.7639 ng/ml; a $T_{max}$ for progesterone that is from 2.4 hr to 3.8 hr; an $AUC_{(0-t)}$ for estrone that is from 3638.4363 pg·hr/ml to 5685.0567 pg·hr/ml; a $C_{max}$ for estrone that is from 170.6197 pg/ml to 266.5933 pg/ml; a $T_{max}$ for estrone that is from 4.4 hr to 6.9 hr; an $AUC_{(0-t)}$ for total estrone that is from 80.7010 ng·hr/ml to 126.0953 ng·hr/ml; a $C_{max}$ for total estrone that is from 14.1716 ng/ml to 22/1431 ng/ml; and a $T_{max}$ for total estrone that is from 2 hr to 3.1 hr.

In some embodiments, the method further comprises obtaining a sample from the subject (e.g., a blood or plasma sample) following administration of a single dose of the pharmaceutical composition (e.g., a pharmaceutical composition having the formulation of Formulation D in Table 4 above), and measuring one or more pharmacokinetic parameters selected from an $AUC_{(0-t)}$ for estradiol, a $C_{max}$ for estradiol, an $AUC_{(0-t)}$ for progesterone, a $C_{max}$ for progesterone, an $AUC_{(0-t)}$ for estrone, a $C_{max}$ for estrone, an $AUC_{(0-t)}$ for total estrone, and a $C_{max}$ for total estrone; wherein the presence of one or more of the following values is indicative of a therapeutically effective dose: an $AUC_{(0-t)}$ for estradiol that is from 561.4933 pg·hr/ml to 877.3333 pg·hr/m; a $C_{max}$ for estradiol that is from 25.9161 pg/ml to 40.4939 pg/ml; an $AUC_{(0-t)}$ for progesterone that is from 48.0348 ng·hr/ml to 75.0543 ng·hr/ml; a $C_{max}$ for progesterone that is from 35.6889 ng/ml to 55.7639 ng/ml; an $AUC_{(0-t)}$ for estrone that is from 3638.4363 pg·hr/ml to 5685.0567 pg·hr/ml; a $C_{max}$ for estrone that is from 170.6197 pg/ml to 266.5933 pg/ml; an $AUC_{(0-t)}$ for total estrone that is from 80.7010 ng·hr/ml to 126.0953 ng·hr/ml; and a $C_{max}$ for total estrone that is from 14.1716 ng/ml to 22/1431 ng/ml. In some embodiments, the one or more pharmacokinetic parameters are measured about 18 hours, about 24 hours, about 18-36 hours, about 20-30 hours, about 22-26 hours, about 24-36 hours, about 36 hours, about 36-48 hours, about 40-48 hours, or about 48 hours after administration of the single dose.

AUC, $C_{max}$, and $T_{max}$ Parameters (E)

In some embodiments, a pharmaceutical composition of this disclosure comprises estradiol at a dosage of about 2 mg and progesterone at a dosage of about 200 mg. In some embodiments, the pharmaceutical composition comprises the formulation of Formulation E in Table 5 above.

In some embodiments, administration of a pharmaceutical composition comprising about 2 mg estradiol and about 200 mg progesterone to a subject produces, in a plasma sample from the subject, one or both parameters selected from:
(i) an $AUC_{(0-t)}$ for estradiol that is from 1123 pg·h/ml to 1755 pg·h/ml; or
(ii) a $C_{max}$ for estradiol that is from 52 pg/ml to 81 pg/ml.

In some embodiments, administration of the composition to the subject produces both an $AUC_{(0-t)}$ for estradiol that is from 1123 pg·h/ml to 1755 pg·h/ml, and a $C_{max}$ for estradiol that is from 52 pg/ml to 81 pg/ml.

In some embodiments, administration of the composition to the subject further produces, in a plasma sample from the subject, one or both parameters selected from:
(i) an $AUC_{(0-t)}$ for progesterone that is from 96 ng·hr/ml to 150 ng·hr/ml; or
(ii) a $C_{max}$ for progesterone that is from 71 ng/ml to 112 ng/ml.

In some embodiments, administration of the composition to the subject produces both an $AUC_{(0-t)}$ for progesterone that is from 96 ng·hr/ml to 150 ng·hr/ml, and a $C_{max}$ for progesterone that is from 71 ng/ml to 112 ng/ml.

In some embodiments, administration of the composition to the subject produces, in a plasma sample from the subject,
(i) an $AUC_{(0-t)}$ for estradiol that is from 1123 pg·h/ml to 1755 pg·h/ml;
(ii) a $C_{max}$ for estradiol that is from 52 pg/ml to 81 pg/ml;
(iii) an $AUC_{(0-t)}$ for progesterone that is from 96 ng·hr/ml to 150 ng·hr/ml; or
(iv) a $C_{max}$ for progesterone that is from 71 ng/ml to 112 ng/ml.

In some embodiments, administration of the composition to the subject further produces, in a plasma sample from the subject, a $T_{max}$ for estradiol that is from 7.2 hr to 11.3 hr. In some embodiments, administration of the composition to the subject further produces, in a plasma sample from the subject, a $T_{max}$ for progesterone that is from 2.4 hr to 3.8 hr.

In some embodiments, administration of the pharmaceutical composition to the subject produces, in a plasma sample from the subject, one, two, three or more parameters selected from:
(i) an $AUC_{(0-t)}$ for estradiol that is from 1123 pg·h/ml to 1755 pg·h/ml;
(ii) a $C_{max}$ for estradiol that is from 52 pg/ml to 81 pg/ml;
(iii) an $AUC_{(0-t)}$ for progesterone that is from 96 ng·hr/ml to 150 ng·hr/ml; or
(iv) a $C_{max}$ for progesterone that is from 71 ng/ml to 112 ng/ml.

In some embodiments, administration of the pharmaceutical composition to the subject produces both parameters (i) and (ii). In some embodiments, administration of the composition to the subject produces both parameters (i) and (iii). In some embodiments, administration of the composition to the subject produces both parameters (i) and (iv). In some embodiments, administration of the composition to the subject produces both parameters (ii) and (iii). In some embodiments, administration of the composition to the subject produces both parameters (ii) and (iv). In some embodiments, administration of the composition to the subject produces both parameters (iii) and (iv). In some embodiments, administration of the composition to the subject produces all of parameters (i), (ii), and (iii). In some embodiments, administration of the composition to the subject produces both parameters (i), (iii), and (iv). In some embodiments, administration of the composition to the subject produces both parameters (ii), (iii), and (iv). In some embodiments, administration of the composition to the subject produces all of parameters (i), (ii), (iii), and (iv).

In some embodiments, administration of the pharmaceutical composition to the subject further produces, in a plasma sample from the subject, one or more parameters selected from:
(i) an $AUC_{(0-t)}$ for estrone that is from 7277 pg·hr/ml to 11370 pg·hr/ml;
(ii) a $C_{max}$ for estrone that is from 341 pg/ml to 533 pg/ml; or
(iii) a $T_{max}$ for estrone that is from 4.4 hr to 6.9 hr.

In some embodiments, administration of the pharmaceutical composition to the subject further produces, in a plasma sample from the subject, one or more parameters selected from:
(i) an $AUC_{(0-t)}$ for total estrone that is from 161 ng·h/ml to 252 ng·h/ml
(ii) a $C_{max}$ for total estrone that is from 28 ng/ml to 44 ng/ml; or
(iii) a $T_{max}$ for total estrone that is from 2 hr to 3.1 hr.

In some embodiments, a pharmaceutical composition comprising about 2 mg estradiol and about 200 mg progesterone is administered to a population of subjects in need thereof, and mean parameters are determined for samples (e.g., blood or plasma samples) from the subjects administered the composition. Thus, in some embodiments, administration of the composition to a population of subject produces, in plasma samples from the subjects, one or more of a mean $AUC_{(0-t)}$ for estradiol that is from 1123 pg·h/ml to 1755 pg·h/ml, a mean $C_{max}$ for estradiol that is from 52 pg/ml to 81 pg/ml, and a mean $T_{max}$ for estradiol that is from 7.2 hr to 11.3 hr. In some embodiments, administration of the composition to a population of subject produces, in plasma samples from the subjects, one or more of a mean $AUC_{(0-t)}$ for progesterone that is from 96 ng·hr/ml to 150 ng·hr/ml, a mean $C_{max}$ for progesterone that is from 71 ng/ml to 112 ng/ml, and a mean $T_{max}$ for progesterone that is from 2.4 hr to 3.8 hr. In some embodiments, administration of the composition to a population of subject produces, in plasma samples from the subjects, one or more of a mean $AUC_{(0-t)}$ for estrone that is from 7277 pg·hr/ml to 11370 pg·hr/ml, a mean $C_{max}$ for estrone that is from 341 pg/ml to 533 pg/ml, and a mean $T_{max}$ for estrone that is from 4.4 hr to 6.9 hr. In some embodiments, administration of the composition to a population of subject produces, in plasma samples from the subjects, one or more of a mean $AUC_{(0-t)}$ for total estrone that is from 161 ng·h/ml to 252 ng·h/ml, a mean $C_{max}$ for total estrone that is from 28 ng/ml to 44 ng/ml, and a mean $T_{max}$ for total estrone that is from 2 hr to 3.1 hr.

In some embodiments, method of treating a subject with a pharmaceutical composition comprising estradiol and progesterone are provided. In some embodiments, the method comprises administering to the subject a pharmaceutical composition comprising about 2 mg estradiol and about 200 mg progesterone as described herein (e.g., a pharmaceutical composition having the formulation of Formulation E in Table 5 above), wherein administration of the pharmaceutical composition produces, in a plasma sample from the subject, one or more parameters selected from: an $AUC_{(0-t)}$ for estradiol that is from 1123 pg·h/ml to 1755 pg·h/ml; a $C_{max}$ for estradiol that is from 52 pg/ml to 81 pg/ml; a $T_{max}$ for estradiol that is from 7.2 hr to 11.3 hr; an $AUC_{(0-t)}$ for progesterone that is from 96 ng·hr/ml to 150 ng·hr/ml; a $C_{max}$ for progesterone that is from 71 ng/ml to 112 ng/ml; a $T_{max}$ for progesterone that is from 2.4 hr to 3.8 hr; an $AUC_{(0-t)}$ for estrone that is from 7277 pg·hr/ml to 11370 pg·hr/ml; a $C_{max}$ for estrone that is from 341 pg/ml to 533 pg/ml; a $T_{max}$ for estrone that is from 4.4 hr to 6.9 hr; an $AUC_{(0-t)}$ for total estrone that is from 161 ng·h/ml to 252 ng·h/ml; a $C_{max}$ for total estrone that is from 28 ng/ml to 44 ng/ml; and a $T_{max}$ for total estrone that is from 2 hr to 3.1 hr.

In some embodiments, the method further comprises obtaining a sample from the subject (e.g., a blood or plasma sample) following administration of a single dose of the pharmaceutical composition (e.g., a pharmaceutical composition having the formulation of Formulation E in Table 5 above), and measuring one or more pharmacokinetic parameters selected from an $AUC_{(0-t)}$ for estradiol, a $C_{max}$ for estradiol, an $AUC_{(0-t)}$ for progesterone, a $C_{max}$ for progesterone, an $AUC_{(0-t)}$ for estrone, a $C_{max}$ for estrone, an $AUC_{(0-t)}$ for total estrone, and a $C_{max}$ for total estrone; wherein the presence of one or more of the following values is indicative of a therapeutically effective dose: an $AUC_{(0-t)}$ for estradiol that is from 1123 pg·h/ml to 1755 pg·h/ml; a $C_{max}$ for estradiol that is from 52 pg/ml to 81 pg/ml; an $AUC_{(0-t)}$ for progesterone that is from 96 ng·hr/ml to 150 ng·hr/ml; a $C_{max}$ for progesterone that is from 71 ng/ml to 112 ng/ml; an $AUC_{(0-t)}$ for estrone that is from 7277 pg·hr/ml to 11370 pg·hr/ml; a $C_{max}$ for estrone that is from 341 pg/ml to 533 pg/ml; an $AUC_{(0-t)}$ for total estrone that is from 161 ng·h/ml to 252 ng·h/ml; and a $C_{max}$ for total estrone that is from 28 ng/ml to 44 ng/ml. In some embodiments, the one or more pharmacokinetic parameters are measured about 18 hours, about 24 hours, about 18-36 hours, about 20-30 hours, about 22-26 hours, about 24-36 hours, about 36 hours, about 36-48 hours, about 40-48 hours, or about 48 hours after administration of the single dose.

Figure 2:
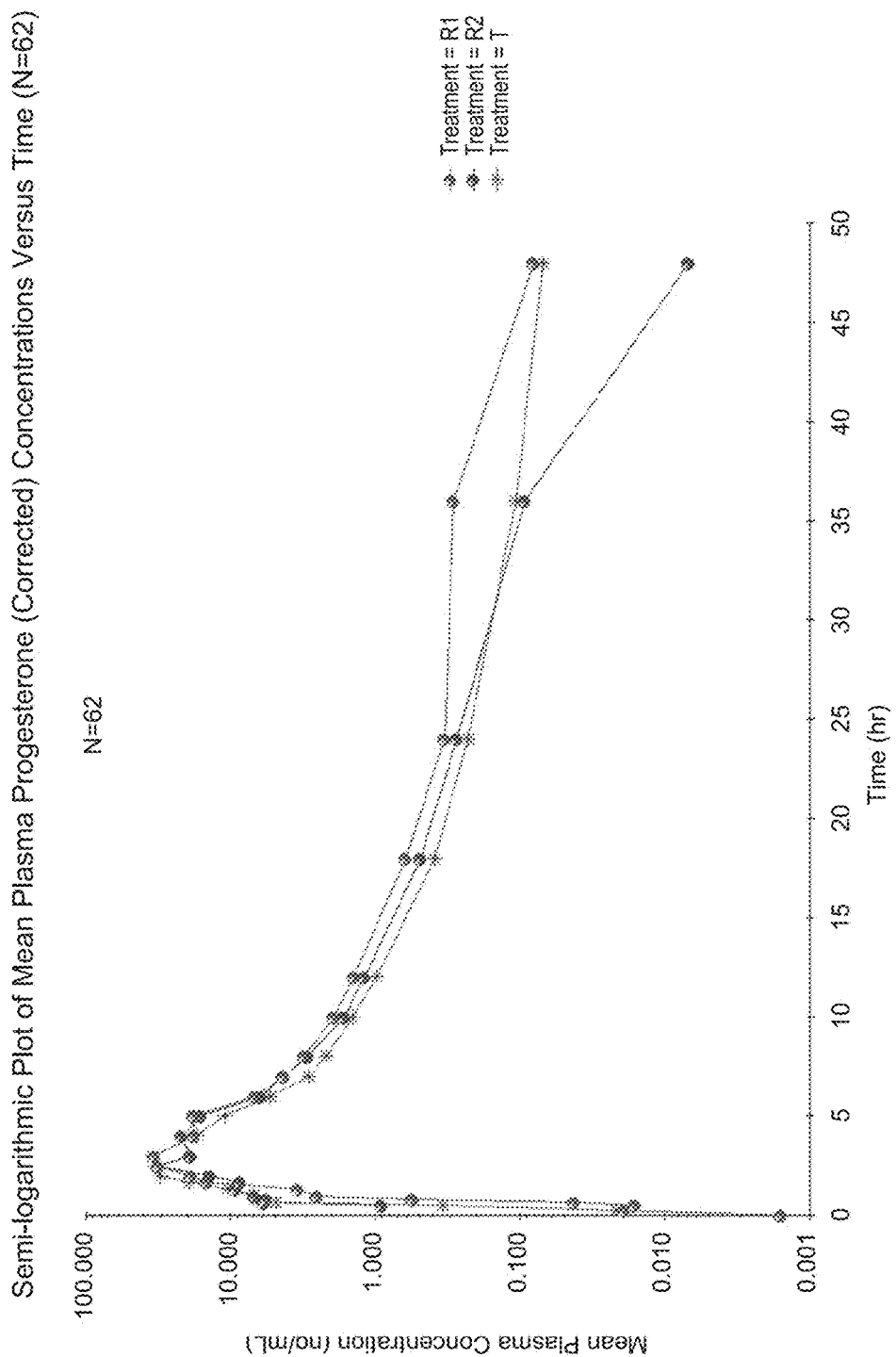
FIG. 2 illustrates a semilogarithmic plot of mean plasma concentration (ng/ml) over time (hrs) for progesterone.
Figure 3:
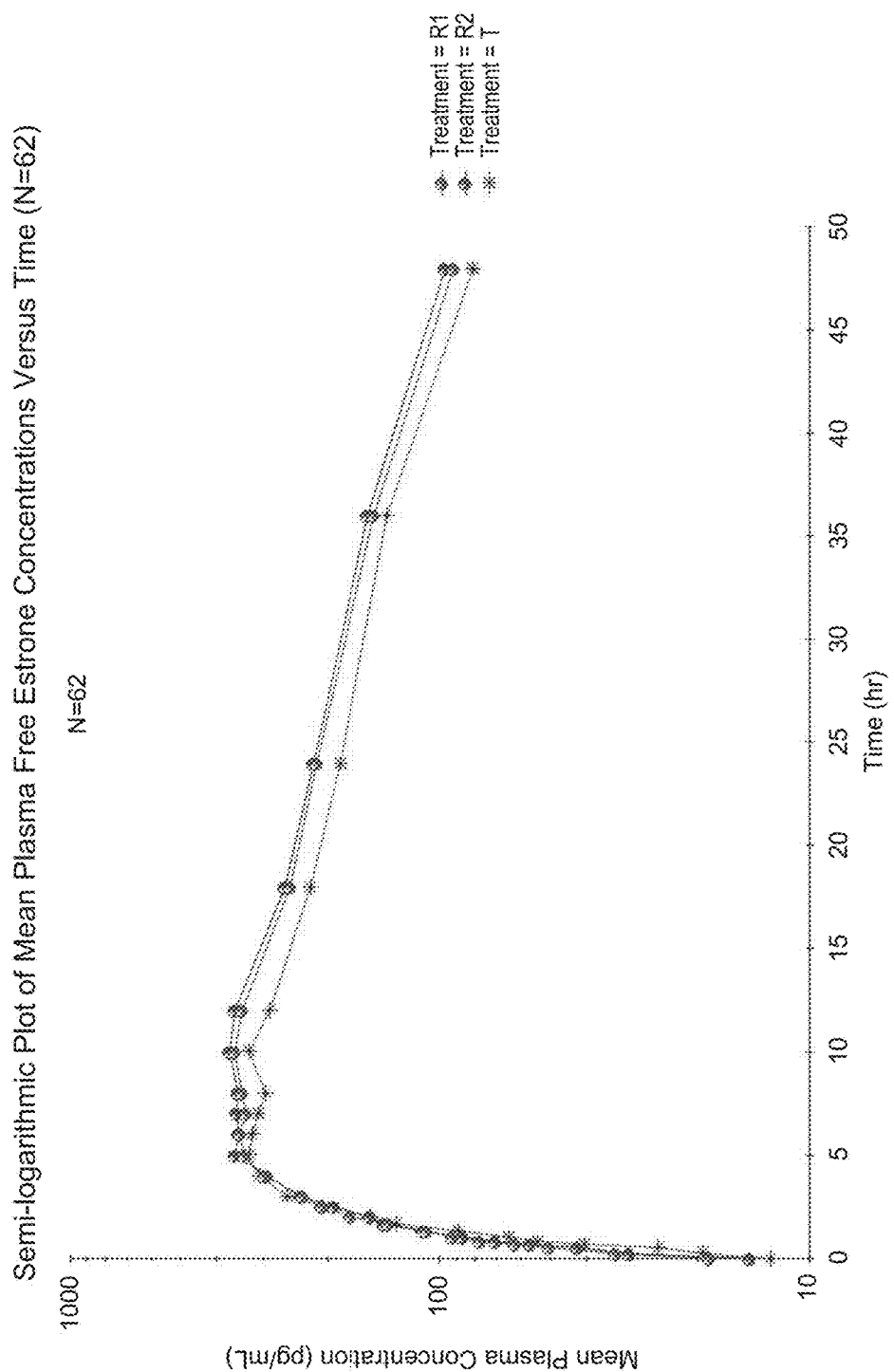
FIG. 3 illustrates a semilogarithmic plot of mean plasma concentration (pg/ml) over time (hrs) for estrone.
Figure 4:
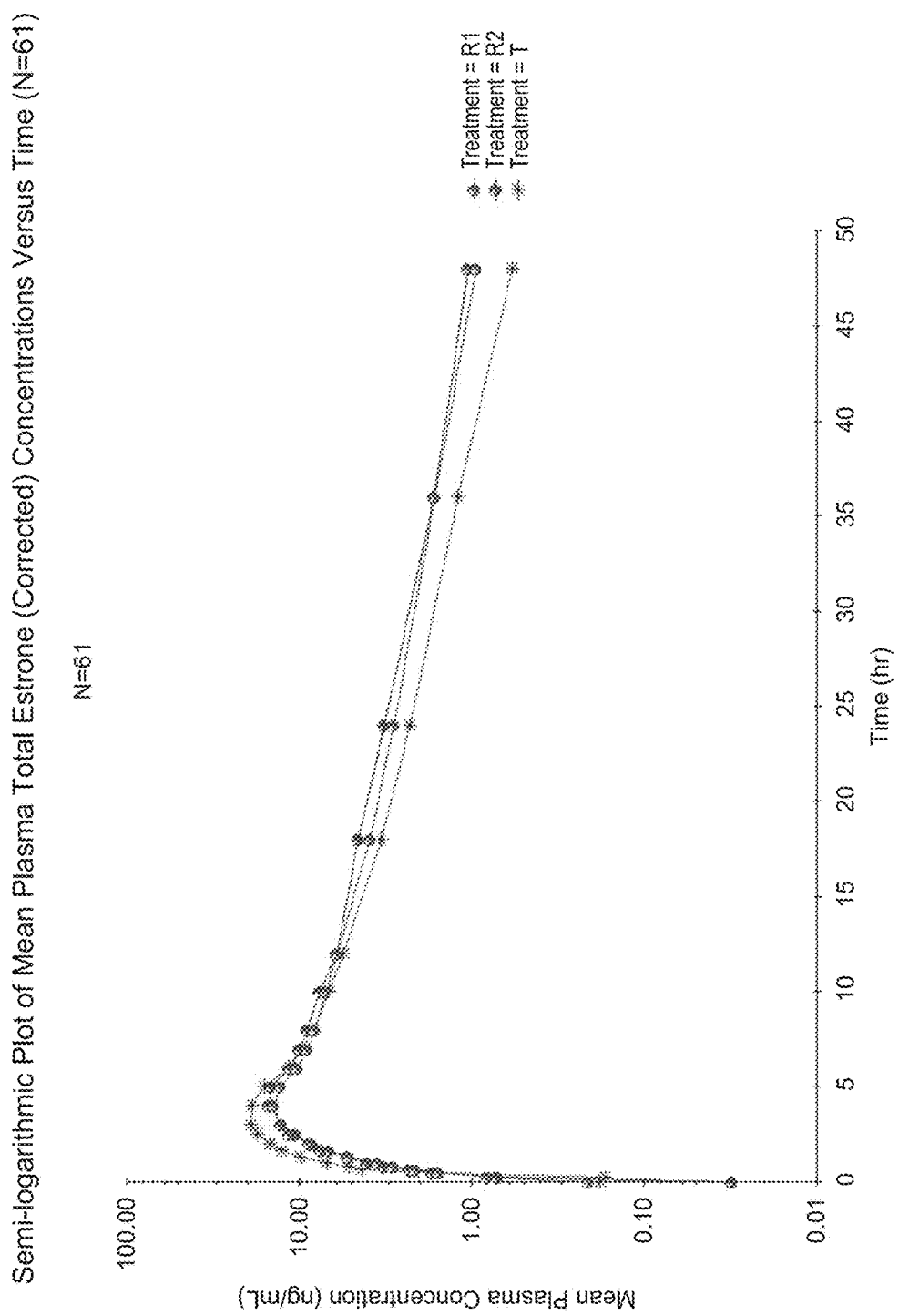
FIG. 4 illustrates a semilogarithmic plot of mean plasma concentration (ng/ml) over time (hrs) for total estrone.

In some embodiments, administration of the pharmaceutical composition as described herein results in the blood plasma estradiol concentration profile of FIG. 1. In some embodiments, administration of the pharmaceutical composition results in the blood plasma progesterone concentration profile of FIG. 2. In some embodiments, administration of the pharmaceutical composition results in the blood plasma estrone concentration profile of FIG. 3. In some embodiments, administration of the pharmaceutical composition results in the blood plasma total estrone concentration profile of FIG. 4.

Administration and Treatment

Pharmaceutical compositions comprising estradiol and progesterone as described herein (e.g., compositions comprising solubilized estradiol, suspended progesterone, and a medium chain solubilizing agent) can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. In some embodiments, administration is by injection, that is, intravenously, intramuscularly, intracutaneously, subcutaneously, intraduodenally, or intraperitoneally.

For preparing pharmaceutical compositions from the compounds of this disclosure, the pharmaceutically acceptable compositions can be either solid or liquid. Solid form preparations include powders, tablets, pills, capsules, cachets, suppositories, and dispersible granules. A solid preparation can comprise one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In general, the type of composition is selected based on the mode of administration. A pharmaceutical composition (e.g., for oral administration or delivery by injection) can be in the form of a liquid (e.g., an elixir, syrup, solution, emulsion or suspension). Alternatively, a pharmaceutical composition as described herein can take the form of a pill, tablet, or capsule containing the liquid oil, and thus, the composition can contain any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The composition can also be formulated into a suppository disposed, for example, in a polyethylene glycol (PEG) solubilizing agent.

Administration of the compositions of this disclosure can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. In some embodiments, a composition as described herein is administered orally. For example, a pharmaceutical composition as described herein can be administered via capsules such as soft capsules.

In some embodiments, a pharmaceutical composition as described herein is administered once daily for a period of 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 days or more. In some embodiments, a pharmaceutical composition as described herein is administered daily for at least one week, at least two weeks, at least three weeks, at least four weeks, at least one month, at least two months, at least three months, at least four months, at least five months, at least six months, at least seven months, at least eight months, at least nine months, at least ten months, at least eleven months, at least twelve months, or more. In some embodiments, a pharmaceutical composition as described herein is administered as a continuous-combined therapy regimen.

In some embodiments, a 28-day or monthly regimen of daily doses is packaged in a single kit (e.g., a blister pack) having administration days identified to improve compliance and reduce associated symptoms, among others. In some embodiments, each daily dose contains both estradiol and progesterone. In some embodiments, one or more of the daily doses contains no estradiol or no progesterone. Daily doses that comprise no estradiol or progesterone API may be referred to as placebos. A blister pack can have a plurality of scores or perforations separating the blister pack into 28 days. Each day may further comprise a single blister or a plurality of blisters. In various embodiments, each unit dose may contain micronized or partially solubilized, or fully solubilized progesterone or solubilized estradiol in amounts as set forth herein, although other dose ranges may be contemplated. In addition, kits having other configurations are also contemplated herein. For example, without limitation, kits having such blister packs may contain any number of daily doses.

In some embodiments, the pharmaceutical compositions disclosed herein are useful in treating conditions in subjects caused, at least in part, by estrogen deficiency, particularly for women with a uterus. For example, in embodiments, the pharmaceutical compositions disclosed herein are useful for the treatment of one or more of the following conditions: endometrial hyperplasia; secondary amenorrhea; prevention of preterm birth, when the subject has a shortened cervix; menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvovaginal atrophy; and osteoporosis and other non-menopausal disease states or conditions treated with supplemental progesterone or estrogen. In some embodiments, the pharmaceutical compositions disclosed herein are useful in treating vasomotor symptoms, including but not limited to, hot flashes and night sweats. In some embodiments, the pharmaceutical compositions disclosed herein are useful in treating hot flashes and night sweats. In some embodiments, the pharmaceutical compositions disclosed herein are useful in treating hot flashes. Thus, in some embodiments, this disclosure provides methods of treating such a condition by administering to the subject a composition comprising estradiol and progesterone as described herein.

III. EXAMPLES

The following examples are offered to illustrate, but not to limit, the claimed subject matter.

Example 1

In an exemplary embodiment, a soft gelatin capsule contains a pharmaceutical composition comprising suspended progesterone and solubilized estradiol:

TABLE 6

| Ingredient | Mass (mg) | % w/w | Qty/Capsule (mg) |
|---|---|---|---|
| Progesterone, USP, micronized | 50.00 | 7.14 | 50.00 |
| Estradiol Hemihydrate, USP | 2.03 | 0.29 | 2.03 |
| CAPMUL ® MCM, NF | | 82.57 | 577.97 |
| GELUCIRE ® 44/14, NF | | 10.0 | 70.00 |
| TOTAL | | 100.00 | 700.00 |

The encapsulated pharmaceutical composition of Table 6 may be manufactured in any suitable manner. For the purposes of this Example, mixing may be facilitated by an impellor, agitator, or other suitable means. Also for the purposes of this Example, heating or mixing may be performed under an inert or relatively inert gas atmosphere, such as nitrogen gas ($N_2$). Mixing or heating for the purposes of this Example may be performed in any suitable vessel, such as a stainless steel vessel.

For example, CAPMUL® MCM may be heated to between 30° C. to 50° C., more preferably from 35° C. to 45° C., and more preferably to 40° C.±2° C. GELUCIRE® 44/14 may be added to the CAPMUL® MCM and mixed until dissolved (to increase the solubility of progesterone in the final solution, GELUCIRE® 44/14 was added at about 10% w/w). The addition may occur all at once or may occur gradually over a period of time. Heat may continue to be applied during the mixing of the GELUCIRE® 44/14 and the CAPMUL® MCM.

Heat may be removed from the GELUCIRE® 44/14 and CAPMUL® MCM mixture. Estradiol Hemihydrate may be added to the mixture. The addition may occur all at once or may occur gradually over a period of time. Micronized progesterone may then be added to the GELUCIRE® 44/14, CAPMUL® MCM and Estradiol Hemihydrate mixture until dissolved. The addition may occur all at once or may occur gradually over a period of time.

Example 2

An example of the final scale-up formulation is provided in Table 7. To manufacture, CAPMUL® MCM is heated to 40° C. GELUCIRE® 44/14 is heated to 65° C. and added and mixed until dissolved. Heat is removed. Estradiol is added and mixed until dissolved. Micronized progesterone is then added and mixed until fully suspended.

TABLE 7

Quantitative Formula: Batch Size 10,000 capsules

| Item No. | Ingredient | Label Claim (mg) | % w/w | Qty/ Capsule (mg) | Amount/ Batch (kg) |
|---|---|---|---|---|---|
| 1. | Progesterone, USP, micronized | 50.00 | 7.14 | 50.00 | 0.50 |
| 2. | Estradiol Hemihydrate, USP | 2.03 | 0.29 | 2.03 | 0.02 |
| 3. | CAPMUL ® MCM, NF | | 82.57 | 577.97 | 5.78 |
| 4. | GELUCIRE ® 44/14, NF | | 10.0 | 70.00 | 0.70 |
| | Total: | | 100.00 | 700.00 | 7.00 |

Example 3

In an exemplary embodiment, a soft gelatin capsule contains a pharmaceutical composition having fully solubilized estradiol and partially solubilized progesterone comprising:

TABLE 8

| Item No. | Ingredient | Label Claim (mg) | % w/w | Qty/ Capsule (mg) | Amount/ Batch (g) |
|---|---|---|---|---|---|
| 1. | Progesterone, USP, micronized | 50.00 | 25.000 | 50.00 | 500.00 |
| 2. | Estradiol Hemihydrate | 0.25 | 0.129 | 0.26 | 2.58 |
| 3. | CAPMUL® MCM, NF | | 73.371 | 146.74 | 1467.42 |
| 4. | GELUCIRE® 44/14, NF | | 1.500 | 3.00 | 30.00 |
| | Total: | | 100.000 | 200.00 mg | 2000.00 |

To manufacture, CAPMUL® MCM is heated to 65° C. GELUCIRE® 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 4

In an exemplary embodiment, a soft gelatin capsule contains a pharmaceutical composition having fully solubilized estradiol and partially solubilized progesterone comprising:

TABLE 9

| Item No. | Ingredient | Label Claim (mg) | % w/w | Qty/ Capsule (mg) | Amount/ Batch (g) |
|---|---|---|---|---|---|
| 1. | Progesterone, USP, micronized | 200.00 | 33.33 | 200.0 | 2000.0 |
| 2. | Estradiol Hemihydrate | 2.00 | 0.35 | 2.07 | 20.7 |
| 3. | CAPMUL® MCM, NF | | 65.32 | 391.93 | 3919.3 |
| 4. | GELUCIRE® 44/14, NF | | 1.00 | 6.0 | 60.0 |
| | Total: | | 100.00 | 600.0 mg | 6000.0 |

To manufacture, CAPMUL® MCM is heated to 65° C. GELUCIRE® 44/14 is added and mixed until dissolved. Heat is removed. Estradiol is added and mixed until dissolved. Micronized progesterone is then added and dispersed. The mixture is then passed through a colloid mill. The resulting pharmaceutical composition is encapsulated in soft gelatin capsules. Alternatively, GELUCIRE® 44/14 is heated to 65° C. and CAPMUL® MCM is heated to 40° C.±5° C. to achieve mixing of the oil and the surfactant before heat is removed; estradiol is added while the mixture is cooling; progesterone is added when the mixture has dropped below about 40° C.; the mixture is then passed through a colloid mill one or more times, e.g., three times.

Example 5

Pharmacokinetics of the First Combination 17β-Estradiol/Progesterone Capsule in Clinical Development for Hormone Therapy The objective of this study was to evaluate the pharmacokinetic and oral bioavailability of a combination capsule of 17β-estradiol/progesterone in comparison to co-administration of the individual products ESTRACE® and PROMETRIUM®.

Subjects and Study Design:

An open label, balanced, randomized, single-dose, 2-treatment, 3-period, 3-sequence, crossover, partial-replicate, reference-scaled, oral, relative bioavailability study compared the bioavailability of an investigational 2-mg 17β-estradiol/200-mg progesterone combination capsule, without peanut oil (formulated in a manner similar to that set forth in Table 9), with that of co-administered 200-mg PROMETRIUM® (progesterone) and 2-mg ESTRACE® (17β-estradiol) tablets in healthy postmenopausal women aged 40-65 years (N=66). Key inclusion criteria for subjects included a BMI 18.50 to 29.99 kg/m$^2$ who were nonsmokers or ex-smokers (no smoking in the last 3 months). Key exclusion criteria for subjects included consuming grapefruit juice or poppy-containing foods within 48 hours before and throughout the study, use of any hormonal agent within 14 days before the study, and use of menopausal hormone therapy within 6 months before dosing.

Patients were randomly assigned sequentially to 1 of 3 dosing sequences of the same dose of the combination capsule (Test, T) and reference products (Reference, R): TRR, RTR, or RRT. 66 subjects were randomized and 62 (94.0%) completed the study. Subjects had a mean age of 49.5±5.6 years (range 40 to 64) and a mean BMI of 24.8±3.1 kg/m$^2$ (range 18.7-29.9).

After consuming a high-fat, high-calorie breakfast, each woman received a single dose of the combination (Test) capsule in 1 period of the study and single doses of the co-administered products (Reference) in each of the 2 remaining periods. Blood samples were collected within 75 minutes before dosing and post-dose at 0.25, 0.5, 0.67, 0.83, 1, 1.33, 1.67, 2, 2.5, 3, 4, 5, 6, 7, 8, 10, 12, 18, 24, 36, and 48 hours after dosing to determine progesterone, free (unconjugated) estradiol, and free and total (conjugated+free, including estrone sulfates) estrone concentrations. After collection of blood samples at each time point, the blood samples were centrifuged at 4000 RPM for 10 minutes at 4° C. to separate the plasma. The plasma from samples was separated into two aliquots. 1.5 mL from the plasma sample was transferred into aliquot I, and the remaining plasma sample was transferred into aliquot II. These aliquots were stored at −30° C. for interim storage, then at −70° C. until completion of the analysis.

Progesterone, estradiol, estrone, and total estrone in human plasma was determined using the LC-MS/MS method. The primary ($C_{max}$, $AUC_{0-t}$, and $AUC_{0-\infty}$) and secondary ($T_{max}$, $t_{1/2}$, and $K_e$) PK parameters for each analyte were determined for each subject during each period by non-compartment analyses using baseline-adjusted concentrations. Statistical analyses were conducted using the SAS® statistical software.

Results: The mean, standard deviation (SD), geometric mean, coefficient of variation (CV %), minimum, median, and maximum were calculated for $C_{max}$, $AUC_{0-t}$, $AUC_{0-\infty}$, $T_{max}$, $t_{1/2}$, $K_{el}$, $K_{el\_lower}$, $K_{el\_Upper}$, and $AUC_{\%Extrap\_obs}$ for progesterone, estradiol, estrone, and total estrone. The results are presented in Tables 10, 11, 12, and 13 below. For each of Tables 10-13, "Test Product (T)" refers to the progesterone+estradiol pharmaceutical composition, while "Reference product (R1)" and "Reference product (R2)" refers to co-administered PROMETRIUM® (progesterone) and ESTRACE® (estradiol). Blood plasma concentrations of progesterone, estradiol, estrone, and total estrone over time are also shown in FIGS. 1-4.

TABLE 10

Summary of Pharmacokinetic Parameters of Test Product (T) versus Reference Product ($R_1$, $R_2$) for Progesterone

| PK Parameter | N | Test Product (T) | N | Reference product (R1) | N | Reference product (R2) |
|---|---|---|---|---|---|---|
| $C_{max}$ (ng/mL) | 62 | 89.2222 ± 149.7309 | 62 | 72.7228 ± 101.8885 | 62 | 69.7590 ± 87.0777 |
| $AUC_{0-t}$ (ng · hr/mL) | 62 | 120.0869 ± 164.1385 | 62 | 125.9406 ± 152.3483 | 62 | 111.5867 ± 113.3200 |
| $AUC_{0-\infty}$ (ng · hr/mL) | 57 | 131.3817 ± 172.4806 | 57 | 142.1332 ± 160.4853 | 56 | 126.6006 ± 117.2665 |
| $T_{max}$ (hr) | 62 | 3.00 (0.83-10.00) | 62 | 3.00 (1.00-12.00) | 62 | 4.00 (0.67-18.00) |
| $K_{el}$ ($hr^{-1}$) | 57 | 0.3064 ± 0.2427 | 57 | 0.2684 ± 0.1912 | 56 | 0.2795 ± 0.2475 |
| $t_{1/2}$ (hr) | 57 | 4.6445 ± 4.5366 | 57 | 5.1555 ± 4.9794 | 56 | 5.0389 ± 4.5887 |
| $K_{el\_Lower}$ ($hr^{-1}$) | 57 | 7.6667 ± 4.6047 | 57 | 7.4123 ± 4.2164 | 56 | 7.9018 ± 3.9120 |
| $K_{el\_Upper}$ ($hr^{-1}$) | 57 | 16.2218 ± 11.0051 | 57 | 19.1728 ± 12.3801 | 56 | 18.1975 ± 10.0858 |
| AUC_Extra (%) | 57 | 4.3374 ± 2.5528 | 57 | 4.8416 ± 3.7526 | 56 | 5.1868 ± 4.1434 |

*Expressed in terms of median (range)

TABLE 11

Summary of Pharmacokinetic Parameters of Test Product (T) versus Reference Product ($R_1$, $R_2$) for Estradiol

| PK Parameter | Test Product (T) | Reference product (R1) | Reference product (R2) |
|---|---|---|---|
| $C_{max}$ (pg/mL) | 64.7902 ± 50.9833 | 69.1286 ± 33.0484 | 73.4236 ± 43.4077 |
| $AUC_{0-t}$ (pg · hr/mL) | 1403.7333 ± 763.8136 | 1508.2206 ± 876.7390 | 1658.2502 ± 976.5556 |
| $AUC_{0-\infty}$ (pg · hr/mL) | 2459.4394 ± 4498.2737 | 2842.8805 ± 4582.6502 | 2110.9591 ± 1175.3995 |
| $T_{max}$ (hr) | 9.00(0.50-36.00) | 10.0(0.50-35.12) | 10.00(0.25-36.60) |
| $K_{el}$ ($hr^{-1}$) | 0.0438 ± 0.0197 | 0.0457 ± 0.0358 | 0.0464 ± 0.0338 |
| $t_{1/2}$ (hr) | 31.9104 ± 95.9769 | 25.0908 ± 28.8346 | 20.8774 ± 12.0825 |
| $K_{el\_Lower}$ ($hr^{-1}$) | 14.9472 ± 7.2715 | 14.9667 ± 7.0150 | 14.7953 ± 5.8774 |
| $K_{el\_Upper}$ ($hr^{-1}$) | 45.3602 ± 6.3668 | 44.3277 ± 7.4003 | 43.8330 ± 7.6449 |
| AUC_Extra (%) | 22.8106 ± 16.6498 | 25.4773 ± 20.2911 | 24.9566 ± 16.4713 |

*Expressed in terms of median (range)

TABLE 12

Summary of Pharmacokinetic Parameters of Test Product (T) versus Reference Product ($R_1$, $R_2$) for Free Estrone

| PK Parameter | Test Product (T) | Reference product (R1) | Reference product (R2) |
|---|---|---|---|
| $C_{max}$ (pg/mL) | 426.5492 ± 179.3303 | 455.5107 ± 189.448 | 467.2302 ± 207.4373 |
| $AUC_{0-t}$ (pg · hr/mL) | 9096.0907 ± 4377.2730 | 10156.0282 ± 5140.5831 | 10507.3557 ± 5183.1289 |
| $AUC_{0-\infty}$ (pg · hr/mL) | 11994.9695 ± 6678.5468 | 13445.9048 ± 8699.4068 | 14066.2362 ± 7563.2370 |
| $T_{max}$ (hr) | 5.50(0.83-36.00) | 8.00(1.67-18.00) | 10.00(1.67-18.00) |
| $K_{el}$ ($hr^{-1}$) | 0.0399 ± 0.0146 | 0.0424 ± 0.0172 | 0.0406 ± 0.0209 |
| $t_{1/2}$ (hr) | 20.3172 ± 9.4052 | 19.4595 ± 9.8711 | 20.7515 ± 9.3985 |
| $K_{el\_Lower}$ ($hr^{-1}$) | 13.8443 ± 7.0649 | 14.8871 ± 6.6459 | 14.9194 ± 6.4485 |
| $K_{el\_Upper}$ ($hr^{-1}$) | 46.0238 ± 5.5080 | 46.2547 ± 5.3060 | 46.2244 ± 5.3126 |
| AUC_Extra (%) | 21.2980 ± 11.2283 | 20.3648 ± 11.1060 | 21.8900 ± 11.8537 |

*Expressed in terms of median (range)

TABLE 13

Summary of Pharmacokinetic Parameters of Test Product (T) versus Reference Product ($R_1$, $R_2$) for Total Estrone

| PK Parameter | N | Test Product (T) | N | Reference product (R1) | N | Reference product (R2) |
|---|---|---|---|---|---|---|
| $C_{max}$ (ng/mL) | 61 | 35.4289 ± 17.0856 | 61 | 19.8716 ± 7.4485 | 61 | 19.9048 ± 8.0288 |
| $AUC_{0-t}$ (ng · hr/mL) | 61 | 201.7524 ± 94.2081 | 61 | 182.7729 ± 88.8386 | 61 | 199.8295 ± 94.9392 |
| $AUC_{0-\infty}$ (ng · hr/mL) | 61 | 213.2402 ± 104.6011 | 60 | 193.6387 ± 100.5831 | 56 | 203.0289 ± 81.4884 |
| $T_{max}$ (hr) | 61 | 2.50 (0.67-7.00) | 61 | 4.00 (1.33-18.00) | 61 | 4.00 (1.33-10.00) |

TABLE 13-continued

Summary of Pharmacokinetic Parameters of Test Product (T) versus Reference Product (R1, R2) for Total Estrone Untransformed Data (Mean ± SD)

| PK Parameter | N | Test Product (T) | N | Reference product (R1) | N | Reference product (R2) |
|---|---|---|---|---|---|---|
| $K_{el}$ (hr$^{-1}$) | 61 | 0.0799 ± 0.0398 | 60 | 0.0803 ± 0.0399 | 56 | 0.0718 ± 0.0243 |
| $t_{1/2}$ (hr) | 61 | 10.3619 ± 4.0023 | 60 | 9.8448 ± 3.0702 | 56 | 10.7830 ± 3.6624 |
| $K_{el\_Lower}$ (hr$^{-1}$) | 61 | 13.0492 ± 6.8585 | 60 | 13.5945 ± 8.0129 | 56 | 11.8870 ± 6.8696 |
| $K_{el\_Upper}$ (hr$^{-1}$) | 61 | 45.3979 ± 6.6589 | 60 | 46.3775 ± 5.2525 | 56 | 46.7054 ± 4.3888 |
| AUC_Extra (%) | 61 | 4.5030 ± 3.7366 | 60 | 4.5913 ± 3.4953 | 56 | 5.3450 ± 3.9831 |

*Expressed in terms of median (range)

Example 6

Pharmacokinetic data ($C_{max}$, AUC$_{(0-t)}$, AUC$_{(0-\infty)}$, and $T_{max}$) for progesterone, estradiol, free estrone, and total estrone is presented in Tables 14-17. Pharmaceutical compositions A-E are disclosed in Tables 1-5. The pK values for pharmaceutical composition E were calculated as disclosed in Example 5. For pharmaceutical compositions A-D, expected pharmacokinetic data is calculated from the data disclosed for pharmaceutical composition E.

TABLE 14

Summary of Pharmacokinetic Parameters of the Pharmaceutical Compositions of Tables 1-5 for Progesterone

| Pharmaceutical Composition | Progesterone Content | Estradiol Content | $C_{max}$ (ng/mL) | AUC$_{(0-t)}$ (ng · hr/mL) | AUC$_{(0-\infty)}$ (ng · hr/mL) | $T_{max}$ (hr) |
|---|---|---|---|---|---|---|
| A | 50 mg | 0.25 mg | 22.30555 | 30.0217 | 32.8454 | 3.00 |
| B | 50 mg | 0.50 mg | 22.3055 | 30.0217 | 32.8454 | 3.00 |
| C | 100 mg | 0.50 mg | 44.6111 | 60.0435 | 65.6909 | 3.00 |
| D | 100 mg | 1 mg | 44.6111 | 60.0435 | 65.6909 | 3.00 |
| E | 200 mg | 2 mg | 89.2222 | 120.0869 | 131.3817 | 3.00 |

TABLE 15

Summary of Pharmacokinetic Parameters of the Pharmaceutical Compositions of Tables 1-5 for Estradiol

| Pharmaceutical Composition | Progesterone Content | Estradiol Content | $C_{max}$ (pg/mL) | AUC$_{(0-t)}$ (pg · hr/mL) | AUC$_{(0-\infty)}$ (pg · hr/mL) | $T_{max}$ (hr) |
|---|---|---|---|---|---|---|
| A | 50 mg | 0.25 mg | 8.0988 | 175.4667 | 307.4299 | 9.00 |
| B | 50 mg | 0.50 mg | 16.1976 | 350.9333 | 614.8599 | 9.00 |
| C | 100 mg | 0.50 mg | 16.1976 | 350.9333 | 614.8599 | 9.00 |
| D | 100 mg | 1 mg | 32.3951 | 701.8667 | 1229.7197 | 9.00 |
| E | 200 mg | 2 mg | 64.7902 | 1403.7333 | 2459.4394 | 9.00 |

TABLE 16

Summary of Pharmacokinetic Parameters of the Pharmaceutical Compositions of Tables 1-5 for Free Estrone

| Pharmaceutical Composition | Progesterone Content | Estradiol Content | $C_{max}$ (pg/mL) | AUC$_{(0-t)}$ (pg · hr/mL) | AUC$_{(0-\infty)}$ (pg · hr/mL) | $T_{max}$ (hr) |
|---|---|---|---|---|---|---|
| A | 50 mg | 0.25 mg | 53.3187 | 1137.0113 | 1499.3712 | 5.50 |
| B | 50 mg | 0.50 mg | 106.6373 | 2274.0227 | 2998.7424 | 5.50 |
| C | 100 mg | 0.50 mg | 106.6373 | 2274.0227 | 2998.7424 | 5.50 |
| D | 100 mg | 1 mg | 213.2746 | 4548.0454 | 5997.4848 | 5.50 |
| E | 200 mg | 2 mg | 426.5492 | 9096.0907 | 11994.9695 | 5.50 |

TABLE 17

Summary of Pharmacokinetic Parameters of the Pharmaceutical Compositions of Tables 1-5 for Total Estrone

| Pharmaceutical Composition | Progesterone Content | Estradiol Content | $C_{max}$ (ng/mL) | AUC$_{(0-t)}$ (ng · hr/mL) | AUC$_{(0-\infty)}$ (ng · hr/mL) | $T_{max}$ (hr) |
|---|---|---|---|---|---|---|
| A | 50 mg | 0.25 mg | 4.4286 | 25.2191 | 26.6550 | 2.50 |
| B | 50 mg | 0.50 mg | 8.8572 | 50.4381 | 53.3101 | 2.50 |
| C | 100 mg | 0.50 mg | 8.8572 | 50.4381 | 53.3101 | 2.50 |
| D | 100 mg | 1 mg | 17.7145 | 100.8762 | 106.6201 | 2.50 |
| E | 200 mg | 2 mg | 35.4289 | 201.7524 | 213.2402 | 2.50 |

The ranges of expected pK values for each of the pharmaceutical compositions of Tables 1-4 are disclosed in Tables 18-21, respectively.

TABLE 18 pK Ranges for the Pharmaceutical Composition of Table 1 (Pharmaceutical Composition A)

| | $C_{max}$ | AUC$_{(0-t)}$ | AUC$_{(0-\infty)}$ |
|---|---|---|---|
| Progesterone | 17.8444 ng/mL to 27.8819 ng/mL | 24.0174 ng · hr/mL to 37.5272 ng · hr/mL | 26.2763 ng · hr/mL to 41.0568 ng · hr/mL |
| Estradiol | 6.4790 pg/mL to 10.1235 pg/mL | 140.3733 pg · hr/mL to 219.3333 pg · hr/mL | 245.9439 pg · hr/mL to 384.2874 pg · hr/mL |
| Free estrone | 42.6549 pg/mL to 66.6483 pg/mL | 909.6091 pg · hr/mL to 1421.2642 pg · hr/mL | 1199.4970 pg · hr/mL to 1874.2140 pg · hr/mL |

TABLE 18-continued pK Ranges for the Pharmaceutical Composition
of Table 1 (Pharmaceutical Composition A)

|  | $C_{max}$ | $AUC_{(0-t)}$ | $AUC_{(0-\infty)}$ |
|---|---|---|---|
| Total estrone | 3.5429 ng/mL to 5.5358 ng/mL | 20.1752 ng · hr/mL to 31.5238 ng · hr/mL | 21.3240 ng · hr/mL to 33.3188 ng · hr/mL |

TABLE 19 pK Ranges for the Pharmaceutical Composition
of Table 2 (Pharmaceutical Composition B)

|  | $C_{max}$ | $AUC_{(0-t)}$ | $AUC_{(0-\infty)}$ |
|---|---|---|---|
| Progesterone | 17.8444 ng/mL to 27.8819 ng/mL | 24.0174 ng · hr/mL to 37.5272 ng · hr/mL | 26.2763 ng · hr/mL to 41.0568 ng · hr/mL |
| Estradiol | 12.9580 pg/mL to 20.2469 pg/mL | 280.7467 pg · hr/mL to 438.6667 pg · hr/mL | 491.8879 pg · hr/mL to 768.5748 pg · hr/mL |
| Free estrone | 85.3098 pg/mL to 133.2966 pg/mL | 1819.2181 pg · hr/mL to 2842.5283 pg · hr/mL | 2398.9939 pg · hr/mL to 3748.4280 pg · hr/mL |
| Total estrone | 7.0858 ng/mL to 11.0715 ng/mL | 40.3505 ng · hr/mL to 63.0476 ng · hr/mL | 42.6480 ng · hr/mL to 66.6376 ng · hr/mL |

TABLE 20 pK Ranges for the Pharmaceutical Composition
of Table 3 (Pharmaceutical Composition C)

|  | $C_{max}$ | $AUC_{(0-t)}$ | $AUC_{(0-\infty)}$ |
|---|---|---|---|
| Progesterone | 35.6889 ng/mL to 55.7639 ng/mL | 48.0348 ng · hr/mL to 75.0543 ng · hr/mL | 52.5527 ng · hr/mL to 82.1136 ng · hr/mL |
| Estradiol | 12.9580 pg/mL to 20.2469 pg/mL | 280.7467 pg · hr/mL to 438.6667 pg · hr/mL | 491.8879 pg · hr/mL to 768.5748 pg · hr/mL |
| Free estrone | 85.3098 pg/mL to 133.2966 pg/mL | 1819.2181 pg · hr/mL to 2842.5283 pg · hr/mL | 2398.9939 pg · hr/mL to 3748.4280 pg · hr/mL |
| Total estrone | 7.0858 ng/mL to 11.0715 ng/mL | 40.3505 ng · hr/mL to 63.0476 ng · hr/mL | 42.6480 ng · hr/mL to 66.6376 ng · hr/mL |

TABLE 21 pK Ranges for the Pharmaceutical Composition
of Table 4 (Pharmaceutical Composition D)

|  | $C_{max}$ | $AUC_{(0-t)}$ | $AUC_{(0-\infty)}$ |
|---|---|---|---|
| Progesterone | 35.6889 ng/mL to 55.7639 ng/mL | 48.0348 ng · hr/mL to 75.0543 ng · hr/mL | 52.5527 ng · hr/mL to 82.1136 ng · hr/mL |
| Estradiol | 25.9161 pg/mL to 40.4939 pg/mL | 561.4933 pg · hr/mL to 877.3333 pg · hr/mL | 983.7758 pg · hr/mL to 1537.1496 pg · hr/mL |
| Free estrone | 170.6197 pg/mL to 266.5933 pg/mL | 3638.4363 pg · hr/mL to 5685.0567 pg · hr/mL | 4797.9878 pg · hr/mL to 7496.8559 pg · hr/mL |
| Total estrone | 14.1716 ng/mL to 22.1431 ng/mL | 80.7010 ng · hr/mL to 126.0953 ng · hr/mL | 85.2961 ng · hr/mL to 133.2751 ng · hr/mL |

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices or methods. This disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad general meaning of the terms in which the appended claims are expressed. To the extent that these various modifications do not depart from the spirit and scope of the appended claims, they are intended to be encompassed therein.

What is claimed is:

1. A method of treating a subject having vasomotor symptoms associated with estrogen deficiency, the method comprising administering to the subject an effective amount of a pharmaceutical composition comprising:
   about 0.25 mg estradiol, wherein at least 80% of the estradiol in the composition is solubilized estradiol;
   progesterone, wherein the progesterone comprises suspended progesterone; and
   a medium-chain oil comprising medium chain fatty acid esters of glycerol, polyethylene glycol, or propylene glycol, or mixtures thereof, wherein the medium chain fatty acid esters are predominantly esters of C6 to C12 fatty acids, and wherein the entire amount of the estradiol and the progesterone in the composition is present in the oil;
   wherein administration of the composition to the subject produces, in a plasma sample from the subject, one or more parameters selected from:
   (i) an area under the curve $(AUC)_{(0-t)}$ for estradiol that is from 140.3733 pg·hr/ml to 219.3333 pg·hr/ml; and
   (ii) a $C_{max}$ for estradiol that is from 6.4790 pg/ml to 10.1235 pg/ml.

2. The method of claim 1, wherein the subject is female.

3. The method of claim 1, wherein the subject is a woman having a uterus.

4. The method of claim 1, wherein administration of the composition to the subject produces both an $AUC_{(0-t)}$ for estradiol that is from 140.3733 pg·hr/ml to 219.3333 pg·hr/ml and a $C_{max}$ for estradiol that is from 6.4790 pg/ml to 10.1235 pg/ml.

5. The method of claim 1, wherein administration of the composition to the subject further produces, in a plasma sample from the subject, one or both parameters selected from:
   (i) an $AUC_{(0-t)}$ for progesterone that is from 24.0174 ng·hr/ml to 37.5272 ng·hr/ml; and
   (ii) a $C_{max}$ for progesterone that is from 17.8444 ng/ml to 27.8819 ng/ml.

6. The method of claim 1, wherein administration of the composition to the subject further produces, in a plasma sample from the subject, one or both parameters selected from:
   (i) an $AUC_{(0-t)}$ for estrone that is from 909.6091 pg·hr/ml to 1421.2642 pg·hr/ml; and
   (ii) a $C_{max}$ for estrone that is from 42.6549 pg/ml to 66.6483 pg/ml.

7. The method of claim 1, wherein administration of the composition to the subject further produces, in a plasma sample from the subject, one or both parameters selected from:
   (i) an $AUC_{(0-t)}$ for total estrone that is from 20.1752 ng·hr/ml to 31.5238 ng·hr/ml; and
   (ii) a $C_{max}$ for total estrone that is from 3.5429 ng/ml to 5.5358 ng/ml.

8. A method of treating a subject having vasomotor symptoms associated with estrogen deficiency, the method comprising administering to the subject an effective amount of a pharmaceutical composition comprising:
   about 0.5 mg estradiol, wherein at least 80% of the estradiol in the composition is solubilized estradiol;
   progesterone, wherein the progesterone comprises suspended progesterone; and
   a medium-chain oil comprising medium chain fatty acid esters of glycerol, polyethylene glycol, or propylene glycol, or mixtures thereof, wherein the medium chain fatty acid esters are predominantly esters of C6 to C12 fatty acids, and wherein the entire amount of the estradiol and the progesterone in the composition is present in the oil;
   wherein administration of the composition to the subject produces, in a plasma sample from the subject, one or more parameters selected from:
   (i) an area under the curve $(AUC)_{(0-t)}$ for estradiol that is from 280.7467 pg·hr/ml to 438.6667 pg·hr/ml; and
   (ii) a $C_{max}$ for estradiol that is from 12.9580 pg/ml to 20.2469 pg/ml.

9. The method of claim 8, wherein administration of the composition to the subject further produces, in a plasma sample from the subject, one or both parameters selected from:
   (i) an $AUC_{(0-t)}$ for estrone that is from 1819.2181 pg·hr/ml to 2842.5283 pg·hr/ml; and
   (ii) a $C_{max}$ for estrone that is from 85.3098 pg/ml to 133.2966 pg/ml.

10. The method of claim 8, wherein administration of the composition to the subject further produces, in a plasma sample from the subject, one or both parameters selected from:
    (i) an $AUC_{(0-t)}$ for total estrone that is from 40.3505 ng·hr/ml to 63.0476 ng·hr/ml; and
    (ii) a $C_{max}$ for total estrone that is from 7.0858 ng/ml to 11.0715 ng/ml.

11. The method of claim 8, wherein administration of the composition to the subject further produces, in a plasma sample from the subject, one or more parameters selected from:
    (i) an $AUC_{(0-t)}$ for progesterone that is from 48.0348 ng·hr/ml to 75.0543 ng·hr/ml; and
    (ii) a $C_{max}$ for progesterone that is from 35.6889 ng/ml to 55.7639 ng/ml.

12. A method of treating a subject having vasomotor symptoms associated with estrogen deficiency, the method comprising administering to the subject an effective amount of a pharmaceutical composition comprising:
    about 1 mg estradiol, wherein at least 80% of the estradiol in the composition is solubilized estradiol;
    progesterone, wherein the progesterone comprises suspended progesterone; and
    a medium-chain (C6-C12) oil comprising medium chain fatty acid esters of glycerol, polyethylene glycol, or propylene glycol, or mixtures thereof, wherein the medium chain fatty acid esters are predominantly esters of C6 to C12 fatty acids, and wherein the entire amount of the estradiol and the progesterone in the composition is present in the oil;
    wherein administration of the composition to the subject produces, in a plasma sample from the subject, one or more parameters selected from:
    (i) an area under the curve $(AUC)_{(0-t)}$ for estradiol that is from 561.4933 pg·hr/ml to 877.3333 pg·hr/ml; and
    (ii) a $C_{max}$ for estradiol that is from 25.9161 pg/ml to 40.4939 pg/ml.

13. The method of claim 12, wherein administration of the composition to the subject further produces, in a plasma sample from the subject, one or both parameters selected from:
    (i) an $AUC_{(0-t)}$ for estrone that is from 3638.4363 pg·hr/ml to 5685.0567 pg·hr/ml; and (i) a $C_{max}$ for estrone that is from 170.6197 pg/ml to 266.5933 pg/ml.

14. The method of claim 12, wherein administration of the composition to the subject further produces, in a plasma sample from the subject, one or both parameters selected from:

(i) an $AUC_{(0-t)}$ for total estrone that is from 80.7010 ng·hr/ml to 126.0953 ng·hr/ml; and (ii) a $C_{max}$ for total estrone that is from 14.1716 ng/ml to 22.1431 ng/ml.

15. The method of claim 8, wherein administration of the composition to the subject further produces, in a plasma sample from the subject, one or both parameters selected from:

(i) an $AUC_{(0-t)}$ for progesterone that is from 24.0174 ng·hr/ml to 37.5272 ng·hr/ml; and (ii) a $C_{max}$ for progesterone that is from 17.8444 ng/ml to 27.8819 ng/ml.

16. The method of claim 12, wherein administration of the composition to the subject further produces, in a plasma sample from the subject, one or both parameters selected from:

(i) an $AUC_{(0-t)}$ for progesterone that is from 48.0348 ng·hr/ml to 75.0543 ng·hr/ml; and (ii) a $C_{max}$ for progesterone that is from 35.6889 ng/ml to 55.7639 ng/ml.

17. The method of claim 1, wherein the composition comprises about 0.25 mg estradiol and about 50 mg progesterone.

18. The method of claim 8, wherein the composition comprises about 0.5 mg estradiol and about 50 mg progesterone.

19. The method of claim 8, wherein the composition comprises about 0.5 mg estradiol and about 100 mg progesterone.

20. The method of claim 12, wherein the composition comprises about 1 mg estradiol and about 100 mg progesterone.

* * * * *